United States Patent
Davison et al.

(10) Patent No.: US 11,857,283 B2
(45) Date of Patent: Jan. 2, 2024

(54) ARTICULATION JOINT WITH HELICAL LUMEN

(71) Applicant: Cilag GmbH International, Zug (CH)

(72) Inventors: Mark A. Davison, Maineville, OH (US); Jason A. Hill, Loveland, OH (US); William G. Saulenas, Cincinnati, OH (US); Christopher W. Birri, Cincinnati, OH (US); Thomas J. Erb, Loveland, OH (US)

(73) Assignee: Cilag GmbH International, Zug (CH)

( * ) Notice: Subject to any disclaimer, the term of this patent is extended or adjusted under 35 U.S.C. 154(b) by 505 days.

(21) Appl. No.: 17/029,713

(22) Filed: Sep. 23, 2020

(65) Prior Publication Data

US 2021/0129357 A1    May 6, 2021

Related U.S. Application Data

(60) Provisional application No. 62/930,638, filed on Nov. 5, 2019.

(51) Int. Cl.
*A61B 34/00* (2016.01)
*A61B 34/30* (2016.01)
*A61B 17/29* (2006.01)

(52) U.S. Cl.
CPC .............. *A61B 34/71* (2016.02); *A61B 34/30* (2016.02); *A61B 2017/2908* (2013.01)

(58) Field of Classification Search
CPC . A61B 34/71; A61B 34/30; A61B 2017/2908; A61B 2017/00314;

(Continued)

(56) References Cited

U.S. PATENT DOCUMENTS 5,332,055 A     7/1994 Emori et al.
5,873,873 A     2/1999 Smith et al.
(Continued)

FOREIGN PATENT DOCUMENTS

EP     3527160 A2     8/2019

OTHER PUBLICATIONS

International Search Report and Written Opinion dated Mar. 22, 2021, for International Application No. PCT/IB2020/060321, 16 pages.

(Continued)

*Primary Examiner* — Brian T Gedeon
*Assistant Examiner* — Joshua Andrew Schum-Houck
(74) *Attorney, Agent, or Firm* — Frost Brown Todd LLP

(57) ABSTRACT

A surgical instrument and method of operating same includes an end effector and a shaft assembly. The shaft assembly has proximal and distal shaft portions respectively extending along proximal and distal axes, a first elongate member, and an articulation section. The articulation section extends between the proximal and distal shaft portions and is configured to articulate about a first articulation axis and about a second articulation axis to thereby respectively deflect the end effector along a first plane and a second plane. The articulation section has a first lumen radially offset from the proximal and distal axes that longitudinally intersects the first and second articulation axes. The first lumen movably supports the first elongate member such that the radial spacing of the first elongate member is maintained relative to the proximal and distal axes at each of the first and second articulation axes during deflection of the end effector.

20 Claims, 36 Drawing Sheets

(58) Field of Classification Search
CPC ........... A61B 2017/00323; A61B 2017/00327; A61B 2017/0069; A61B 2017/00738; A61B 2018/1455; A61B 2034/301; A61B 17/00234; A61B 17/320092; A61B 18/1445

See application file for complete search history.

(56) References Cited

U.S. PATENT DOCUMENTS

| | | | |
|---|---|---|---|
| 5,980,510 | A | 11/1999 | Tsonton et al. |
| 6,325,811 | B1 | 12/2001 | Messerly |
| 6,500,176 | B1 | 12/2002 | Truckai et al. |
| 6,773,444 | B2 | 8/2004 | Messerly |
| 6,783,524 | B2 | 8/2004 | Anderson et al. |
| 7,112,201 | B2 | 9/2006 | Truckai et al. |
| 7,125,409 | B2 | 10/2006 | Truckai et al. |
| 7,169,146 | B2 | 1/2007 | Truckai et al. |
| 7,186,253 | B2 | 3/2007 | Truckai et al. |
| 7,189,233 | B2 | 3/2007 | Truckai et al. |
| 7,220,951 | B2 | 5/2007 | Truckai et al. |
| 7,309,849 | B2 | 12/2007 | Truckai et al. |
| 7,311,709 | B2 | 12/2007 | Truckai et al. |
| 7,354,440 | B2 | 4/2008 | Truckai et al. |
| 7,381,209 | B2 | 6/2008 | Truckai et al. |
| 8,461,744 | B2 | 6/2013 | Wiener et al. |
| 8,479,969 | B2 | 7/2013 | Shelton, IV |
| 8,573,461 | B2 | 11/2013 | Shelton, IV et al. |
| 8,573,465 | B2 | 11/2013 | Shelton, IV |
| 8,602,288 | B2 | 12/2013 | Shelton, IV et al. |
| 8,616,431 | B2 | 12/2013 | Timm et al. |
| 8,623,027 | B2 | 1/2014 | Price et al. |
| 8,783,541 | B2 | 7/2014 | Shelton, IV et al. |
| 8,800,838 | B2 | 8/2014 | Shelton, IV |
| 8,820,605 | B2 | 9/2014 | Shelton, IV |
| 8,844,789 | B2 | 9/2014 | Shelton, IV et al. |
| 9,023,071 | B2 | 5/2015 | Miller et al. |
| 9,095,367 | B2 | 8/2015 | Olson et al. |
| 9,301,759 | B2 | 4/2016 | Spivey et al. |
| 9,314,308 | B2 | 4/2016 | Parihar et al. |
| 9,381,058 | B2 | 7/2016 | Houser et al. |
| 9,393,037 | B2 | 7/2016 | Olson et al. |
| 9,402,682 | B2 | 8/2016 | Worrell et al. |
| 10,034,683 | B2 | 7/2018 | Monroe et al. |
| 10,039,548 | B2 | 8/2018 | Parihar |
| 10,172,636 | B2 | 1/2019 | Stulen et al. |
| 10,624,709 | B2 | 4/2020 | Remm |
| 2006/0079874 | A1 | 4/2006 | Faller et al. |
| 2007/0191713 | A1 | 8/2007 | Eichmann et al. |
| 2007/0282333 | A1 | 12/2007 | Fortson et al. |
| 2008/0200940 | A1 | 8/2008 | Eichmann et al. |
| 2010/0179540 | A1* | 7/2010 | Marczyk ............ A61B 18/1445 606/41 |
| 2012/0116265 | A1 | 5/2012 | Houser et al. |
| 2012/0215220 | A1 | 8/2012 | Manzo et al. |
| 2012/0292367 | A1 | 11/2012 | Morgan et al. |
| 2016/0287346 | A1* | 10/2016 | Hyodo ................... A61B 34/30 |
| 2019/0125464 | A1 | 5/2019 | Remm |
| 2021/0059707 | A1 | 3/2021 | Hunter et al. |
| 2021/0059708 | A1 | 3/2021 | Hunter et al. |
| 2021/0059709 | A1 | 3/2021 | Black et al. |
| 2021/0059710 | A1 | 3/2021 | Black et al. |
| 2021/0059711 | A1 | 3/2021 | Hunter et al. |

OTHER PUBLICATIONS

U.S. Appl. No. 61/410,603, entitled "Energy-Based Surgical Instruments,", filed Nov. 5, 2010.

\* cited by examiner

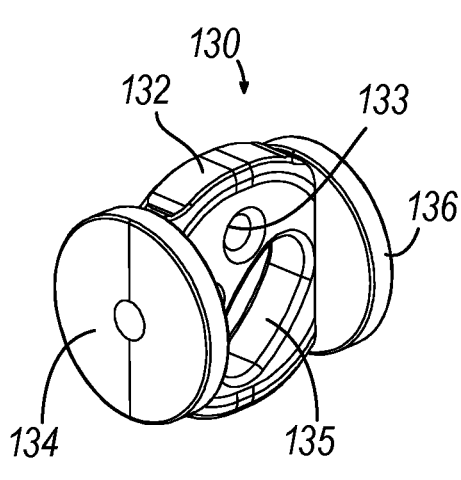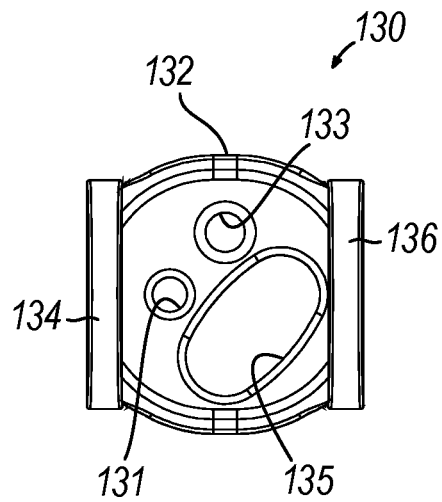
FIG. 37  FIG. 38
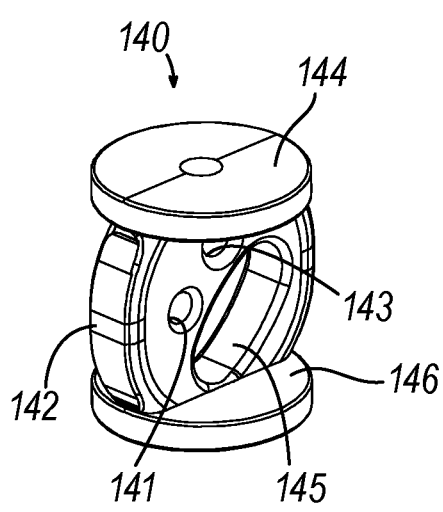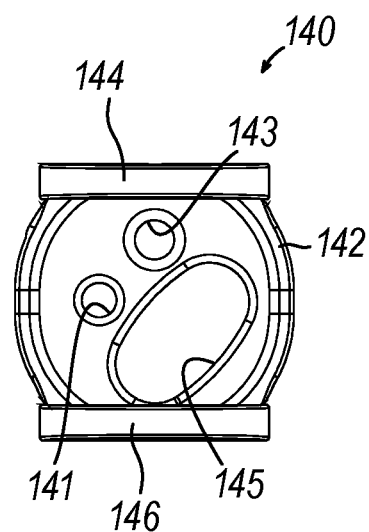
FIG. 39  FIG. 40

ARTICULATION JOINT WITH HELICAL LUMEN

PRIORITY

This application claims priority to U.S. Provisional Patent Application Ser. No. 62/930,638, filed Nov. 5, 2019, entitled "Articulation Joint With Helical Lumen," the disclosure of which is incorporated by reference herein.

BACKGROUND

A variety of surgical instruments include an end effector for engaging tissue in a number of ways to achieve a diagnostic or therapeutic effect. Laparoscopic and endoscopic surgical instruments may be directly gripped and manipulated by a surgeon or incorporated into a robotically assisted surgery.

During robotically assisted surgery, the surgeon may operate a master controller to remotely control the motion of such surgical instruments at a surgical site. The controller may be separated from the patient by a significant distance (e.g., across the operating room, in a different room, or in a completely different building than the patient). Alternatively, a controller may be positioned quite near the patient in the operating room. Regardless, the controller may includes one or more hand input devices (such as joysticks, exoskeletol gloves, master manipulators, or the like), which are coupled by a servo mechanism to the surgical instrument. In one example, a servo motor moves a manipulator supporting the surgical instrument based on the surgeon's manipulation of the hand input devices. During the surgery, the surgeon may employ, via a robotic surgical system, a variety of surgical instruments including an endocutter, grasper, cutter, stapler, clip applier, access device, needle driver, scissors, retractor, spatula, hook, and energy delivery device using ultrasonic vibration, RF, laser, etc. Each of these structures performs functions for the surgeon, for example, clamping tissue, cutting tissue, coagulating tissue, holding or driving a needle, grasping a blood vessel, dissecting tissue, or cauterizing tissue. Positioning of an end effector may be further facilitated through inclusion of one or more articulation joints or features, enabling the end effector to be selectively articulated or otherwise deflected relative to the longitudinal axis of the shaft.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 37 depicts a perspective view of a proximal plate of the multi-planar articulation joint of FIG. 29;

FIG. 38 depicts a side elevational view of the proximal plate of FIG. 37;

FIG. 39 depicts a perspective view of a distal plate of the multi-planar articulation joint of FIG. 29;

FIG. 40 depicts a side elevational view of the distal plate of FIG. 39;

Figure 1:
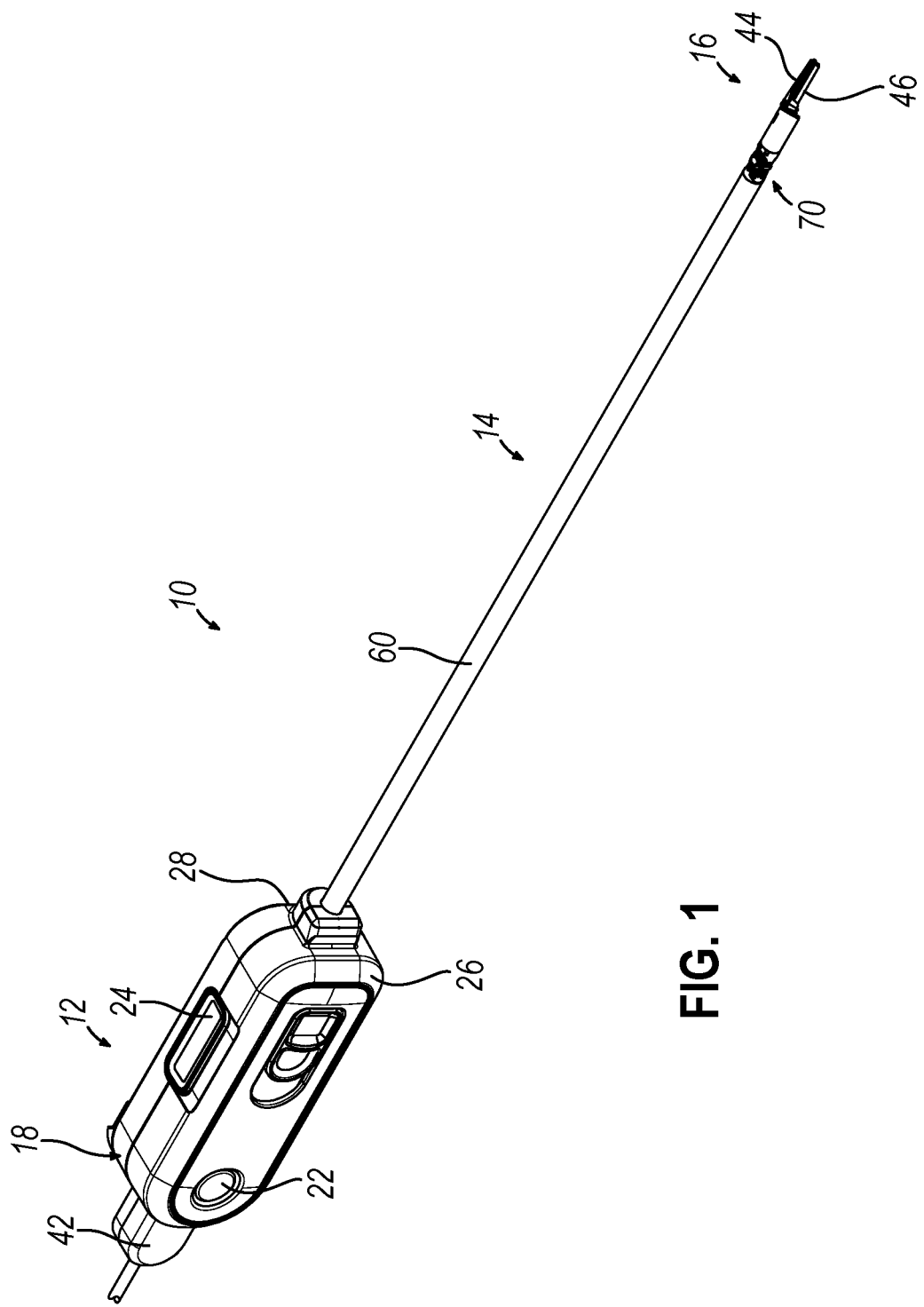
FIG. 1 depicts a front perspective view of a surgical instrument having an end effector, a shaft assembly, and a base assembly configured to connect to a robotic driven interface.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument. It will be further appreciated that, for convenience and clarity, spatial terms such as "front," "side," "top," "bottom," "rear," "horizontally," "vertically," "clockwise," "counterclockwise," "longitudinal," "oblique," and "transverse" also are used herein for reference to relative positions and directions. Such terms are used below with reference to views as illustrated for clarity and are not intended to limit the invention described herein.

I. Exemplary Surgical Instrument

FIG. 1 shows an exemplary surgical instrument (10). Surgical instrument (10) of the present example comprises a body assembly, such as a base assembly (12), a shaft assembly (14), and an end effector (16). At least part of surgical instrument (10) may be constructed and operable in accordance with at least some of the teachings of any of the various patents, patent application publications, and patent applications that are cited herein. As described therein and as will be described in greater detail below, surgical instrument (10) is operable to perform a function, such as clamping tissue, cutting tissue, coagulating tissue, holding or driving a needle, grasping a blood vessel, dissecting tissue, or cauterizing tissue.

A. Exemplary Base Assembly

Figure 2:
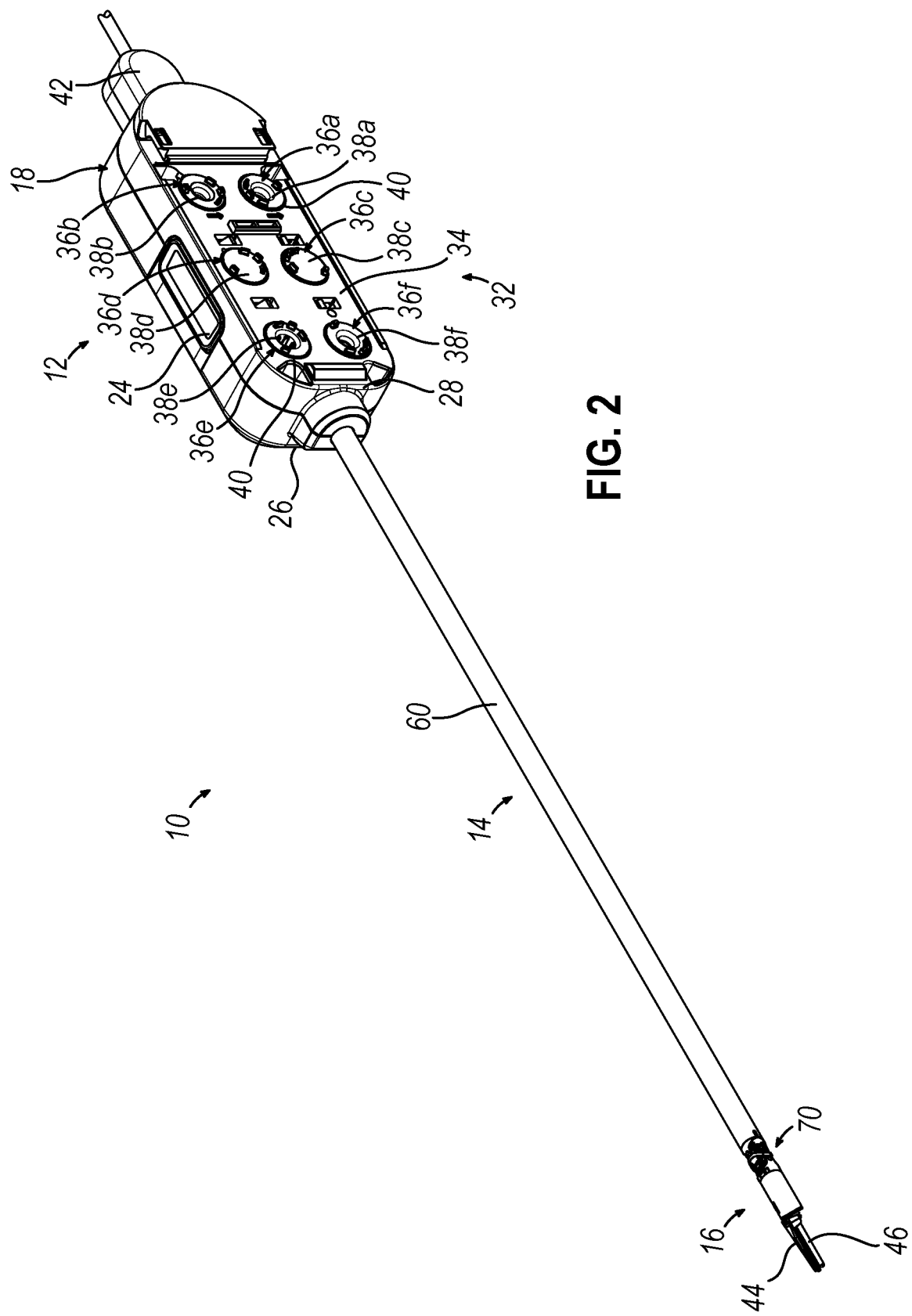
FIG. 2 depicts a rear perspective view of the surgical instrument of FIG. 1.

Referring to FIGS. 1-2, base assembly (12) includes a housing (18), a button (22), and a pair of latch clasps (24). Button (22) is operatively connected to an electrical base power controller (not shown) and configured to selectively power surgical instrument (10) for use. In addition, housing (18) of the present example includes a front housing cover (26) and a rear housing cover (28) removably secured together via latch clasps (24). More particularly, latch clasps (24) removably secure front housing cover (26) to rear housing cover (28) such that front housing cover (26) may be removed for accessing an interior space (not shown) within base assembly (12). Shaft assembly (14) distally extends from base assembly (12) to end effector (16) to thereby communicate mechanical and/or electrical forces therebetween for use as will be discussed below in greater detail. As shown in the present example, base assembly (12) is configured to operatively connect to a robotic drive (not shown) for driving various features of shaft assembly (14) and/or end effector (16). However, in another example, body assembly may alternatively include a handle assembly (not shown), which may include a pistol grip (not shown) in one example, configured to be directly gripped and manipulated by the surgeon for driving various features of shaft assembly (14) and/or end effector (16). The invention is thus not intended to be unnecessarily limited to use with base assembly (12) and the robotic drive (not shown).

To this end, with respect to FIG. 2, base assembly (12) includes a robotic driven interface (32) extending through a base plate (34) of rear housing cover (28) and configured to mechanically couple with the robotic drive (not shown). Robotic driven interface (32) of the present example includes a plurality of instrument actuators (36a, 36b, 36c, 36d, 36e, 36f) having a plurality of input bodies (38a, 38b, 38c, 38d, 38e, 38f), respectively. Each input body (38a, 38b, 38c, 38d, 38e, 38f), which may also be referred to herein as a "puck," is configured to removably connect with the robotic drive (not shown) and, in the present example, is generally cylindrical and rotatable about an axis. Input bodies (38a, 38b, 38c, 38d, 38e, 38f) have a plurality of slots (40) configured to receive portions of the robotic drive (not shown) for gripping and rotatably driving input bodies (38a, 38b, 38c, 38d, 38e, 38f) in order to direct operation of shaft assembly (14) and/or end effector (16) as will be discussed below in greater detail. Base assembly (12) also receives an electrical plug (42) operatively connected to an electrical power source (not shown) to provide electrical power to base assembly (12) for operation as desired, such as powering electrical base power controller (not shown) and directing electrical energy to various features of shaft assembly (14) or end effector (16) associated with cutting, sealing, or welding tissue.

By way of example only, base assembly (12) may alternatively or additionally be configured in accordance with one or more teachings described in U.S. patent application Ser. No. 16/556,661, entitled "Ultrasonic Surgical Instrument with a Multi-Planar Articulating Shaft Assembly," filed on Aug. 30, 2019, published as U.S. Pat. Pub. No. 2021/0059709 on Mar. 4, 2021, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, published as U.S. Pat. Pub. No. 2021/0059710 on Mar. 4, 2021, issued as U.S. Pat. No. 11,612,409; U.S. patent application Ser. No. 16/556,625, entitled "Ultrasonic Surgical Instrument with Axisymmetric Clamping," filed on Aug. 30, 2019, published as U.S. Pat. Pub. No. 2021/0059707 on Mar. 4, 2021, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, U.S. Pat. Pub. No. 2021/0059708 on Mar. 4, 2021, issued as U.S. Pat. No. 11,457,945 on Oct. 4, 2022; and/or U.S. patent application Ser. No. 16/556,727, entitled "Rotatable Linear Actuation Mechanism," filed on Aug. 30, 2019, published as U.S. Pat. Pub. No. 2021/0059711 on Mar. 4, 2021, issued as U.S. Pat. No. 11,712,261 on Aug. 1, 2023. The disclosure of each of these applications is incorporated by reference herein. Alternatively, base assembly (12) may be constructed and/or operable in any other suitable fashion.

B. Exemplary End Effector

Figure 3A:
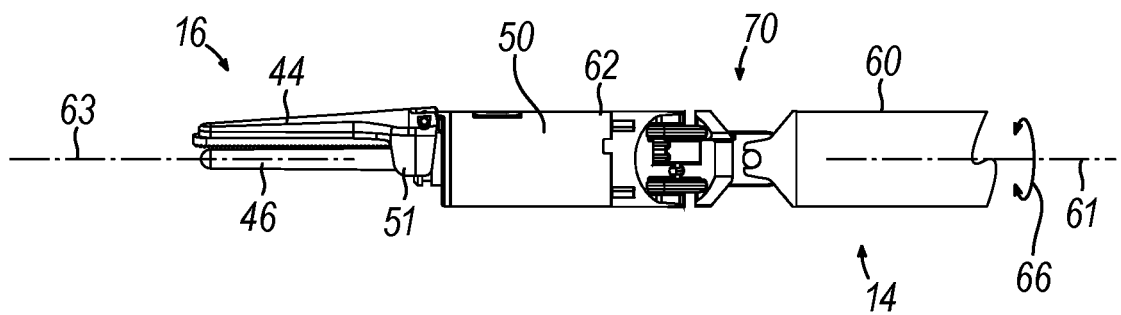
FIG. 3A depicts an enlarged side elevational view of the surgical instrument of FIG. 1 with the end effector in a closed position and the shaft assembly in a straight configuration.
Figure 3B:
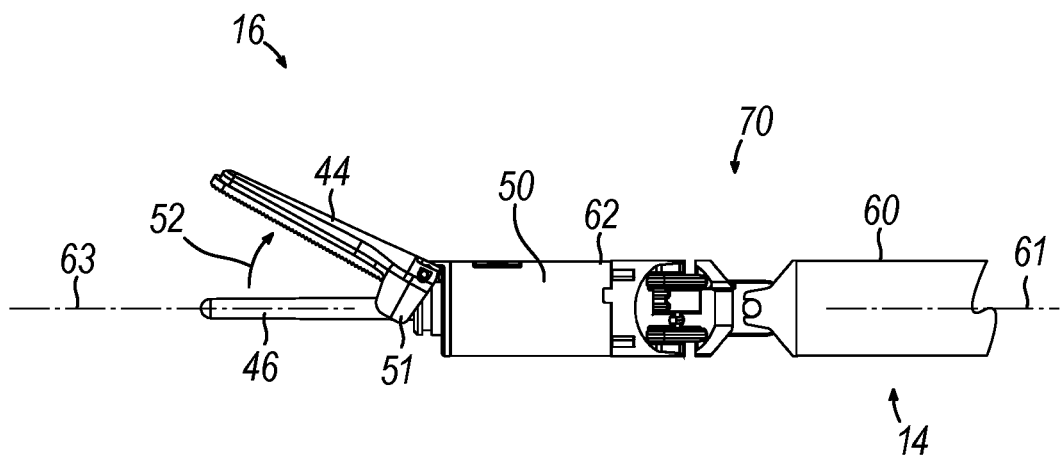
FIG. 3B depicts the enlarged side elevational view of the surgical instrument similar to FIG. 3A, but showing the end effector in an open position.

As best seen in FIGS. 3A-3B, end effector (16) of the present example includes an upper jaw (44) and a lower jaw (46) for clamping tissue. In the illustrated embodiment, upper jaw (44) is pivotally secured to a distally projecting tongue (50) of shaft assembly (14). Upper jaw (44) is operable to selectively pivot toward and away from lower jaw (46) to selectively clamp tissue between upper jaw (44) and lower jaw (46). A pair of arms (51) extend transversely from upper jaw (44) and are pivotally secured to another portion of shaft assembly (14) configured to longitudinally slide to pivot upper jaw (44) as indicated by an arrow (52) between a closed position shown in FIG. 3A and an open position shown in FIG. 3B. While the present example of end effector (16) includes jaws (44, 46) configured to grip tissue for manipulation thereof, it will be appreciated that any such end effector for use with tissue in a surgical procedure may be similarly incorporated into surgical instrument (10). Indeed, other suitable configurations for end effector will be apparent to one with ordinary skill in the art in view of the teachings herein, including, but not limited to, an endocutter, grasper, cutter, stapler, clip applier, access device, needle driver, scissors, retractor, spatula, hook, and energy delivery device using ultrasonic vibration, RF, laser, etc. The invention is thus not intended to be limited to end effector (16) shown in the present example.

More particularly, and by way of example only, end effector (16) may alternatively or additionally be configured in accordance with one or more teachings described in U.S. Pat. Pub. No. 2019/0125464, entitled "Robotic Surgical Tool with Manual Release Lever," published on May 2, 2019, issued as U.S. Pat. No. 10,624,709; U.S. Pat. Pub. No. 2012/0292367, entitled "Robotically-Controlled End Effector," published on Nov. 11, 2012, now abandoned; U.S. Pat. No. 9,314,308, entitled "Robotic Ultrasonic Surgical Device With Articulating End Effector," issued on Apr. 19, 2016; and U.S. Pat. No. 10,039,548, entitled "Clip Applier Adapted for Use with a Surgical Robot," issued on Aug. 7, 2018.

C. Exemplary Shaft Assembly and Articulation Section Having a First Exemplary Multi-Planar Articulation Joint As shown in FIGS. 3A-3B, shaft assembly (14) includes a proximal shaft portion (60) extending along a longitudinal axis (61), a distal shaft portion (62) distally projecting relative to the proximal shaft portion (60) along a distal shaft axis (63), and an articulation section (70) extending between proximal and distal shaft portions (60, 62). Shaft assembly (14) is configured to rotate about longitudinal axis (61) as indicated by an arrow (66). In one example, shaft assembly (14) rotates in the clockwise or counterclockwise directions completely around longitudinal axis (61) and may be selectively fixed in any rotational position about longitudinal axis (61) for positioning articulation section (70) and/or end effector (16) about longitudinal axis (61).

Figure 4:
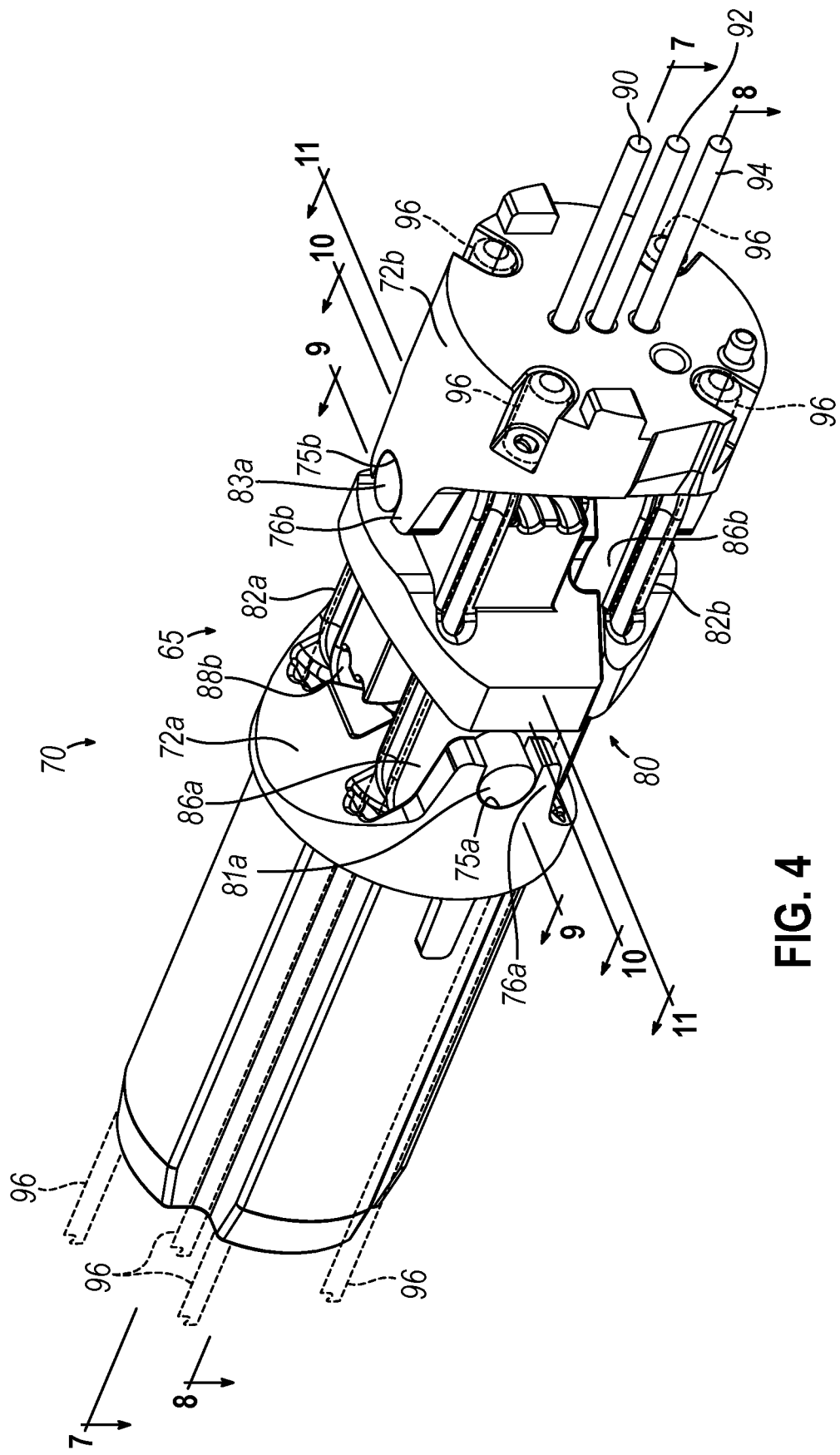
FIG. 4 depicts a perspective view of an articulation section of the shaft assembly of the surgical instrument of FIG. 1 having a first exemplary multi-planar articulation joint.

Articulation section (70) is configured to selectively position end effector (16) at various lateral deflection angles relative to longitudinal axis (61) defined by proximal shaft portion (60). Referring to FIG. 4, articulation section (70) comprises a first exemplary multi-planar articulation joint (65) configured to deflect end effector (16) (see FIG. 3A) through a plurality of planes. Multi-planar articulation joint (65) of the present example includes a proximal articulation joint interface (72a) extending distally from proximal shaft portion (60) (see FIG. 3A), a distal articulation joint interface (72b) extending proximally from distal shaft portion (62) (see FIG. 3A), and an articulation joint core (80) positioned between proximal and distal articulation joint interfaces (72a, 72b). Articulation joint core (80) includes a first articulation joint member (82a) assembled with a second articulation joint member (82b) such that second articulation joint member (82b) is oriented about 90 degrees clockwise relative to first articulation joint member (82a) about longitudinal axis (61). Each of first and second articulation joint members (82a, 82b) are thereby assembled to form articulation joint core (80), which is pivotable relative to longitudinal axis (61) of proximal shaft portion (60) (see FIG. 3A) to position end effector (16) (see FIG. 3A) in various positions about longitudinal axis (61).

Figure 5A:
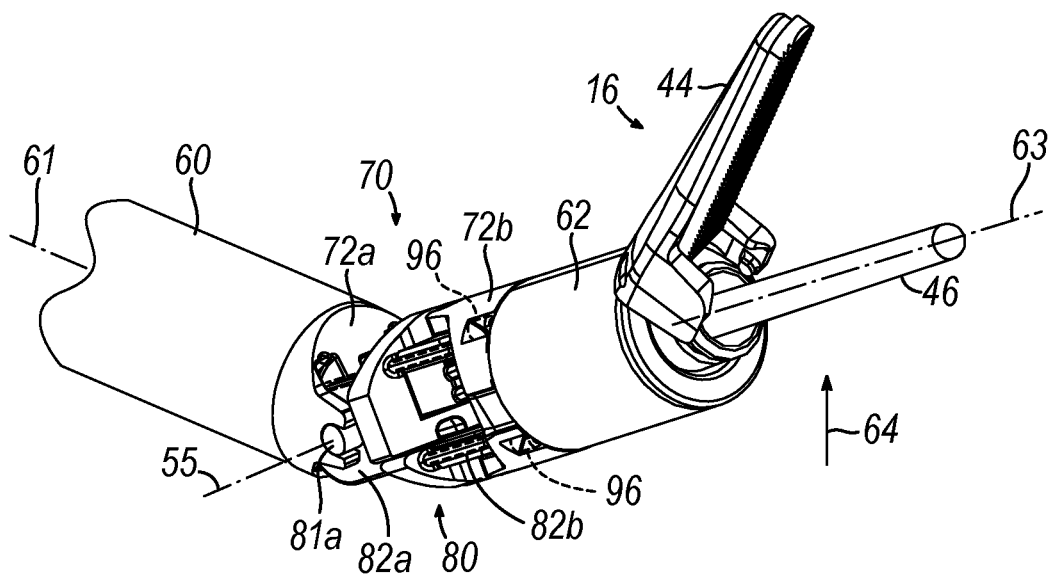
FIG. 5A depicts an enlarged perspective view of the surgical instrument of FIG. 1 with the end effector in an open position and the multi-planar articulation joint of FIG. 4 articulated about a first articulation axis in a first articulated configuration.
Figure 5B:
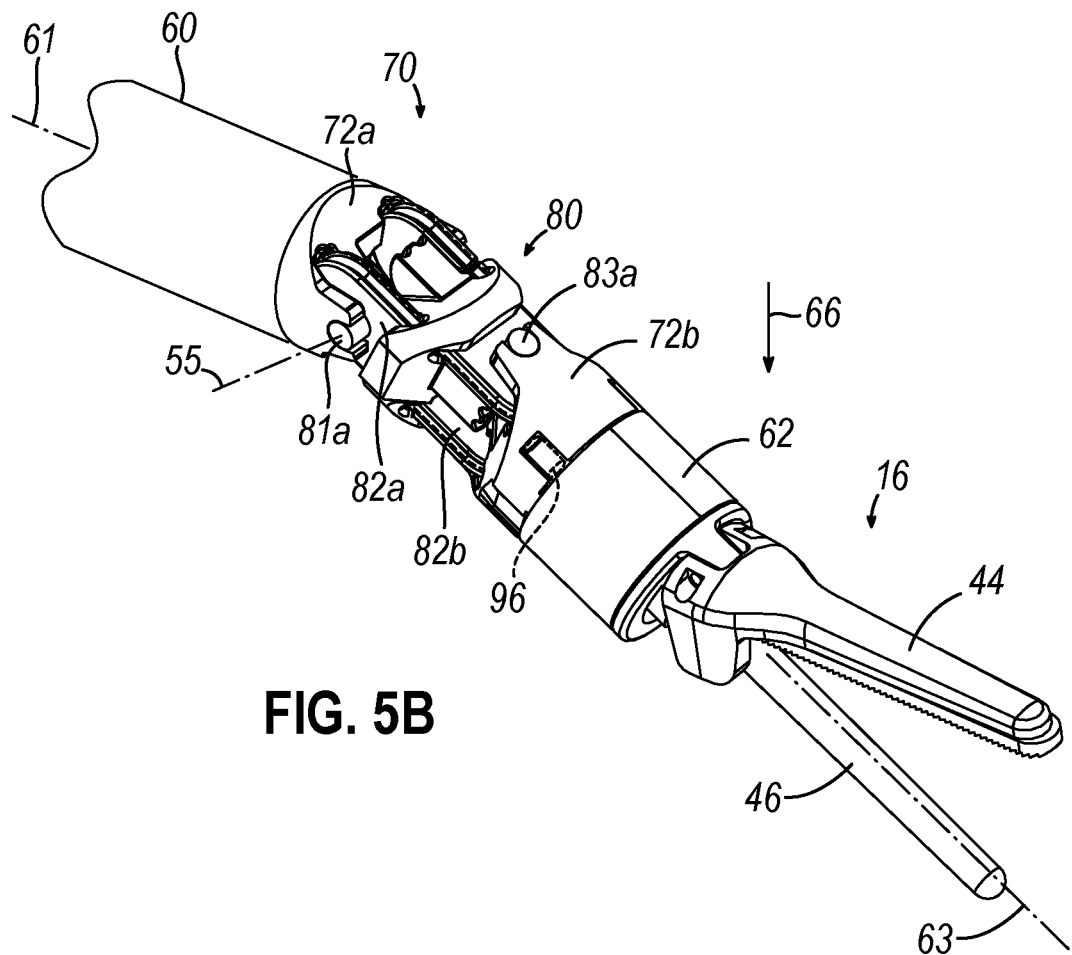
FIG. 5B depicts the enlarged perspective view of the surgical instrument similar to FIG. 5A, but with the multi-planar articulation joint articulated about the first articulation axis in a second articulated configuration.
Figure 6A:
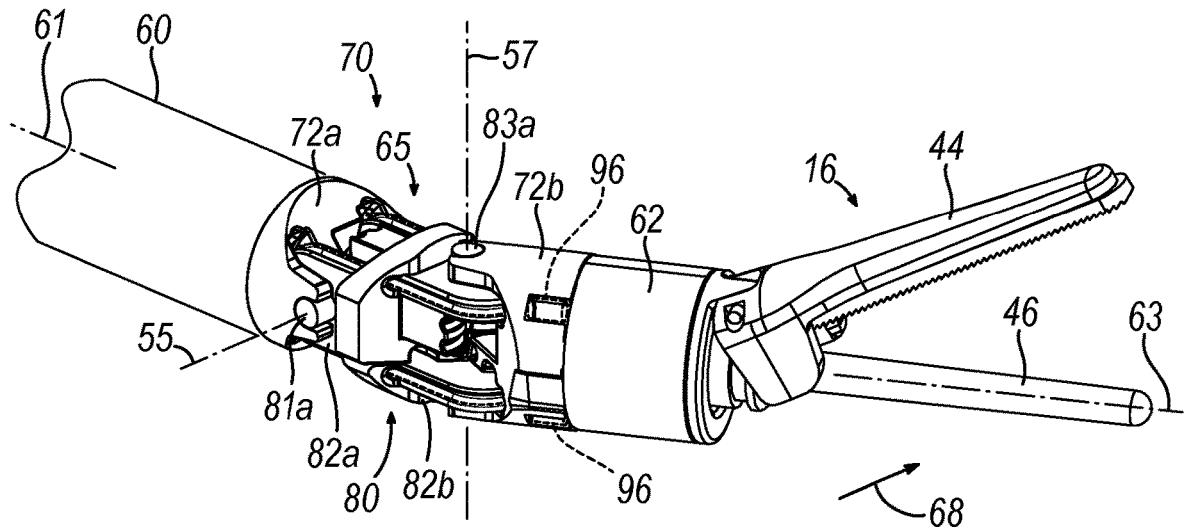
FIG. 6A depicts an enlarged perspective view of the surgical instrument of FIG. 1 with the end effector in an open position and the multi-planar articulation joint of FIG. 4 articulated about a second articulation axis in a first articulated configuration.
Figure 6B:
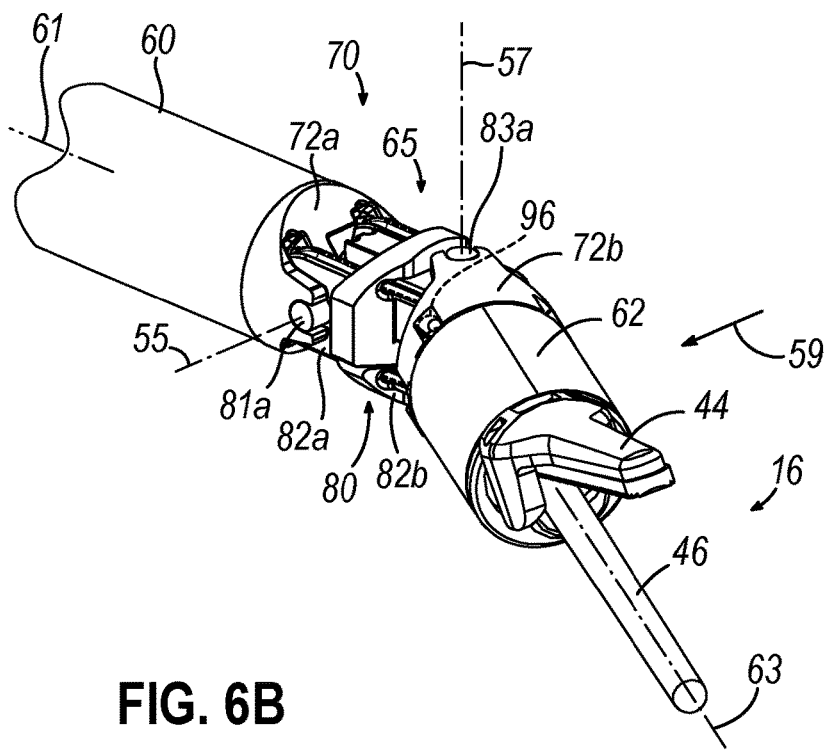
FIG. 6B depicts the enlarged perspective view of the surgical instrument similar to FIG. 6A, but with the distal articulation joint interface articulated about the second articulation axis in a second articulated configuration.

Referring to FIGS. 4-5B, articulation joint core (80) is pivotable relative to proximal articulation joint interface (72a) about a first articulation axis (55) extending transverse to longitudinal axis (61). Articulation joint core (80) is thereby pivotable about first articulation axis (55) to deflect end effector (16) upwardly along a first plane relative to longitudinal axis (61), as shown by arrow (64) in FIG. 5A, and/or downwardly along the first plane relative to longitudinal axis (61), as shown by arrow (66) in FIG. 5B. Referring to FIG. 4 and FIGS. 6A-6B, distal articulation joint interface (72b) is pivotable relative to articulation joint core (80) about a second articulation axis (57) extending transverse to both longitudinal axis (61) and first articulation axis (55). Distal articulation joint interface (72b) is thereby pivotable about second articulation axis (57) to deflect end effector (16) outwardly along a second plane relative to longitudinal axis (61), as shown by arrow (68) in FIG. 6A, and/or inwardly along the second plane relative to longitudinal axis (69), as shown by arrow (59) in FIG. 6B. Articulation joint core (80) and distal articulation joint interface (72b) may be articulated simultaneously or individually to deflect end effector (16) along the first and/or second planes as desired. Still other suitable articulation configurations for operating articulation section (70) will be apparent to one with ordinary skill in the art in view of the teachings herein. Articulation section (70) defines a centerline therethrough that similarly deflects to remain radially central within articulation section (70). In the present example, the centerline through articulation section (70) thus has a proximal portion that remains coaxial with longitudinal axis (61) and a distal portion that remains coaxial with distal shaft axis (65) regardless of the deflected or straight configurations available to multi-planar articulation joint (65).

In order to selectively drive such articulation about the first and second articulation axes (55, 57), a plurality of cables (96) extend from base assembly (12) (see FIG. 1) to multi-planar articulation joint (65). In the present example, proximal articulation joint interface (72a) is coupled with proximal shaft portion (60) and distal articulation joint interface (72b) is coupled with distal shaft portion (62). Four such cables (96) extend through openings (71a) of proximal articulation joint interface (72a), through corresponding channels (96a, 98a, 96b, 98b) and openings (97a, 97b) of articulation joint core (80), and through openings (71b) of distal articulation joint interface (72b). Cables (96) thereby connect to distal articulation joint interface (72b) such that pulling on cables (96) on one side of either first or second axes (55, 57) will selectively articulate multi-planar articulation joint (65). It will be appreciated that such cables (96) may be pulled in various combinations to achieve any desired articulation about first and second axes (55, 57). Still other suitable configurations for articulating multi-planar articulation joint (65) will be apparent to one with ordinary skill in the art in view of the teachings herein.

Figure 7:
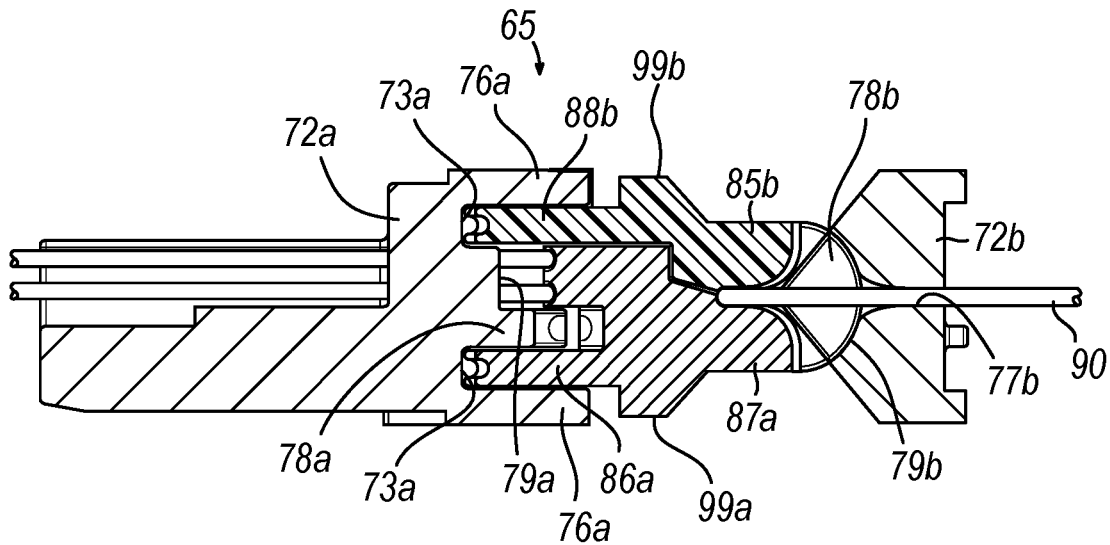
FIG. 7 depicts a cross-sectional top view of the articulation section of FIG. 4 taken along section line 7-7 of FIG. 4, showing the articulation joint having a lobe style connection.
Figure 8:
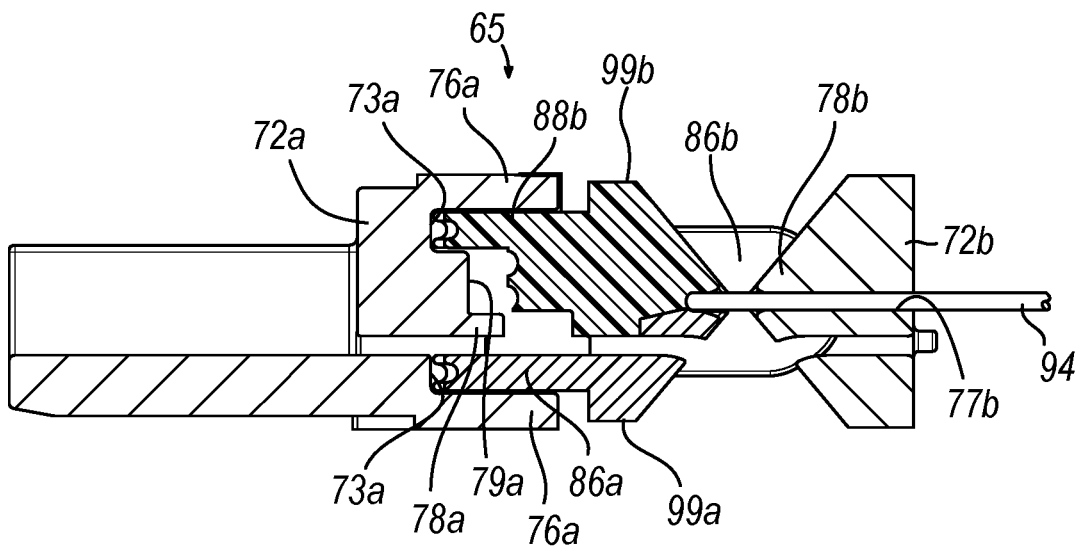
FIG. 8 depicts a cross-sectional top view of the articulation section of FIG. 4 taken along section line 8-8 of FIG. 4, showing the articulation joint having a wedge style connection.

Referring back to FIG. 4, multi-planar articulation joint (65) further provides support and guidance for elongate members (90, 92, 94) extending through articulation section (70) that may couple components of base assembly (12) (see FIG. 1) and/or shaft assembly (14) (see FIG. 1) with end effector (16) (see FIG. 1) for operation of end effector (16) (see FIG. 1). For instance, one or more elongate members (90, 92) may include cables acting in tension such that elongate member (90) may be used for pivoting upper jaw (44) into the closed position (see FIG. 3A) and elongate member (92) may be used for pivoting upper jaw (44) into the open position (see FIG. 3B). Accordingly, as shown in FIG. 7, articulation joint core (80) may be assembled to support such elongate members (90, 92) (see FIG. 4) in a lobe style configuration, as will be discussed in more detail below. Additionally or alternatively, one or more elongate members (94) may include a flexible control rod acting in compression and/or tension for pushing and/or pulling features within end effector (16) (see FIG. 3A). Accordingly, as shown in FIG. 8, multi-planar articulation joint (65) may be assembled to support such elongate members (94) in a wedge style configuration, as will be discussed in more detail below.

As shown in FIGS. 4 and 9-11, multi-planar articulation joint (65) supports each of elongate members (90, 94) along a continuous helical path to provide smooth control of elongate members (90, 94) that inhibits catching, kinking, over-extension, and/or over-compression of such elongate members (90, 94) during articulation of articulation section (70), particularly when simultaneously deflecting end effector (16) (see FIGS. 5A-6B) through multiple planes. In contrast, elongate member (92) extends along the centerline through proximal articulation joint interface (72a), articulation joint core (80), and distal articulation joint interface (72b) to be coaxial with axes (61, 63) while straight and deflected, such that elongate members (90, 94) are spirally positioned thereabout. To this end, multi-planar articulation joint (65) defines a plurality of lumens (91, 93, 95) for receiving and supporting elongate members (90, 92, 94). In the illustrated embodiment, elongate member (90) is positioned within lumen (91), elongate member (92) is positioned within lumen (93), and elongate member (94) is positioned within lumen (95). As with elongate members (90, 92, 94), each of lumens (91, 95) extend along a continuous helical path, whereas lumen (93) extends along the centerline through articulation joint core (80) such that lumens (91, 93, 95) are spirally positioned thereabout. While three elongate members (90, 92, 94) are shown in the present example, any other suitable number and/or configurations for elongate members (90, 92, 94) may be used.

Figure 9:
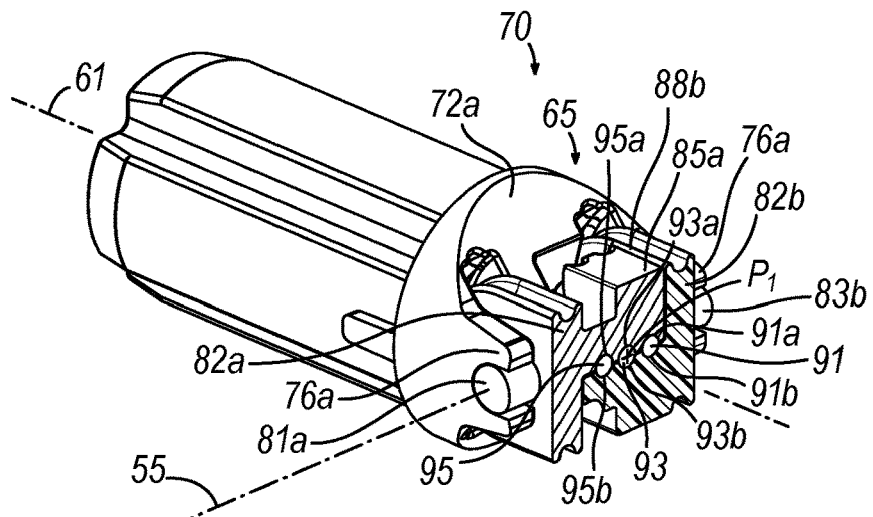
FIG. 9 depicts a cross-sectional side view of the articulation section of FIG. 4 taken along section line 9-9 of FIG. 4, showing the articulation joint defining a plurality of lumens oriented along the first articulation axis.
Figure 10:
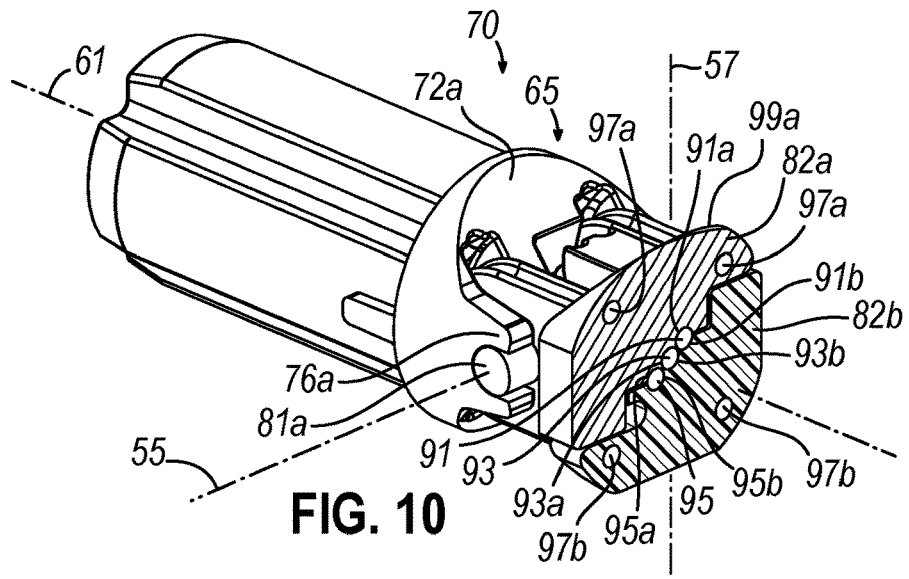
FIG. 10 depicts a cross-sectional side view of the articulation section of FIG. 4 taken along section line 10-10 of FIG. 4, showing the plurality of lumens of the articulation joint oriented obliquely between the first articulation axis and the second articulation axis.
Figure 11:
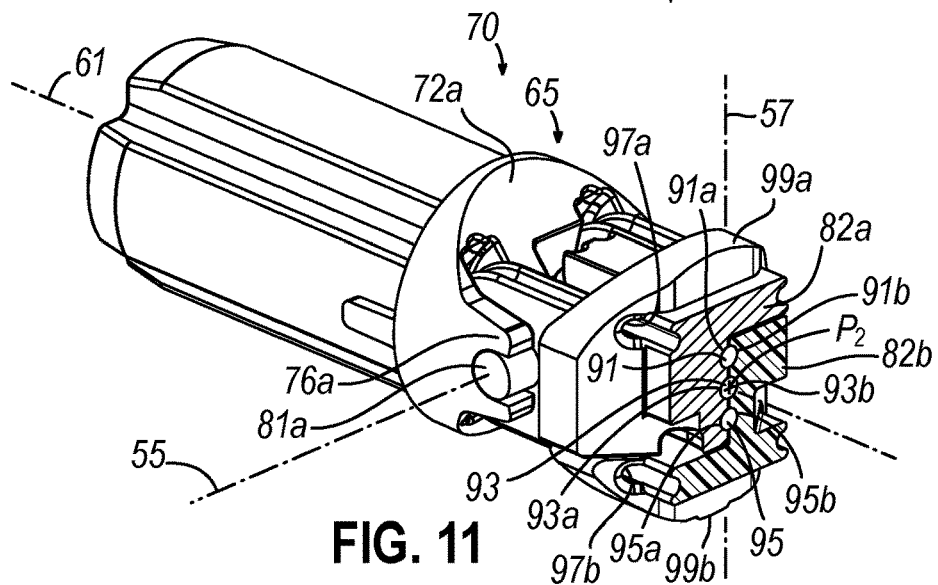
FIG. 11 depicts a cross-sectional side view of the articulation section of FIG. 4 taken along section line 11-11 of FIG. 4, showing the plurality of lumens of the articulation joint oriented along the second articulation axis.

Referring to FIG. 9, a proximal portion of multi-planar articulation joint (65) is configured to laterally align lumens (91, 93, 95) to be offset from each other along and intersect with first articulation axis (55). Accordingly, as multi-planar articulation joint (65) pivots about first articulation axis (55), elongate members (90, 92, 94) are positioned along first articulation axis (55) such that elongate members (90, 92, 94) may articulate about first articulation axis (55) with multi-planar articulation joint (65). Referring to FIG. 10, as elongate members (90, 92, 94) extend distally, lumens (91, 93, 95) support elongate members (90, 92, 94) within articulation section (70) to thereby laterally align elongate members (90, 92, 94) obliquely between first articulation axis (55) and second articulation axis (57). As elongate members (90, 92, 94) continue to extend distally, a distal portion of multi-planar articulation joint (65) is configured to laterally align lumens (91, 93, 95) to be offset from each other along second articulation axis (57), as shown in FIG. 11. Thus, as distal articulation joint interface (72b) pivots about second articulation axis (57), elongate members (90, 92, 94) are positioned along and intersect with second articulation axis (57) such that elongate members (90, 92, 94) may articulate about second articulation axis (57) with distal articulation joint interface (72b) (see FIG. 12). Multi-planar articulation joint (65) thereby supports elongate members (90, 92, 94) in a collective helical configuration to align elongate members (90, 92, 94) along the select articulation axis (55, 57) for supporting and guiding translation of elongate members (90, 92, 94) during articulation.

In some versions, multi-planar articulation joint (65) is configured to inhibit elongate members (90, 92, 94) from translating within multi-planar articulation joint (65). Referring to FIGS. 9 and 11, multi-planar articulation joint (65) is configured to maintain the spaced relationship between elongate members (90, 94) (see FIG. 4) at each articulation axis (55, 57) during articulation of articulation section (70). As shown in FIG. 9, multi-planar articulation joint (65) is positioned to align lumens (91, 93, 95) along first articulation axis (55) such that first articulation axis (55) intersects longitudinal axis (61) at first point ($P_1$) at a central lumen (93). One or more lumens (91, 95) are then each radially offset from first point ($P_1$) at a predetermined distance. Accordingly, multi-planar articulation joint (65) maintains this radial space between the one or more lumens (91, 95) and first point ($P_1$) at the predetermined distance as articulation section (70) is deflected from a straight configuration with articulation section (70) aligned along longitudinal axis (61) to a deflected configuration with articulation section (70) pivoted about first articulation axis (55) to deflect end effector (16) upwardly and/or downwardly along the first plane relative to longitudinal axis (61) (see FIGS. 5A-5B). As shown in FIG. 11, multi-planar articulation joint (65) is positioned to align lumens (91, 93, 95) along second articulation axis (57) such that second articulation axis (57) intersects longitudinal axis (61) at second point ($P_2$) at central lumen (93). One or more lumens (91, 95) are then each radially offset from second point ($P_2$) at a predetermined distance. Accordingly, multi-planar articulation joint (65) maintains this radial space between the one or more lumens (91, 95) and second point ($P_2$) at the predetermined distance as articulation section (70) is deflected from a straight configuration with articulation section (70) aligned along longitudinal axis (61) to a deflected configuration with articulation section (70) pivoted about second articulation axis (57) to deflect end effector (16) outwardly and/or inwardly along the second plane relative to longitudinal axis (61) (see FIGS. 6A-6B). With elongate members (90, 92, 94) (see FIG. 4) positioned through lumens (91, 93, 95), multi-planar articulation joint (65) is thereby configured to maintain the radially spaced relationship between elongate members (90, 92, 94) (see FIG. 30) at each articulation axis (55, 57) during articulation of articulation section (70).

Figure 12:
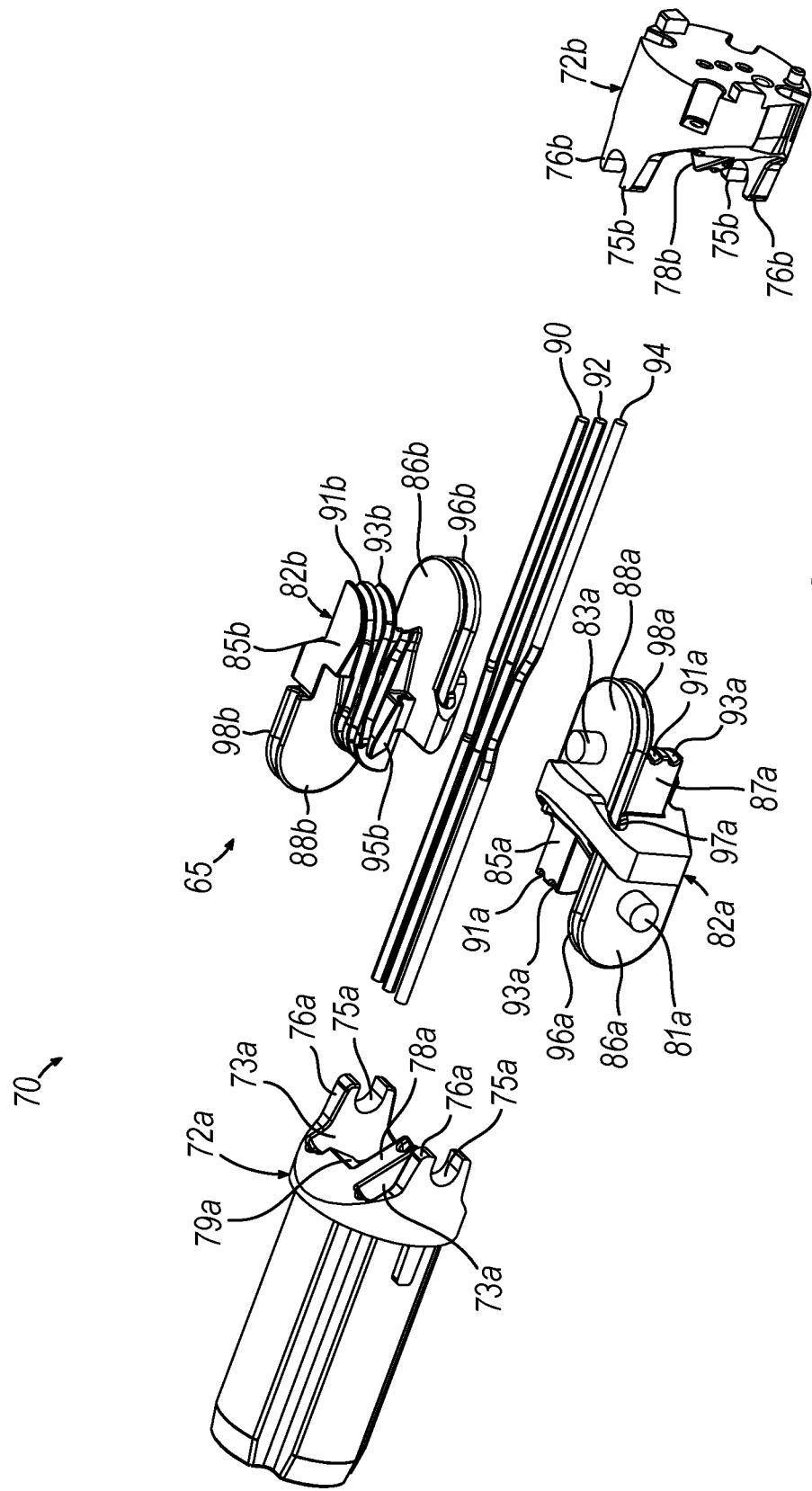
FIG. 12 depicts an exploded perspective view of the articulation section of FIG. 4.
Figure 13:
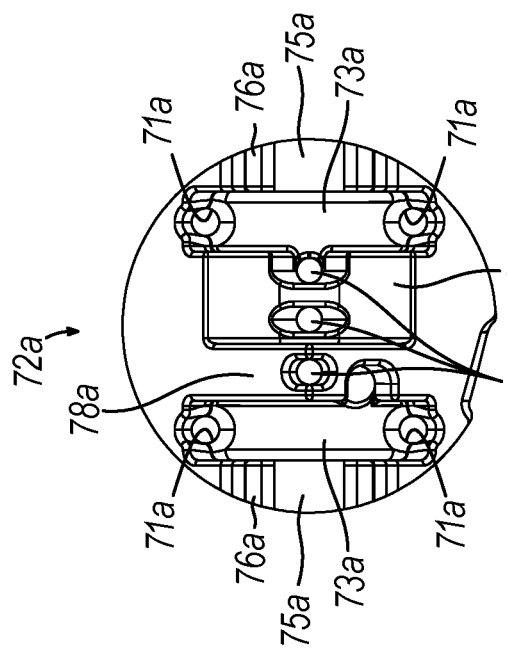
FIG. 13 depicts a perspective view of a proximal articulation joint interface of the articulation section of FIG. 4.
Figure 14:
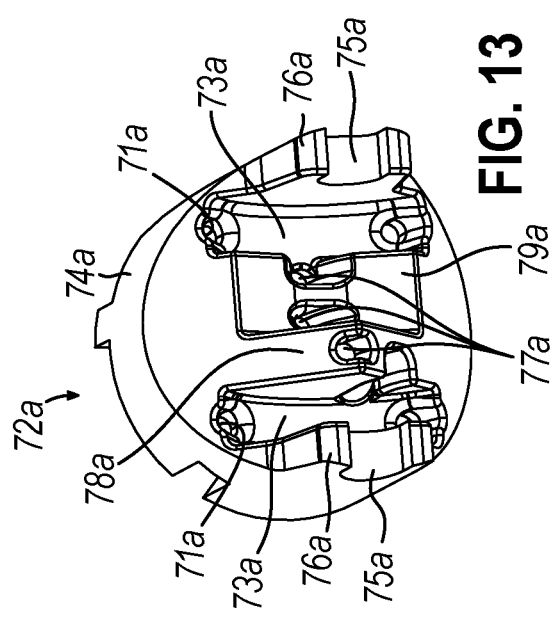
FIG. 14 depicts a side elevational view of the proximal articulation joint interface of FIG. 13.
Figure 15:
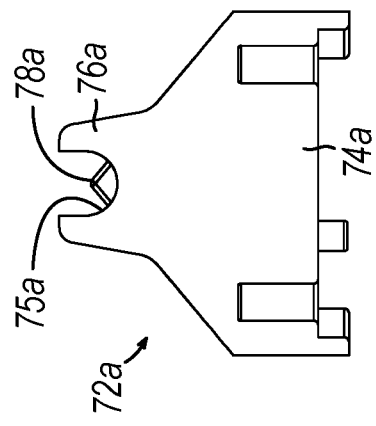
FIG. 15 depicts a top plan view of the proximal articulation joint interface of FIG. 13.
Figure 16:
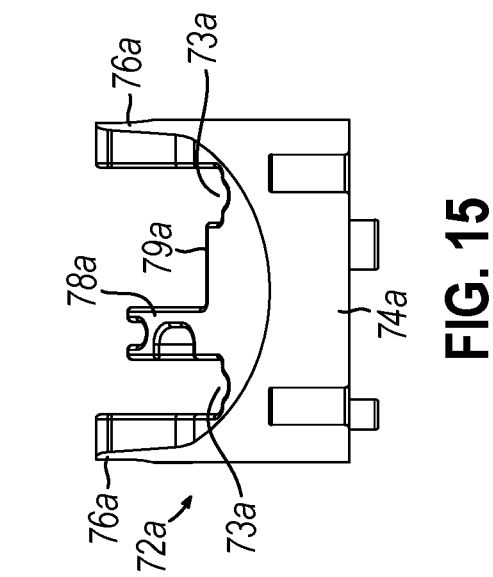
FIG. 16 depicts a front view of the proximal articulation joint interface of FIG. 13.
Figure 18:
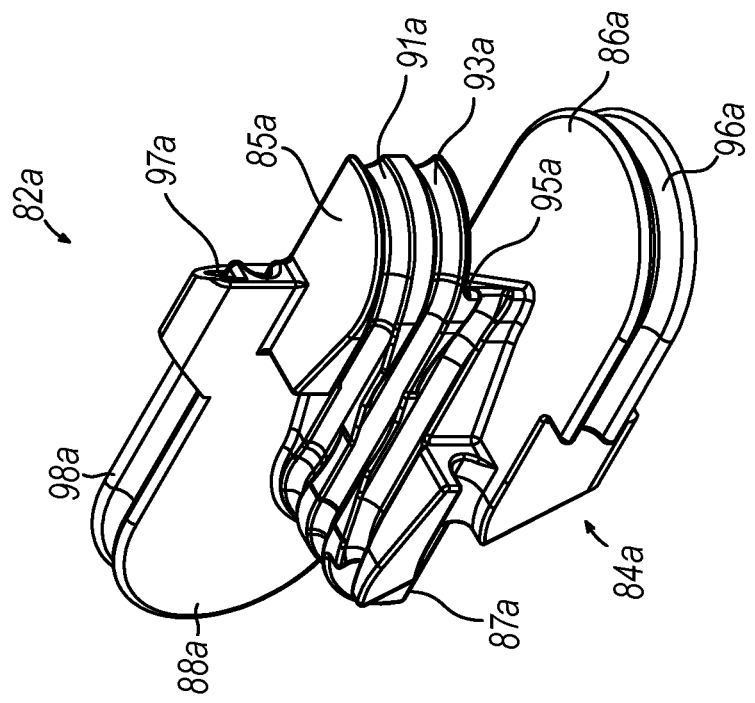
FIG. 18 depicts a bottom perspective view of the articulation joint member of FIG. 17.
Figure 17:
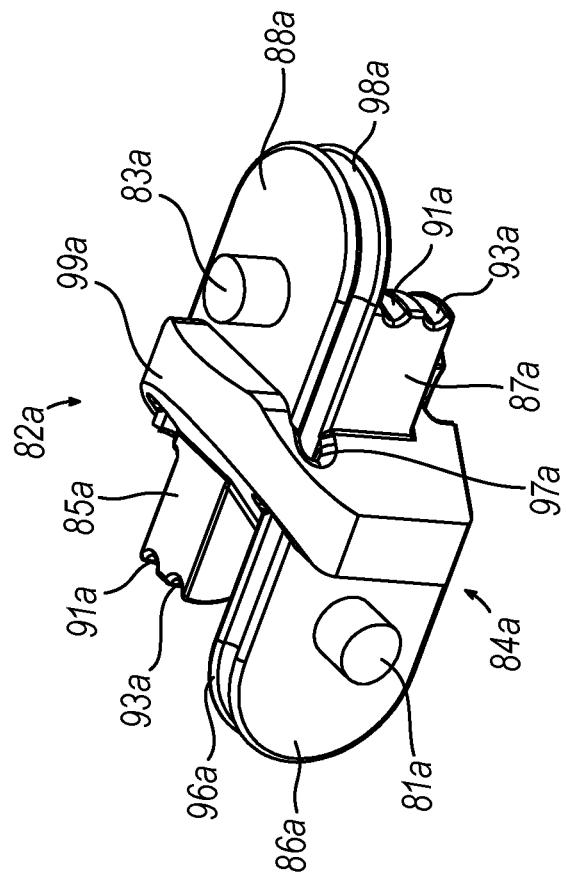
FIG. 17 depicts a top perspective view of an articulation joint member of the multi-planar articulation joint of FIG. 4.
Figure 19:
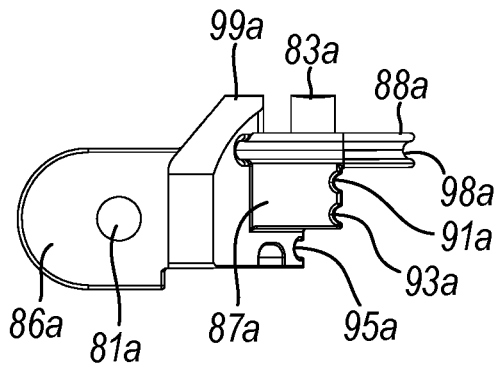
FIG. 19 depicts a front view of the articulation joint member of FIG. 17.
Figure 20:
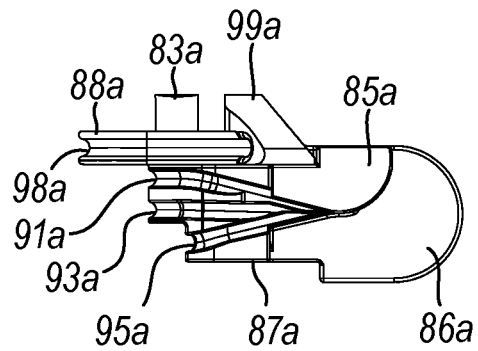
FIG. 20 depicts a rear view of the articulation joint member of FIG. 17.
Figure 21:
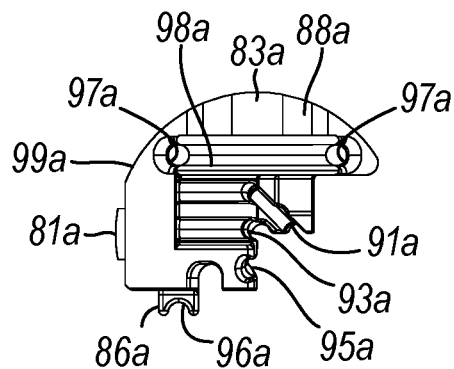
FIG. 21 depicts a right side elevational view of the articulation joint member of FIG. 17.
Figure 22:
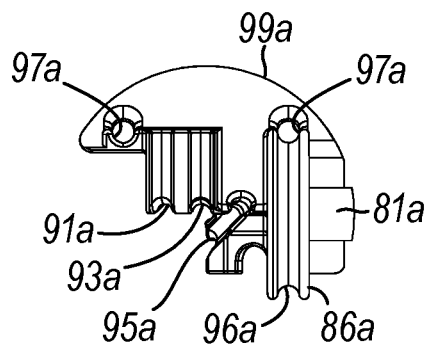
FIG. 22 depicts a left side elevational view of the articulation joint member of FIG. 17.
Figure 23:
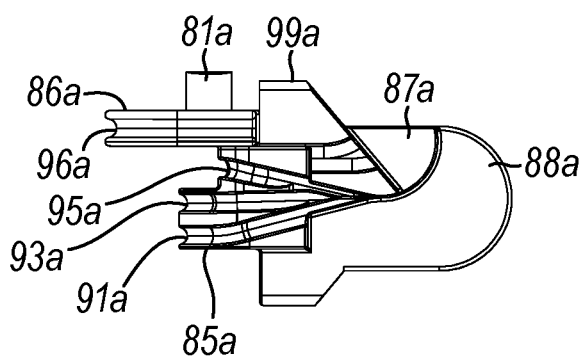
FIG. 23 depicts a bottom plan view of the articulation joint member of FIG. 17.
Figure 24:
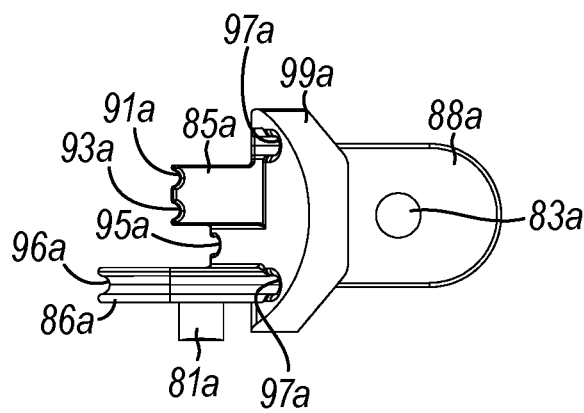
FIG. 24 depicts a top plan view of the articulation joint member of FIG. 17.

FIG. 12 shows multi-planar articulation joint (65) in more detail. As shown in the present example, distal articulation joint interface (72b) is similar to proximal articulation joint interface (72a), but is positioned in a reversed direction and orientated about 90 degrees clockwise relative to proximal articulation joint interface (72a). Second articulation joint member (82b) is also similar to first articulation joint member (82a), but is positioned in a reversed direction and oriented about 90 degrees clockwise relative to first articulation joint member (82a). Accordingly, multi-planar articulation joint (65) is configured to support elongate members (90, 92, 94) to spiral in shape about 90 degrees in the collective helical configuration from a relatively horizontal orientation to a relatively vertical orientation through multi-planar articulation joint (65), but any other suitable angles for accommodating various deflections may be similarly used. While proximal articulation joint interface (72a) and first articulation joint member (82a) are discussed in more detail below, it should be noted that the discussion also applies to distal articulation joint interface (72b) and second articulation joint member (82b) respectively such that a like number with a differing letter indicates a like feature.

FIGS. 13-16 show proximal articulation joint interface (72a) comprising a generally cylindrical body (74a) having a pair of arms (76a) extending outwardly from body (74a) on opposing sides of body (74a). Each arm (76a) includes an arcuate recess (75a) extending inwardly within arm (76a). Body (74a) further includes a pair of channels (73a) extending inwardly within body (74a) adjacent to each arm (76a) on opposing sides of body (74a). Each channel (73a) is curved and includes an opening (71a) extending through a top and bottom portion of each channel (73a). Body (74a) further comprises a protrusion (78a) extending outwardly from body (74a) adjacent to respective channel (73a). In the present example, protrusion (78a) has a generally triangular shape, but any other suitable shape may be used. A curved indentation (79a) is then positioned between protrusion (78a) and the opposing channel (73a) on body (74a). A plurality of conduits (77a) extend longitudinally through a central portion of body (74a) such that conduits (77a) are aligned with recesses (75a) of arms (76a). As shown in the present example, one conduit (77a) is positioned through protrusion (78a) and the remaining two conduits (77a) are positioned through indentation (79a).

FIGS. 17-24 show first articulation joint member (82a) comprising a body (84a) having a collar (99a) positioned about a central portion of body (84a). Body (84a) comprises a first plate (86a) extending outwardly from collar (99a) and a second plate (88a) extending outwardly from collar (99a) in an opposing direction from first plate (86a). First plate (86a) is generally elliptical and defines a channel (96a) extending within first plate (86a) about a circumference of first plate (86a). A generally cylindrical knob (81a) extends outwardly from an exterior surface of first plate (86a). Second plate (88a) is generally elliptical and defines a channel (98a) extending within second plate (88a) about a circumference of second plate (88a). A generally cylindrical knob (83a) extends outwardly from an exterior surface of second plate (88a). Second plate (88a) is oriented about 90 degrees clockwise relative to first plate (86a) such that an end of channel (98a) of second plate (88a) is aligned with an end of channel (96a) of first plate (86a). An opening (97a) is then positioned through collar (99a) to connect channel (98a) of second plate (88a) with channel (96a) of first plate (98a).

Figure 25:
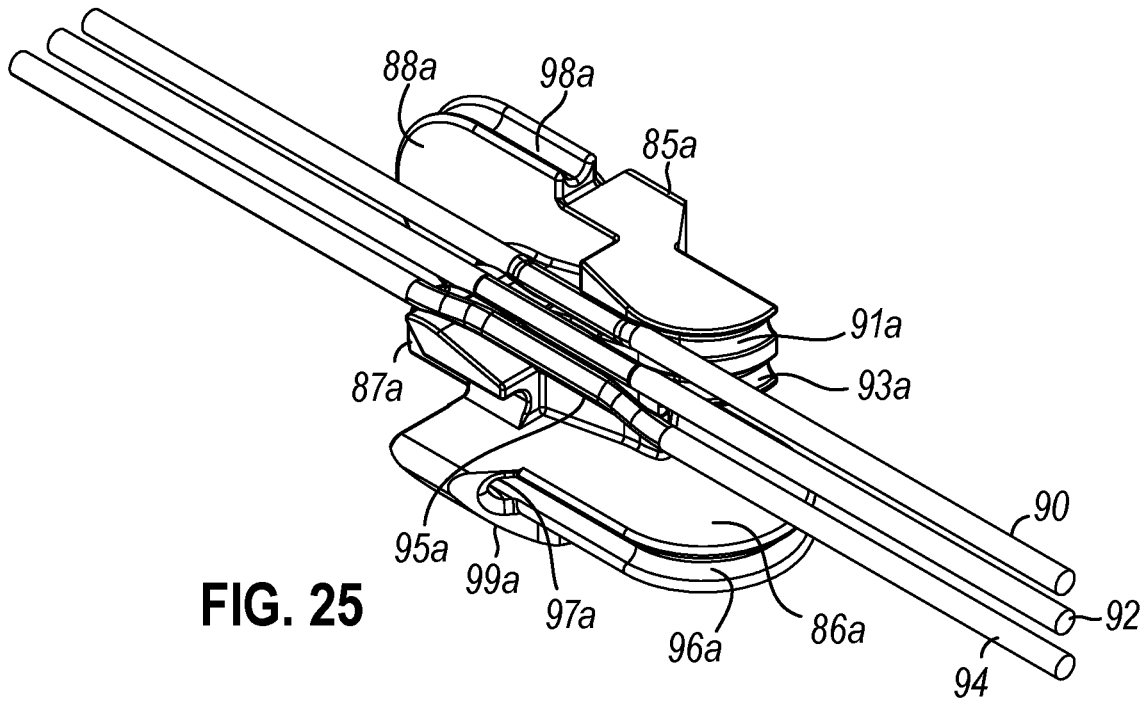
FIG. 25 depicts a bottom perspective view of the articulation joint member of FIG. 17, showing a plurality of elongate members positioned within the proximal articulation joint.
Figure 26:
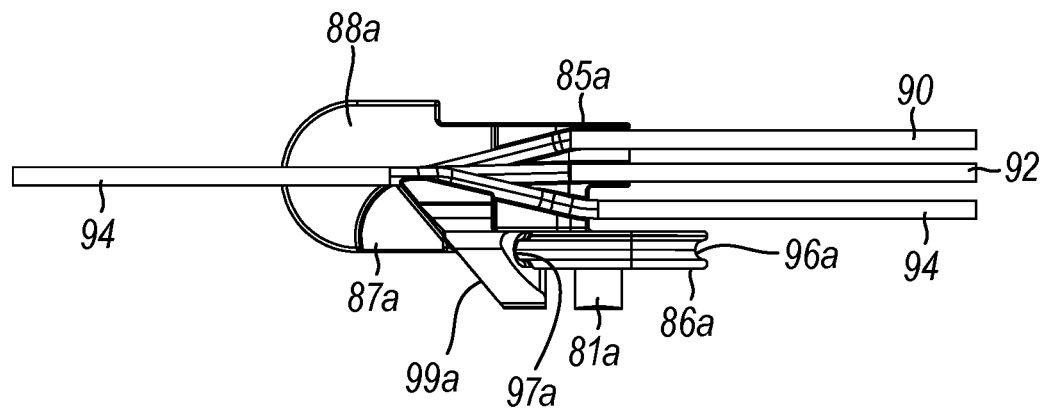
FIG. 26 depicts a rear view of the articulation joint member of FIG. 25.

Body (84a) of first articulation joint member (82a) further comprises a first protrusion (85a) extending inwardly from an interior surface of first plate (86a) and a second protrusion (87a) extending inwardly from an interior surface of second plate (88a). Second protrusion (87a) is oriented about 90 degrees clockwise relative to first protrusion (85a) such that second protrusion (87a) is connected with first protrusion (85a) at a central portion of body (84a). Each protrusion (85a, 87a) has a curved end portion. Collar (99a) defines a wedge portion between first protrusion (85a) and first plate (86a). A plurality of channels (91a, 93a, 95a) extend continuously from the end portion of first protrusion (85a) to the end portion of second protrusion (87a). As each channel (91a, 93a, 95a) extends from first protrusion (85a) to second protrusion (87a), each channel (91a, 95a) spirals around channel (93a) along the centerline therethrough about 90 degrees. Accordingly, channels (91a, 93a, 95a) are aligned horizontally relative to each other on first protrusion (85a) and are aligned vertically relative to each other on second protrusion (87a). Channels (91a, 93a, 95a) of articulation joint member (82a) are thereby configured to receive elongate members (90, 92, 94), as shown in FIGS. 25-26. Each channel (91a, 93a, 95a) receives an elongate member (90, 92, 94). Elongate members (90, 94) thereby spiral about 90 degrees around elongate member (92) through channels (91a, 93a, 95a) such that elongate members (90, 92, 94) are aligned horizontally relative to each other on first protrusion (85a) and are aligned vertically relative to each other on second protrusion (87a).

Figure 28:
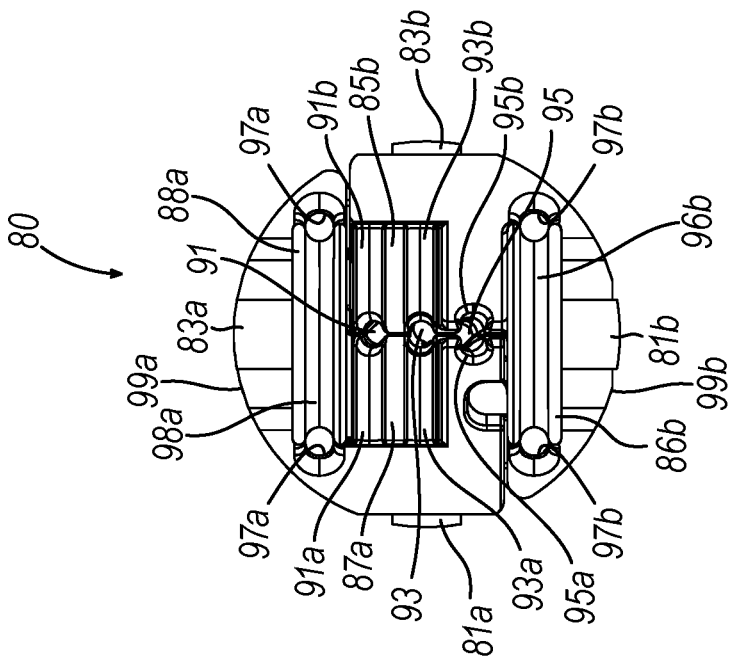
FIG. 28 depicts a side elevational view of the articulation joint core of FIG. 27.
Figure 27:
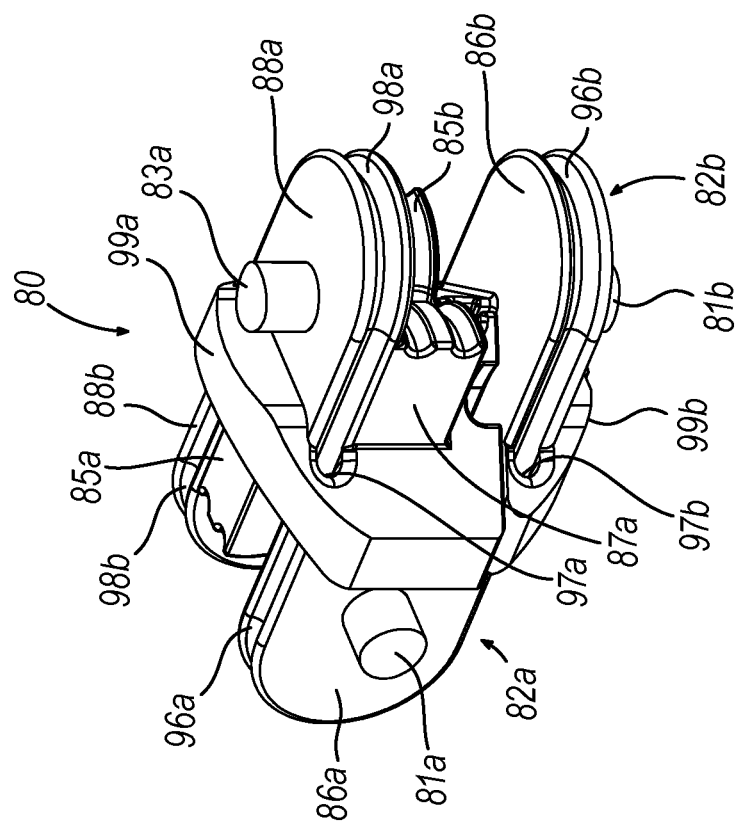
FIG. 27 depicts a perspective view of an articulation joint core of the articulation section of FIG. 4.

FIGS. 27-28 show first articulation joint member (82a) assembled with second articulation joint member (82b) to form articulation joint core (80). As shown, second articulation joint member (82b) is oriented in an opposing direction and reoriented about 90 degrees clockwise relative to first articulation joint member (82a). This aligns first protrusion (85b) of second articulation joint member (82b) with second protrusion (87a) of first articulation joint member (82a). Accordingly, channel (91a) of first articulation joint member (82a) is aligned with channel (91b) of second articulation joint member (82b) to form lumen (91). Channel (93a) of first articulation joint member (82a) is aligned with channel (93b) of second articulation joint member (82b) to form lumen (93). Channel (95a) of first articulation joint member (82a) is aligned with channel (95b) of second articulation joint member (82b) to form lumen (95). Channel (96a) of first articulation joint member (82a) is also aligned with channel (96b) of second articulation joint member (82b) and channel (98a) of first articulation joint member (82a) is also aligned with channel (98b) of second articulation joint member (82b) such that channels (96a, 96b, 98a, 98b) extend continuously about a perimeter of articulation joint core (80).

Referring to FIGS. 4-28, articulation joint core (80) is assembled with proximal and distal articulation joint interfaces (72a, 72b) such that proximal articulation joint interface (72a) is coupled proximally to articulation joint core (80) and distal articulation joint interface (72b) is coupled distally to distal articulation joint core (80). For instance, a knob (81a) of first articulation joint member (82a) is inserted within recess (75a) of proximal articulation joint interface (72a) and knob (83b) of second articulation joint member (82b) is inserted within the opposing recess (75a) of proximal articulation joint interface (72a). Knobs (81a, 83b) are rotatable within recesses (75a) to thereby allow articulation joint core (80) to pivot relative to proximal articulation joint interface (72a) about first articulation axis (55). First plate (86a) of first articulation joint member (82a) is inserted within channel (73a) of proximal articulation joint interface (72a) and second plate (88b) of second articulation joint member (82b) within the opposing channel (73a) of proximal articulation joint interface (72a). Openings (71a) of proximal articulation joint interface (72a) are thereby aligned with channel (96a) of first articulation joint member (82a) and channel (98b) of second articulation joint member (82b). The curved configurations of plates (86a, 88b) and channels (73a) allow plates (86a, 88b) of articulation joint core (80) to rotate smoothly within channels (73a) as articulation joint core (80) is pivoted about first articulation axis (55). First protrusion (85a) of first articulation joint member (82a) and second protrusion (87b) of second articulation joint member (82b) are inserted within indentation (79a) of proximal articulation joint interface (72a) and protrusion (78a) of proximal articulation joint interface (72a) is inserted between first protrusion (85a) and first plate (86a) of first articulation joint member (82a). Accordingly, conduits (77a) of proximal articulation joint interface (72a) are aligned to further define lumens (91, 93, 95) extending through articulation joint core (80).

On the distal end portion of articulation joint core (80), knob (83a) of first articulation joint member (82a) is inserted within recess (75b) of distal articulation joint interface (72b) and knob (81b) of second articulation joint member (82b) is inserted within the opposing recess (75b) of distal articulation joint interface (72b). Knobs (81b, 83a) are rotatable within recesses (75b) to thereby allow distal articulation joint interface (72b) to pivot relative to articulation joint core (80) about second articulation axis (57). Second plate (88a) of first articulation joint member (82a) is inserted within channel (73b) of distal articulation joint interface (72b) and first plate (86b) of second articulation joint member (82b) within the opposing channel (73b) of distal articulation joint interface (72b). Openings (71b) of distal articulation joint interface (72b) are thereby aligned with channel (98a) of first articulation joint member (82a) and channel (96b) of second articulation joint member (82b). The curved configurations of plates (86b, 88a) and channels (73b) allow plates (86b, 88a) of articulation joint core (80) to rotate smoothly within channels (73b) as distal articulation joint interface (72b) is pivoted about second articulation axis (57). First protrusion (85b) of second articulation joint member (82b) and second protrusion (87a) of first articulation joint member (82a) are inserted within indentation (79b) of distal articulation joint interface (72b) and protrusion (78b) of distal articulation joint interface (72b) is inserted between first protrusion (85b) and first plate (86b) of second articulation joint member (82b). Accordingly, conduits (77b) of distal articulation joint interface (72b) are aligned to further define lumens (91, 93, 95) extending through articulation joint core (80).

Elongate members (90, 92, 94) are respectively positioned through conduits (77a) of proximal articulation joint interface (72a), through lumens (91, 93, 95) of articulation joint core (80), and through conduits (77b) of distal articulation joint interface (72b) to operatively connect elongate members (90, 92, 94) with end effector (16) for operation of end effector (16). As elongate members (90, 92, 94) distally extend through articulation joint core (80), elongate members (90, 92, 94) are oriented along first articulation axis (55) and elongate members (90, 94) spiral around elongate member (92) to be collectively oriented along second articulation axis (57) via the collective helical configuration of lumens (91, 93, 95). Referring to FIG. 7, the curved end portions of first protrusion (85b) of second articulation joint member (82b) and second protrusion (87a) of first articulation joint member (82a) are aligned at elongate members (90, 92) proximal to distal articulation joint interface (72b) to support such elongate members (90, 92) in a lobe style configuration. This may allow for distributed articulation of elongate members (90, 92) between articulation joint core (80) and distal articulation joint interface (72b). The curved end portions of first protrusion (85a) of first articulation joint member (82a) and second protrusion (87b) of second articulation joint member (82b) may also be aligned at elongate members (90, 92) distal to proximal articulation joint interface (72a) to support such elongate members (90, 92) in a lobe style configuration. Referring to FIG. 8, the wedge portions of collars (99a, 99b) of first and second articulation joint members (82a, 82b) are aligned at elongate member (94) proximal to distal articulation joint interface (72b) to support such elongate member (94) in a wedge style configuration. This may allow for a more concentrated articulation of elongate member (94) between articulation joint core (80) and distal articulation joint interface (72b). The wedge end portions of collars (99a, 99b) may also be aligned at elongate member (94) distal to proximal articulation joint interface (72a) to support such elongate member (94) in a wedge style configuration.

By way of example only, articulation section (64) may alternatively or additionally be configured in accordance with one or more teachings of U.S. Pat. No. 9,402,682, entitled "Articulation Joint Features for Articulating Surgical Device," issued Aug. 2, 2016, the disclosure of which is incorporated by reference herein. As another merely illustrative example, articulation section (64) may alternatively or additionally be configured in accordance with one or more teachings of U.S. Pat. No. 9,393,037, issued Jul. 19, 2016, entitled "Surgical Instruments with Articulating Shafts," the disclosure of which is incorporated by reference herein and U.S. Pat. No. 9,095,367, issued Aug. 4, 2015, entitled "Flexible Harmonic Waveguides/Blades for Surgical Instruments," the disclosure of which is incorporated by reference herein. In addition to or in lieu of the foregoing, articulation section (64) and/or may be constructed and/or operable in accordance with at least some of the teachings of U.S. Pat. No. 10,034,683, entitled "Ultrasonic Surgical Instrument with Rigidizing Articulation Drive Members," issued on Jul. 31, 2018. Alternatively, articulation section (64) may be constructed and/or operable in any other suitable fashion.

Figure 29:
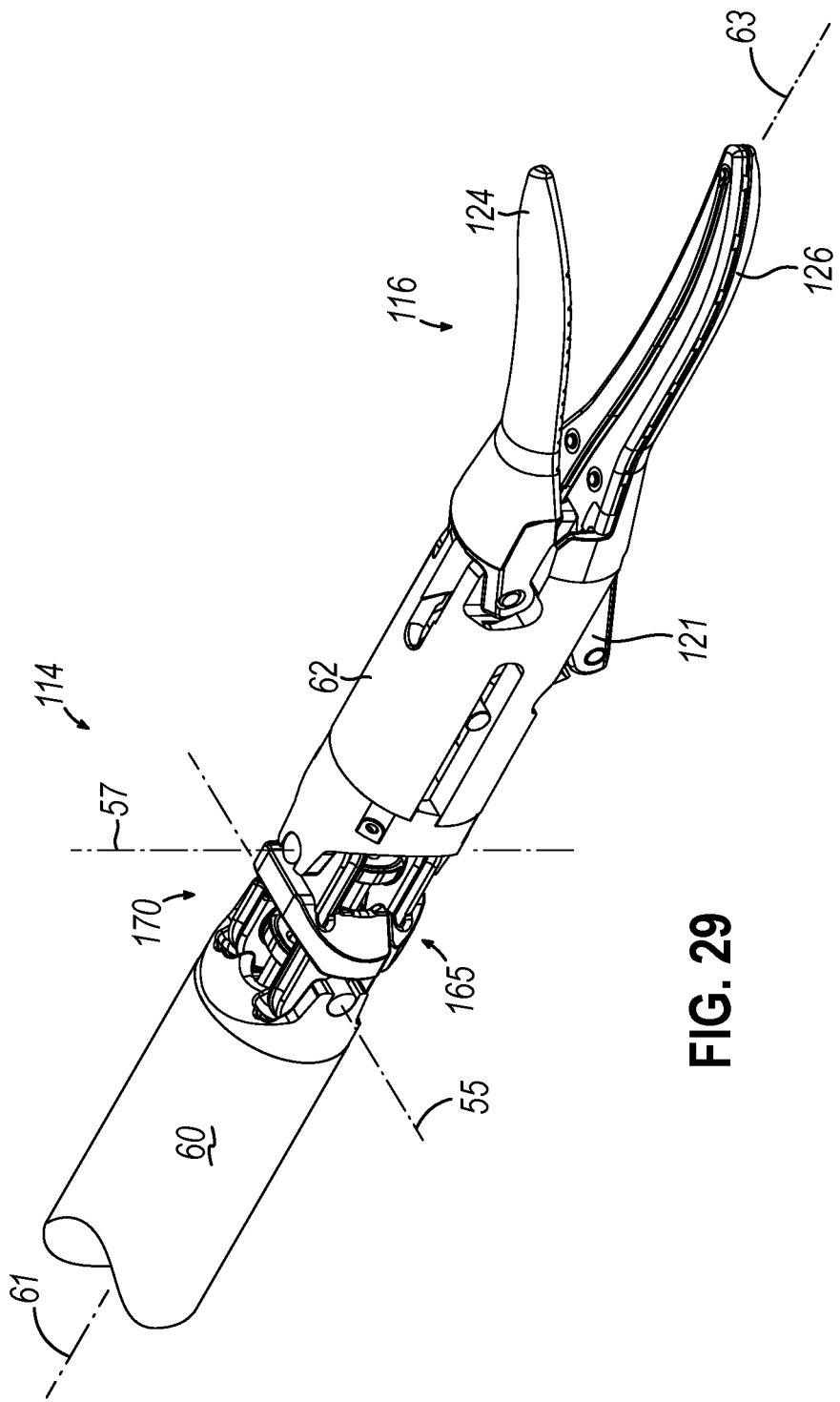
FIG. 29 depicts a perspective view of an alternative end effector and an alternative shaft assembly for use with the base assembly of FIG. 1, the shaft assembly having an articulation section with a second exemplary multi-planar articulation joint.

D. Alternative Exemplary End Effector and Shaft Assembly Having an Articulation Section with a Second Exemplary Multi-Planar Articulation Joint FIG. 29 shows an alternative end effector (116) and shaft assembly (114) for use with base assembly (12) (see FIG. 1) described above such that like numbers below indicate like features described above in greater detail. End effector (116) of the present example is similar to end effector (16) (see FIG. 1) described above in that end effector (116) includes an upper jaw (124) and a lower jaw (126) for clamping tissue. In the illustrated embodiment, upper jaw (124) is operable to selectively pivot toward and away from lower jaw (126) to selectively clamp tissue between upper jaw (124) and lower jaw (126). A pair of arms (121) extend transversely from upper jaw (124) and are pivotally secured to another portion of shaft assembly (114) configured to longitudinally slide to pivot upper jaw (124) between a closed position and an open position. End effector (116) of the present example is operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

While the present example of end effector (116) includes jaws (124, 126) configured to grip tissue for manipulation thereof, it will be appreciated that any such end effector for use with tissue in a surgical procedure may be similarly incorporated into surgical instrument (10) (see FIG. 1). Indeed, other suitable configurations for end effector will be apparent to one with ordinary skill in the art in view of the teachings herein, including, but not limited to, an endocutter, grasper, cutter, stapler, clip applier, access device, needle driver, scissors, retractor, spatula, hook, and energy delivery device using ultrasonic vibration, RF, laser, etc. The invention is thus not intended to be limited to end effector (116) shown in the present example.

More particularly, and by way of example only, end effector (116) may alternatively or additionally be configured in accordance with one or more teachings described in U.S. Pat. Pub. No. 2019/0125464, entitled "Robotic Surgical Tool with Manual Release Lever," published on May 2, 2019, issued as U.S. Pat. No. 10,624,709; U.S. Pat. Pub. No. 2012/0292367, entitled "Robotically-Controlled End Effector," published on Nov. 11, 2012, now abandoned; U.S. Pat. No. 9,314,308, entitled "Robotic Ultrasonic Surgical Device With Articulating End Effector," issued on Apr. 19, 2016; and U.S. Pat. No. 10,039,548, entitled "Clip Applier Adapted for Use with a Surgical Robot," issued on Aug. 7, 2018.

Figure 30:
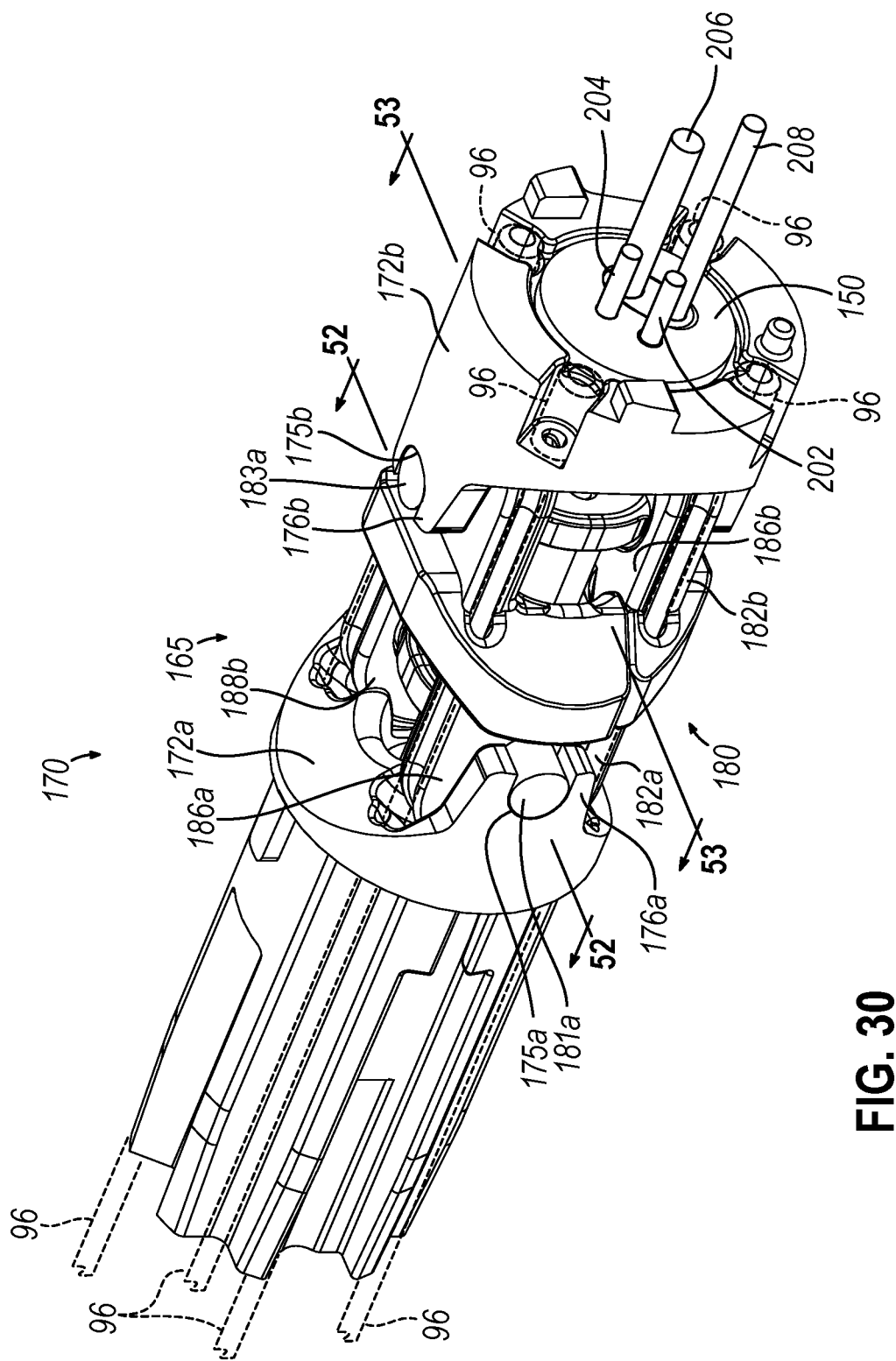
FIG. 30 depicts a perspective view of the articulation section of FIG. 29.

Shaft assembly (114) of the present example includes an alternative exemplary articulation section (170) having a second exemplary multi-planar articulation joint (165) configured to deflect end effector (116) through a plurality of planes. Referring to FIGS. 29-30, multi-planar articulation joint (165) includes a proximal articulation joint interface (172a) extending distally from proximal shaft portion (60) a distal articulation joint interface (172b) extending proximally from distal shaft portion (62), and an articulation joint core (180) positioned between proximal and distal articulation joint interfaces (172a, 172b). Articulation joint core (180) includes a first articulation joint member (182a) assembled with a second articulation joint member (182b) such that second articulation joint member (182b) is oriented about 90 degrees clockwise relative to first articulation joint member (182a) about longitudinal axis (61). Each of first and second articulation joint members (182a, 182b) are thereby assembled to form articulation joint core (180), which is pivotable relative to longitudinal axis (61) of proximal shaft portion (60) to position end effector (116) in various positions about longitudinal axis (61) similar to articulation joint core (80) described above.

In order to selectively drive multi-planar articulation joint (165), a plurality of cables (96) extend from base assembly (12) (see FIG. 1) to multi-planar articulation joint (165). In the present example, proximal articulation joint interface (172a) is coupled with proximal shaft portion (60) and distal articulation joint interface (172b) is coupled with distal shaft portion (62). Four such cables (96) extend through openings (171a) of proximal articulation joint interface (172a), through corresponding channels (196a, 198a, 196b, 198b) (see FIGS. 47-48) and openings (197a, 197b) (see FIGS. 47-48) of articulation joint core (180), and through openings (171b) of distal articulation joint interface (172b). Cables (96) thereby connect to distal articulation joint interface (172b) such that pulling on cables (96) on one side of multi-planar articulation joint (165) will selectively articulate multi-planar articulation joint (165). It will be appreciated that such cables (96) may be pulled in various combinations to achieve any desired articulation. Still other suitable configurations for articulating multi-planar articulation joint (165) will be apparent to one with ordinary skill in the art in view of the teachings herein.

With respect to FIG. 30, multi-planar articulation joint (165) further provides support and guidance for elongate members (202, 204, 206, 208) extending through articulation section (170) that may couple components of base assembly (12) (see FIG. 1) and/or shaft assembly (114) (see FIG. 29) with end effector (116) (see FIG. 29) for operation of end effector (116) (see FIG. 29). For instance, one or more elongate members (202, 204) may include cables acting in tension such that elongate member (202) may be used for pivoting upper jaw (124) into the closed position and elongate member (204) may be used for pivoting upper jaw (124) into the open position. Additionally, elongate member (206) may be configured to provide RF energy to end effector (116) and elongate member (208) may be configured as a knife rod for cutting tissue grasped within end effector (116). Still other suitable configurations for elongate members (202, 204, 206, 208) will be apparent to one with ordinary skill in the art in view of the teachings herein.

Figure 31:
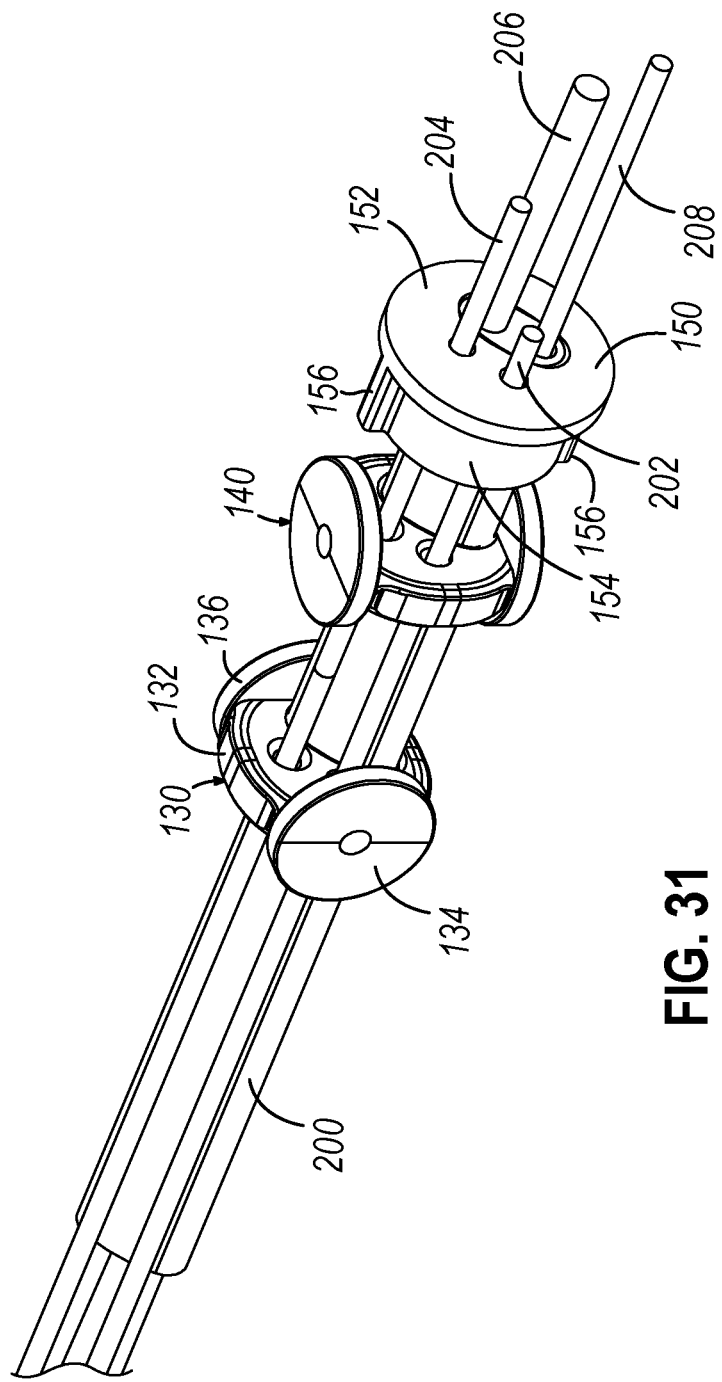
FIG. 31 depicts a perspective view of the articulation section of FIG. 29 with the articulation section having various components removed for greater clarity of an interior space of the articulation section.

As shown in FIGS. 30-31, multi-planar articulation joint (165) supports each of elongate members (202, 204, 206, 208) along a continuous path offset relative to longitudinal axis (61) to provide smooth control of elongate members (202, 204, 206, 208) that inhibits catching, kinking, over-extension, and/or over-compression of such elongate members (202, 204, 206, 208) during articulation of articulation section (170), particularly when simultaneously deflecting end effector (116) (see FIG. 29) through multiple planes. Multi-planar articulation joint (165) may further help to inhibit wear of articulation section (170). To this end, multi-planar articulation joint (165) includes a proximal plate (130) positioned within a proximal portion of articulation joint core (180), a distal plate (140) positioned within a distal portion of articulation joint core (180), and a cap (150) positioned within distal articulation joint interface (172b) for receiving and supporting elongate members (202, 204, 206, 208). In the illustrated embodiment, elongate members (206, 208) are positioned within a multi-lumen assembly (200) to support elongate members (206, 208) within plates (130, 140) and cap (150). Multi-lumen assembly (200) in the present example has an elliptical body extending proximally from cap (150) through plates (130, 140). Multi-lumen assembly (200) defines a pair of lumens (201, 203) (see FIG. 32) extending through multi-lumen assembly (200) to receive elongate members (206, 208). While multi-lumen assembly (200) is of a single, unitary construction and shown having two lumens to respectively receive two elongate members, any other suitable number of lumens can be used to receive any suitable number of elongate members within multi-lumen assembly (200). Plates (130, 140), cap (150), and/or multi-lumen assembly (200) thereby support elongate members (202, 204, 206, 208) to extend along a continuous path to maintain the spacing of elongate members (202, 204, 206, 208) relative to each other throughout multi-planar articulation joint (165). While four elongate members (202, 204, 206, 208) are shown in the present example, any other suitable number and/or configurations for elongate members (202, 204, 206, 208) may be used.

Figure 32:
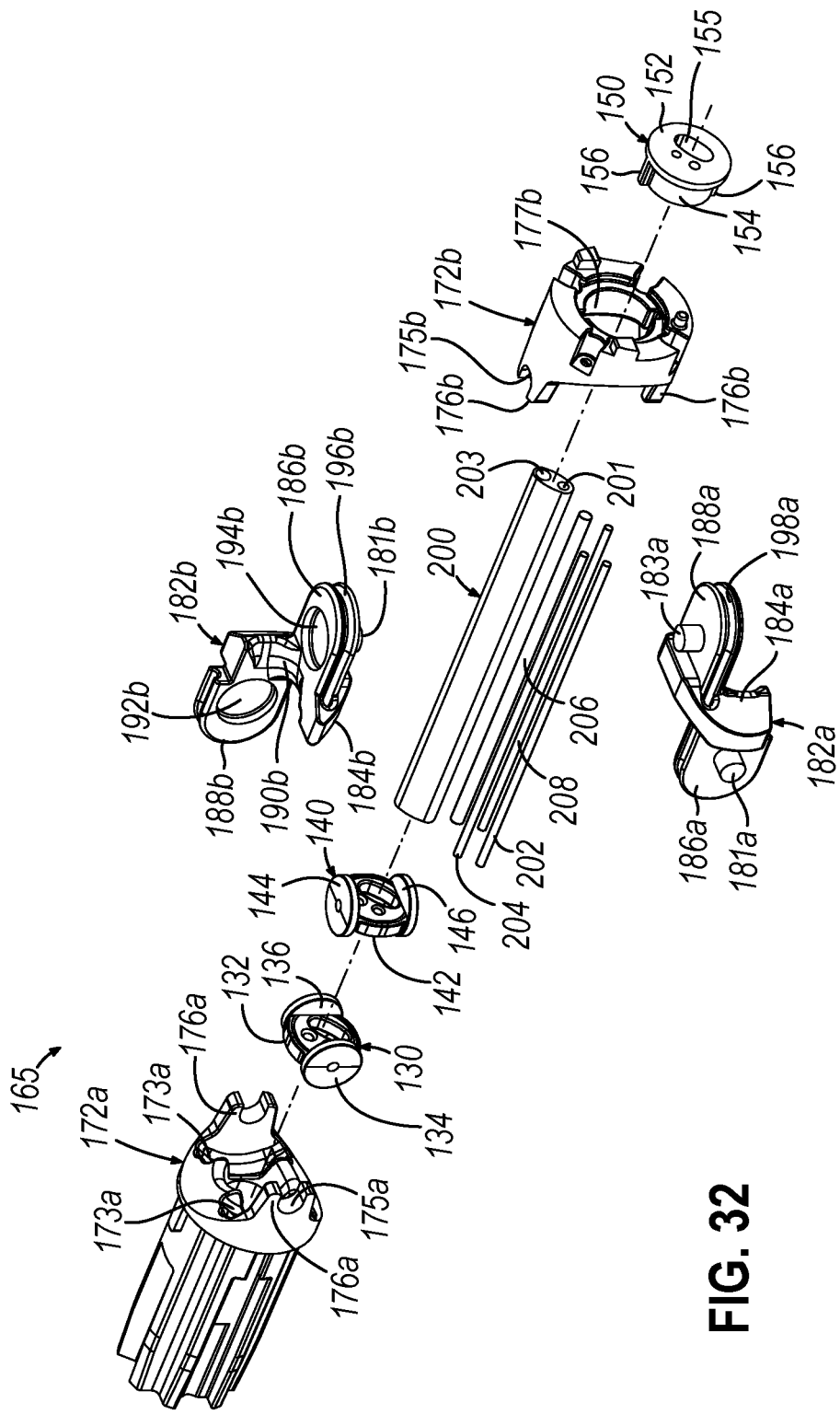
FIG. 32 depicts an exploded perspective view of the articulation section of FIG. 29.

FIG. 32 shows multi-planar articulation joint (165) in more detail. As shown in the present example, distal articulation joint interface (172b) is substantially similar to proximal articulation joint interface (172a), but is positioned in a reversed direction and orientated about 90 degrees clockwise relative to proximal articulation joint interface (172a). Second articulation joint member (182b) is also substantially similar to first articulation joint member (182a), but is positioned in a reversed direction and oriented about 90 degrees clockwise relative to first articulation joint member (182a). Accordingly, multi-planar articulation joint (165) is configured to support elongate members (202, 204, 206, 208) to maintain the spacing of elongate members (202, 204, 206, 208) relative to each other through multi-planar articulation joint (165). While first articulation joint member (182a) is discussed in more detail below, it should be noted that the discussion also applies to second articulation joint member (182b) respectively such that a like number with a differing letter indicates a like feature.

Figure 33:
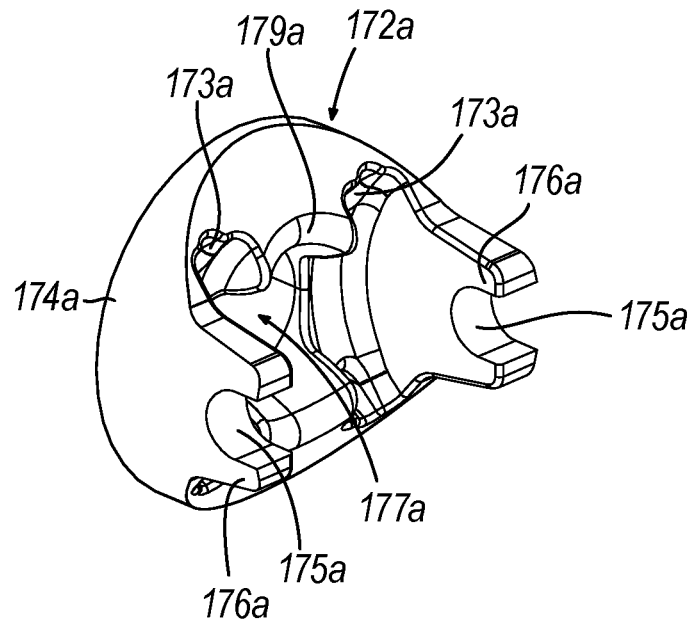
FIG. 33 depicts a perspective view of a proximal articulation joint interface of the multi-planar articulation joint of FIG. 29.
Figure 34:
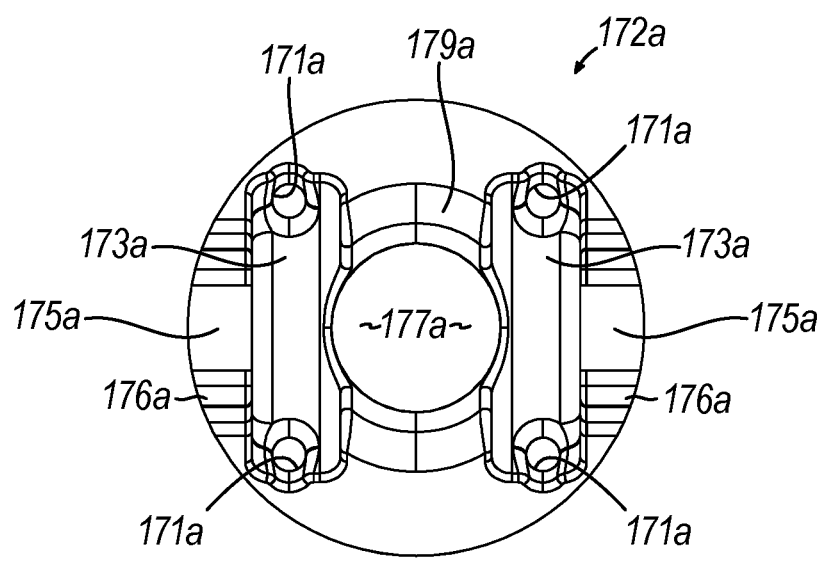
FIG. 34 depicts a side elevational view of the proximal articulation joint interface of FIG. 33.

FIGS. 33-34 show proximal articulation joint interface (172a) comprising a generally cylindrical body (174a) having a pair of arms (176a) extending outwardly from body (174a) on opposing sides of body (174a). Each arm (176a) includes an arcuate recess (175a) extending inwardly within arm (176a). Body (174a) further includes a pair of channels (173a) extending inwardly within body (174a) adjacent to each arm (176a) on opposing sides of body (174a). Each channel (173a) is curved and includes an opening (171a) extending through top and bottom portions of each channel (173a). A curved protrusion (179a) is then positioned between the opposing channels (173a) on body (174a) and defines a conduit (177a) centrally therethrough.

Figure 36:
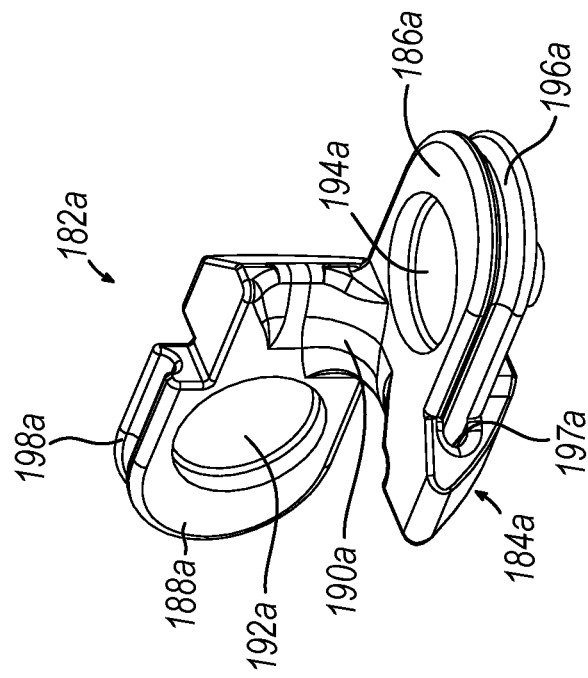
FIG. 36 depicts a bottom perspective view of the articulation joint member of FIG. 35.
Figure 35:
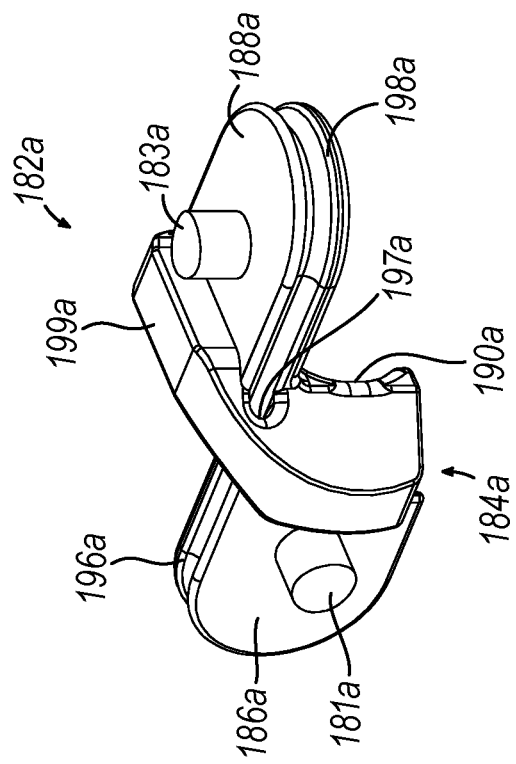
FIG. 35 depicts a top perspective view of an articulation joint member of the multi-planar articulation joint of FIG. 29.
Figure 41:
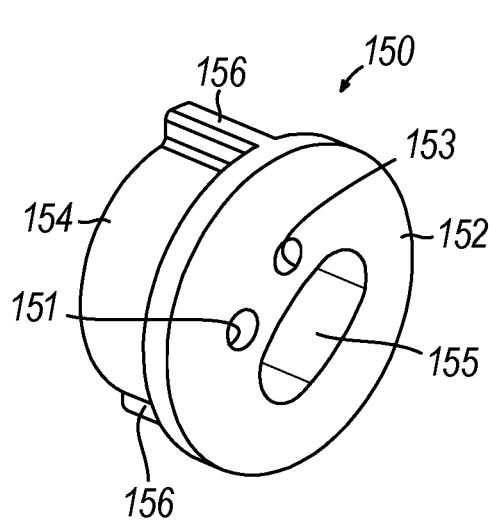
FIG. 41 depicts a right side perspective view of a cap of the multi-planar articulation joint of FIG. 29.
Figure 42:
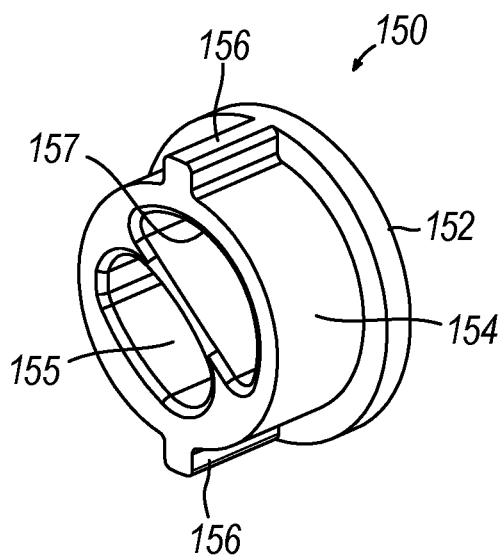
FIG. 42 depicts a left side perspective view of the cap of FIG. 41.

FIGS. 35-36 show first articulation joint member (182a) comprising a body (184a) having a collar (199a) positioned about a central portion of body (184a). Body (184a) comprises a first plate (186a) extending outwardly from collar (199a) and a second plate (188a) extending outwardly from collar (199a) in an opposing direction from first plate (186a). First plate (186a) is generally elliptical and defines a channel (196a) extending within first plate (186a) about a circumference of first plate (186a). A generally cylindrical knob (181a) extends outwardly from an exterior surface of first plate (186a) and a generally cylindrical recess (194a) extends inwardly from an interior surface of first plate (186a). Second plate (188a) is generally elliptical and defines a channel (198a) extending within second plate (188a) about a circumference of second plate (188a). A generally cylindrical knob (183a) extends outwardly from an exterior surface of second plate (188a) and a generally cylindrical recess (192a) extends inwardly from an interior surface of second plate (188a). Second plate (188a) is oriented about 90 degrees clockwise relative to first plate (186a) such that an end of channel (198a) of second plate (188a) is aligned with an end of channel (196a) of first plate (186a). An opening (197a) is then positioned through collar (199a) to connect channel (198a) of second plate (188a) with channel (196a) of first plate (198a). Body (184a) of first articulation joint member (182a) further comprises an arcuate surface (190a) extending along an interior surface of body (184a) between first and second plates (186a, 188a).

FIGS. 37-38 show proximal plate (130) comprising a generally circular body (132) and a pair of generally circular end plates (134, 136) positioned on each side of body (132) transverse to body (132). Body (132) further defines a plurality of lumens (131, 133, 135) extending therethrough. As best seen in FIG. 38, first lumen (131) and second lumen (133) are substantially circular with first lumen (131) being positioned downward and outward relative to second lumen (133). Third lumen (135) is substantially elliptical and positioned obliquely within body (132) adjacent to first and second lumens (131, 133).

FIGS. 39-40 show distal plate (140) comprising a generally circular body (142) and a pair of generally circular end plates (144, 146) positioned on a top and bottom surface of body (142) transverse to body (142). Body (142) further defines a plurality of lumens (141, 143, 145) extending therethrough. As best seen in FIG. 40, first lumen (141) and second lumen (143) are substantially circular with first lumen (141) being positioned downward and outward relative to second lumen (143). Third lumen (145) is substantially elliptical and positioned obliquely within body (142) adjacent to first and second lumens (141, 143). Accordingly, lumens (141, 143, 145) of distal plate (140) are positioned to align with lumens (131, 133, 135) of proximal plate (130).

Figure 43:
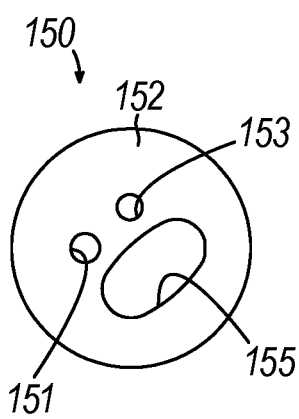
FIG. 43 depicts a right side elevational view of the cap of FIG. 41.
Figure 44:
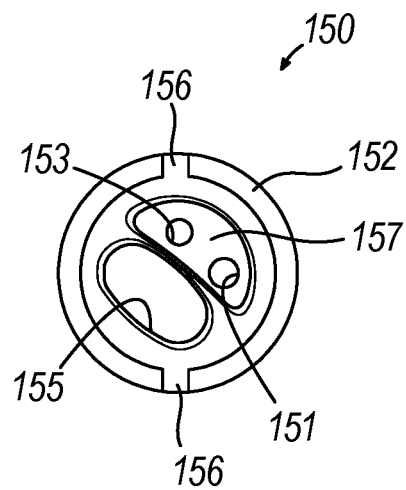
FIG. 44 depicts a left side elevational view of the cap of FIG. 41.

FIGS. 41-44 show cap (150) comprising a generally circular body (152). Body (152) defines a plurality of lumens (151, 153, 155) extending therethrough. As best seen in FIG. 43, first lumen (151) and second lumen (153) are substantially circular with first lumen (151) being positioned downward and outward relative to second lumen (153). Third lumen (155) is substantially elliptical and positioned obliquely within body (152) adjacent to first and second lumens (151, 153). Accordingly, lumens (151, 153, 155) of cap (150) are positioned to align with lumens (131, 133, 135) of proximal plate (130) and lumens (141, 143, 145) of distal plate (140). Cap (150) further comprises a generally cylindrical protrusion (154) extending proximally from body (152) that has a smaller outer diameter than body (152). A pair of flanges (156) then extend radially outward from opposing surfaces of protrusion (154) to the outer diameter of body (152). A generally elliptical recess (157) extends through protrusion (154) to body (152) to position first and second lumens (151, 153) within recess (157). Third lumen (153) extends continuously through body (152) and protrusion (154) adjacent to recess (157).

Figure 45:
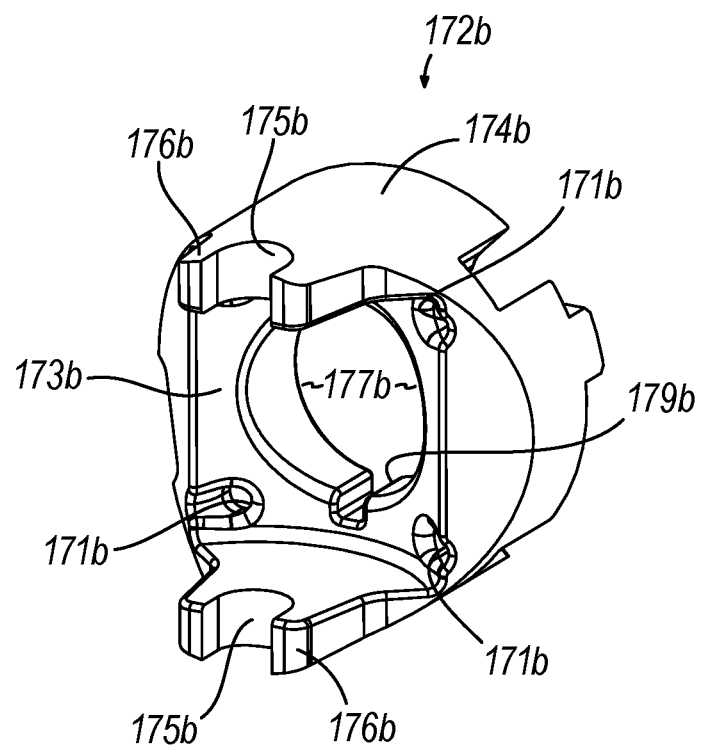
FIG. 45 depicts a perspective view of a distal articulation joint interface of the multi-planar articulation joint of FIG. 29.
Figure 46:
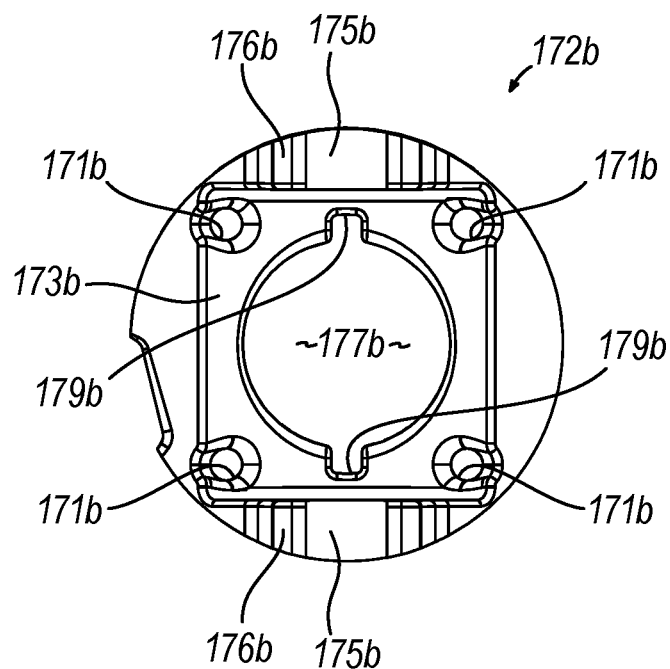
FIG. 46 depicts a side elevational view of the distal articulation joint interface of FIG. 45.

FIGS. 45-46 show distal articulation joint interface (172b) comprising a generally cylindrical body (174b) having a pair of arms (176b) extending outwardly from body (174b) on opposing sides of body (174b). Each arm (176b) includes an arcuate recess (175b) extending inwardly within arm (176b). Body (174b) further includes a channel (173b) extending inwardly within body (174b) between each arm (176b). Channel (173b) includes a plurality of openings (171b) extending through a top and bottom portion of each side portion of channel (173b). A conduit (177b) extends through a central portion of channel (173b), and a pair of cut-outs (179b) extend radially outward from conduit (177b) within channel (173b).

Figure 47:
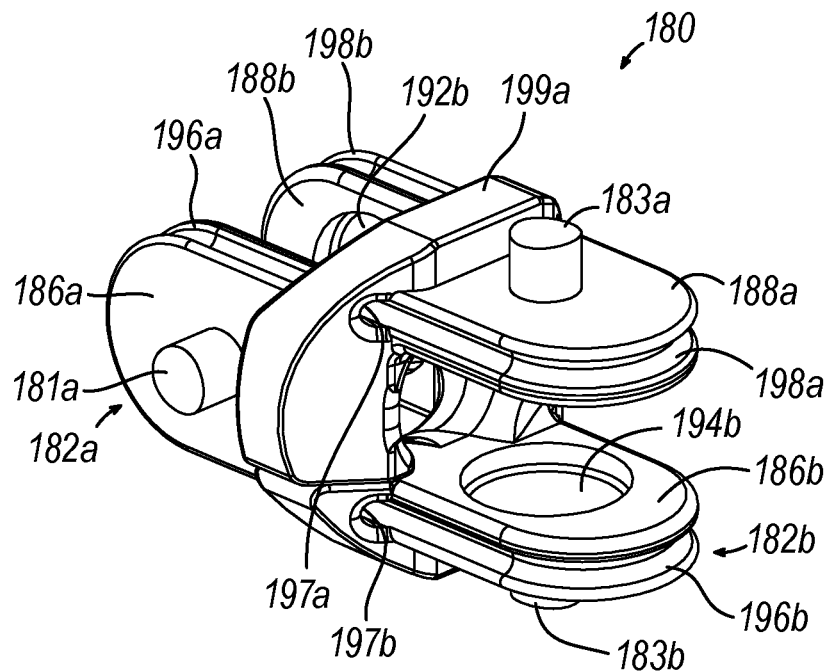
FIG. 47 depicts a perspective view of an articulation joint core of the multi-planar articulation joint of FIG. 29.
Figure 48:
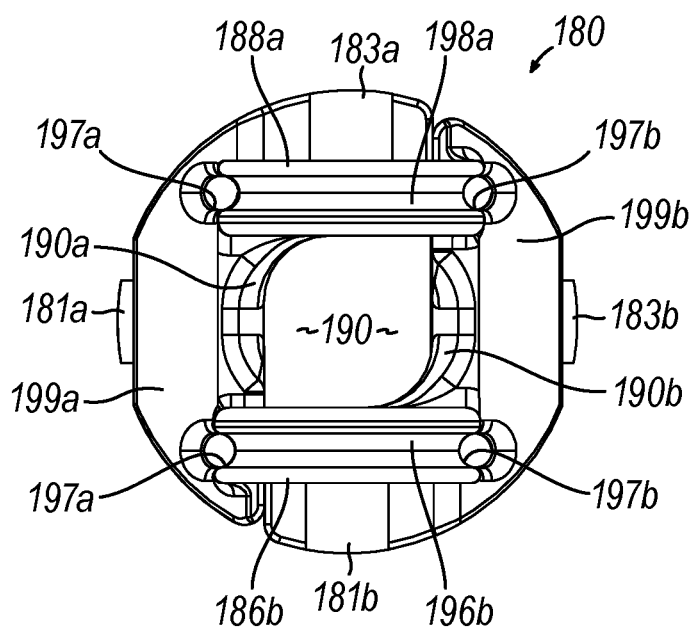
FIG. 48 depicts a side elevational view of the articulation joint core of FIG. 47.
Figure 49:
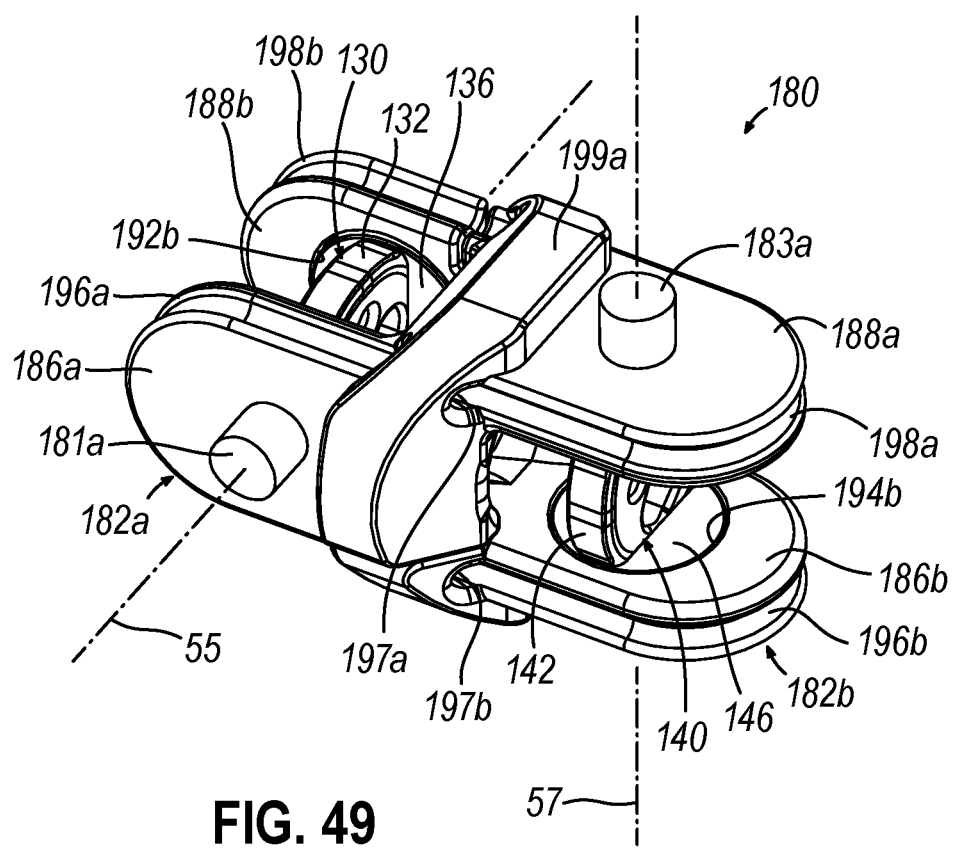
FIG. 49 depicts a perspective view the articulation joint core of FIG. 47 assembled with the proximal plate and the distal plate of the multi-planar articulation joint of FIG. 29.

FIGS. 47-48 show first articulation joint member (182a) assembled with second articulation joint member (182b) to form articulation joint core (180). As shown, second articulation joint member (182b) is oriented in an opposing longitudinal direction and reoriented about 90 degrees clockwise relative to first articulation joint member (182a). This aligns arcuate surface (190a) of first articulation joint member (182a) with arcuate surface (190b) of second articulation joint member (182b) to form lumen (190). As shown in FIG. 49, proximal plate (130) is positioned within a proximal portion of articulation joint core (180) such that end plate (136) of proximal plate (130) is received within recess (192b) of second plate (188b) of second articulation joint member (182b) and end plate (134) (see FIG. 37) of proximal plate (130) is received within recess (194a) (see FIG. 36) of first plate (186a) of first articulation joint member (182a). This positions body (132) of proximal plate (130) between first plate (186a) of first articulation joint member (182a) and second plate (188b) of second articulation joint member (182b) to align lumens (131, 133, 135) (see FIG. 38) of body (132) with lumen (190) of articulation joint core (180). Distal plate (140) is positioned within a distal portion of articulation joint core (180) such that end plate (144) (see FIG. 39) of distal plate (140) is received within recess (192a) (see FIG. 36) of second plate (188a) of first articulation joint member (182a) and end plate (146) of distal plate (140) is received within recess (194b) of first plate (186b) of second articulation joint member (182b). This positions body (142) of distal plate (140) between first plate (186b) of second articulation joint member (182b) and second plate (188a) of first articulation joint member (182a) to align lumens (141, 143, 145) (see FIG. 40) of body (142) with lumen (190) of articulation joint core (180). Accordingly, articulation joint core (180) is configured to position body (132) of proximal plate (130) at the first articulation axis (55) with end plates (134, 136) (see FIG. 38) positioned along first articulation axis (55) and body (142) of distal plate (140) at the second articulation axis (57) with end plates (144, 146) (see FIG. 40) of distal plate (140) along second articulation axis (57).

Figure 50:
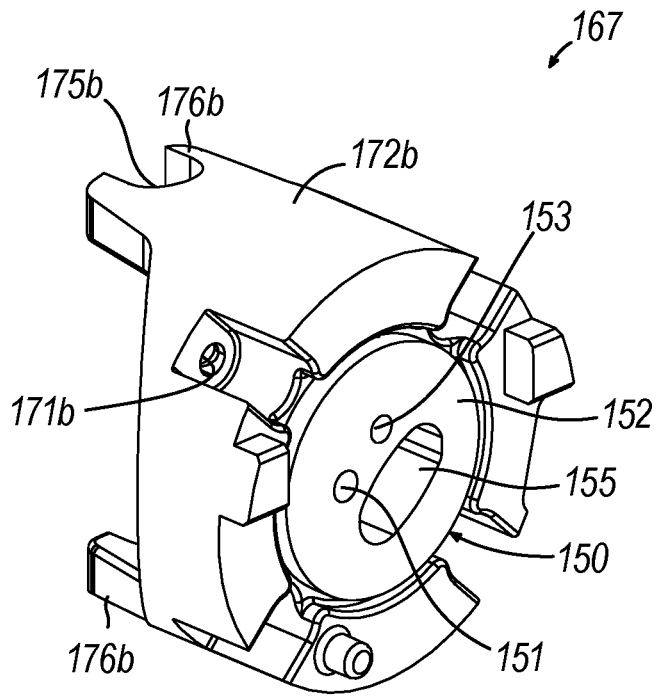
FIG. 50 depicts a right perspective view of a distal articulation joint assembly of the multi-planar articulation joint of FIG. 29.
Figure 51:
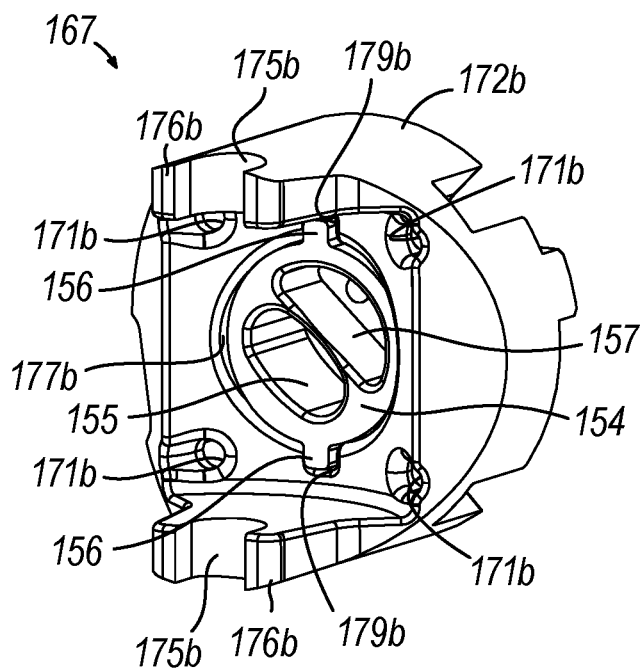
FIG. 51 depicts a left perspective view of the distal articulation joint assembly of FIG. 50.

FIGS. 50-51 show cap (150) inserted within conduit (177b) of distal articulation joint interface (172b) to form distal articulation joint assembly (167). Cap (150) is positioned within conduit (177b) such that each protrusion (156) of cap (150) is inserted within a cut-out (179b) of distal articulation joint interface (172b) to maintain the rotational position of cap (150) relative to distal articulation joint interface (172b).

In use, referring to FIGS. 30-32, articulation joint core (180) with proximal and distal plates (130, 140) is assembled with proximal joint interface (172a) and distal articulation joint assembly (167). Accordingly, proximal articulation joint interface (172a) is coupled proximally to articulation joint core (180) and distal articulation joint assembly (167) is coupled distally to distal articulation joint core (180). For instance, a knob (181a) of first articulation joint member (182a) is inserted within recess (175a) of proximal articulation joint interface (172a) and knob (183b) (see FIG. 48) of second articulation joint member (182b) is inserted within the opposing recess (175a) of proximal articulation joint interface (172a). Knobs (181a, 183b) (see FIG. 48) are rotatable within respective recesses (175a) to thereby allow articulation joint core (180) to pivot relative to proximal articulation joint interface (172a) about first articulation axis (55). First plate (186a) of first articulation joint member (182a) is inserted within channel (173a) of proximal articulation joint interface (172a) and second plate (188b) of second articulation joint member (182b) within the opposing channel (173a) of proximal articulation joint interface (172a). Opening (177a) (see FIG. 34) of proximal articulation joint interface (172a) is thereby aligned with lumen (190) (see FIG. 48) of articulation joint core (180). The curved configurations of plates (186a, 188b) and respective channels (173a) allow plates (186a, 188b) of articulation joint core (180) to rotate smoothly within channels (173a) as articulation joint core (180) is pivoted about first articulation axis (55).

On the distal end portion of articulation joint core (180), knob (183a) of first articulation joint member (182a) is inserted within recess (175b) of distal articulation joint interface (172b) and knob (181b) of second articulation joint member (182b) is inserted within the opposing recess (175b) of distal articulation joint interface (172b). Knobs (181b, 183a) are rotatable within respective recesses (175b) to thereby allow distal articulation joint interface (172b) to pivot relative to articulation joint core (180) about second articulation axis (57). Second plate (188a) of first articulation joint member (182a) and first plate (186b) of second articulation joint member (182b) are inserted within respective channels (173b) of distal articulation joint interface (172b). Opening (177b) of distal articulation joint interface (172b) is thereby aligned with lumen (190) (see FIG. 48) of articulation joint core (180). The curved configurations of plates (186b, 188a) and respective channels (173b) allow plates (186b, 188a) of articulation joint core (180) to rotate smoothly within channels (173b) as distal articulation joint interface (172b) is pivoted about second articulation axis (57).

With continued reference to FIGS. 30-32 as well as FIGS. 34, 38, 40, 44, and 48, elongate members (202, 204, 206, 208) are respectively positioned through conduits (177a) of proximal articulation joint interface (172a), through lumens (131, 133, 135) of proximal plate (130), through lumen (190) of articulation joint core (180), through lumens (141, 143, 145) of distal plate (140), and through lumens (151, 153, 155) of cap (150) within conduit (177b) of distal articulation joint interface (172b). Thereby, elongate members (202, 204, 206, 208) operatively extend from base assembly (12) (see FIG. 1) and connect with end effector (116) (see FIG. 29) for operation of end effector (116) (see FIG. 29). In the illustrated embodiment, elongate member (202) is configured to extend through lumen (131) of proximal plate (130), lumen (141) of distal plate (140), and lumen (151) of cap (150) such that elongate member (202) extends continuously through articulation joint core (180) along an axis that is substantially parallel with and offset from longitudinal axis (61) in the straight configuration. Elongate member (204) is configured to extend through lumen (133) of proximal plate (130), lumen (143) of distal plate (140), and lumen (153) of cap (150) such that elongate member (204) extends continuously through articulation joint core (180) along an axis that is substantially parallel with and offset from longitudinal axis (61) and elongate member (202) in the straight configuration. Elongate member (206) is configured to extend through lumen (203) of multi-lumen assembly (200) and elongate member (208) is configured to extend through lumen (201) of multi-lumen assembly (200) respectively. Multi-lumen assembly (200) is then sized to be inserted within lumen (135) of proximal plate (130), lumen (145) of distal plate (140), and lumen (155) of cap (150) such that elongate members (206, 208) extend continuously through articulation joint core (180) along an axis that is substantially parallel with and offset from longitudinal axis (61) and elongate members (202, 204) in the straight configuration.

Figure 52:
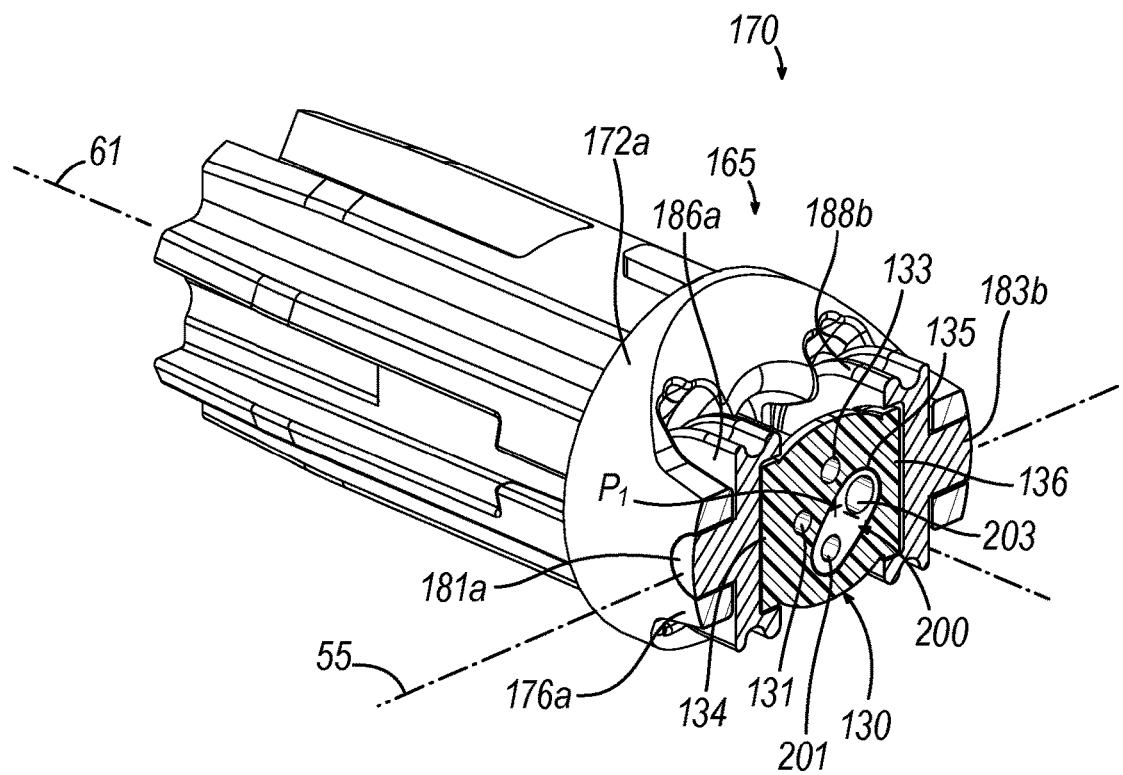
FIG. 52 depicts a cross-sectional side view of the articulation section of FIG. 29 taken along section line 52-52 of FIG. 30, showing the articulation joint defining a plurality of lumens radially offset from the longitudinal axis at the first articulation axis.
Figure 53:
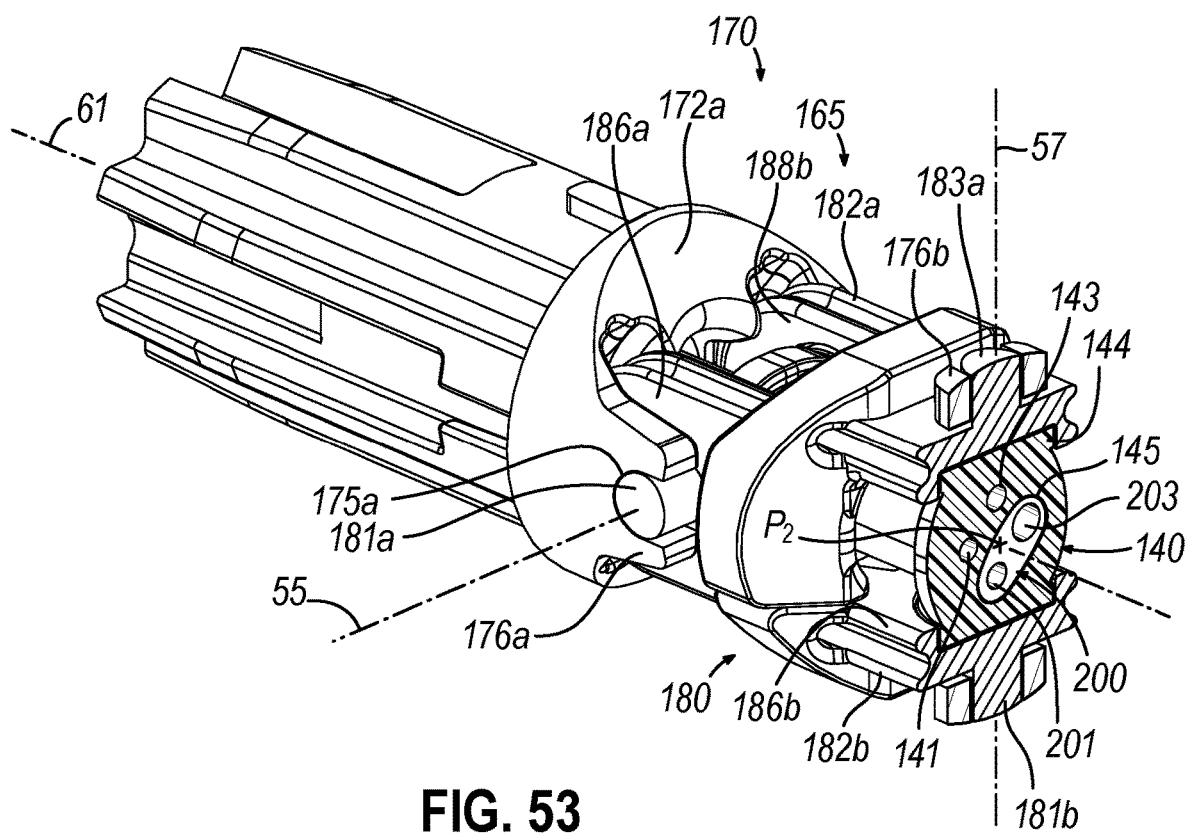
FIG. 53 depicts a cross-sectional side view of the articulation section of FIG. 29 taken along section line 53-53 of FIG. 30, showing the plurality of lumens of the articulation joint radially offset from the longitudinal axis at the second articulation axis.

In some versions, multi-planar articulation joint (165) is configured to inhibit elongate members (206, 208) from translating within multi-planar articulation joint (165). Referring to FIGS. 52-53, multi-planar articulation joint (165) is configured to maintain the spaced relationship between elongate members (202, 204, 206, 208) (see FIG. 30) at each articulation axis (55, 57) during articulation of articulation section (170). As shown in FIG. 52, proximal plate (130) is positioned along first articulation axis (55) such that first articulation axis (55) intersects longitudinal axis (61) at first point ($P_1$) at a central portion of proximal plate (130). One or more lumens (131, 133, 135) of proximal plate (130) are each radially offset from first point ($P_1$) at a predetermined distance. Accordingly, proximal plate (130) maintains this radial space between the one or more lumens (131, 133, 135) and first point ($P_1$) at the predetermined distance as articulation section (170) is deflected from a straight configuration with articulation section (170) aligned along longitudinal axis (61) to a deflected configuration with articulation section (170) pivoted about first articulation axis (55) to deflect end effector (116) upwardly and/or downwardly along the first plane relative to longitudinal axis (61). As shown in FIG. 53, distal plate (140) is positioned along second articulation axis (57) such that second articulation axis (57) intersects longitudinal axis (61) at second point ($P_2$) at a central portion of distal plate (140). One or more lumens (141, 143, 145) of distal plate (140) are each radially offset from second point ($P_2$) at a predetermined distance. Accordingly, distal plate (140) maintains this radial space between the one or more lumens (141, 143, 145) and second point ($P_2$) at the predetermined distance as articulation section (170) is deflected from a straight configuration with articulation section (170) aligned along longitudinal axis (61) to a deflected configuration with articulation section (170) pivoted about second articulation axis (57) to deflect end effector (116) outwardly and/or inwardly along the second plane relative to longitudinal axis (61). With (202, 204, 206, 208) (see FIG. 30) positioned through lumens (131, 133, 135, 141, 143, 145), multi-planar articulation joint (165) is thereby configured to maintain the radially spaced relationship between elongate members (202, 204, 206, 208) (see FIG. 30) at each articulation axis (55, 57) during articulation of articulation section (170). Still other suitable configurations for multi-planar articulation joint (165) will be apparent to one with ordinary skill in the art in view of the teachings herein.

Figure 54:
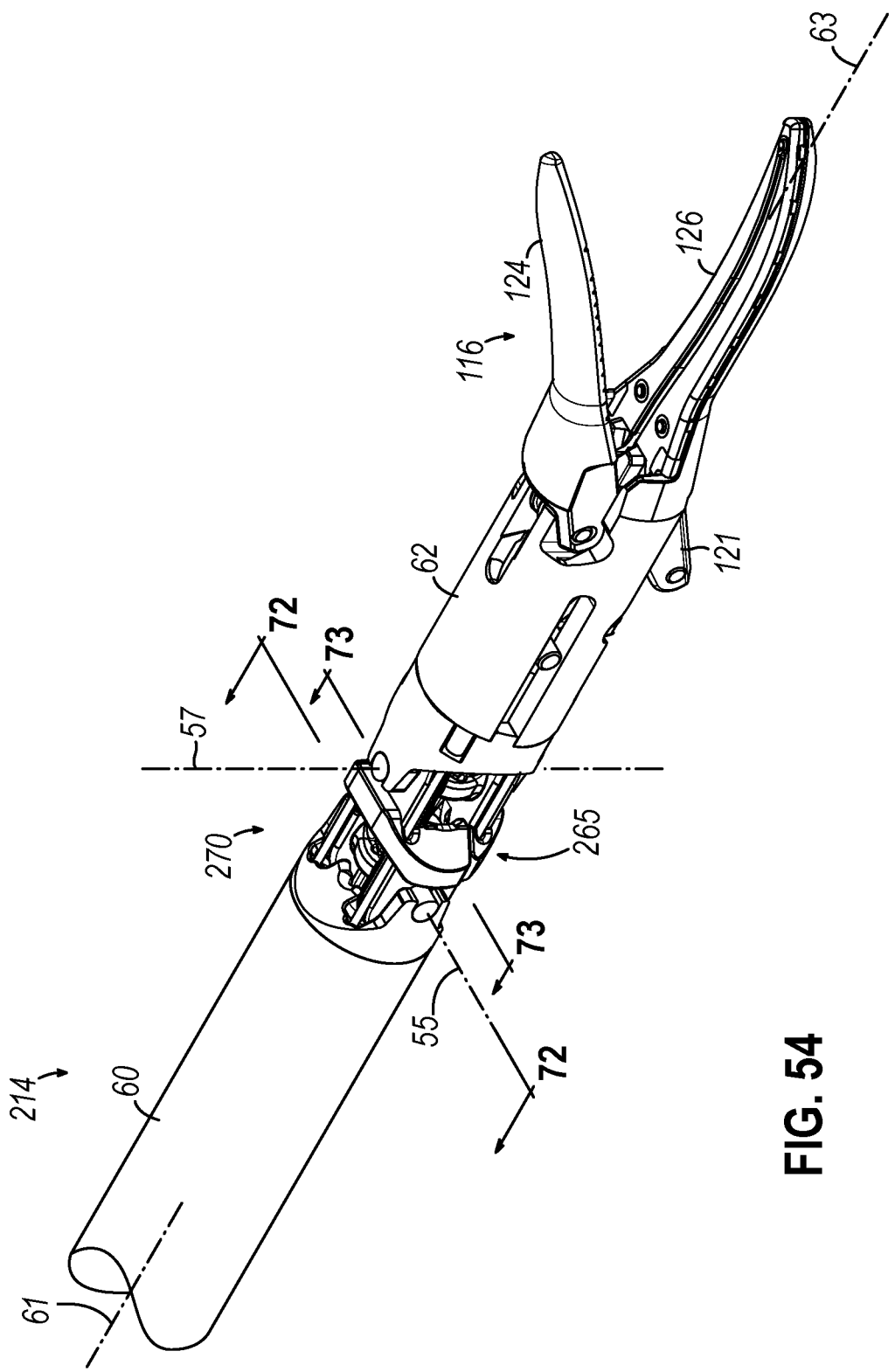
FIG. 54 depicts a perspective view of another alternative shaft assembly for use with the base assembly of FIG. 1, the shaft assembly having an articulation section with a third exemplary multi-planar articulation joint.
Figure 55:
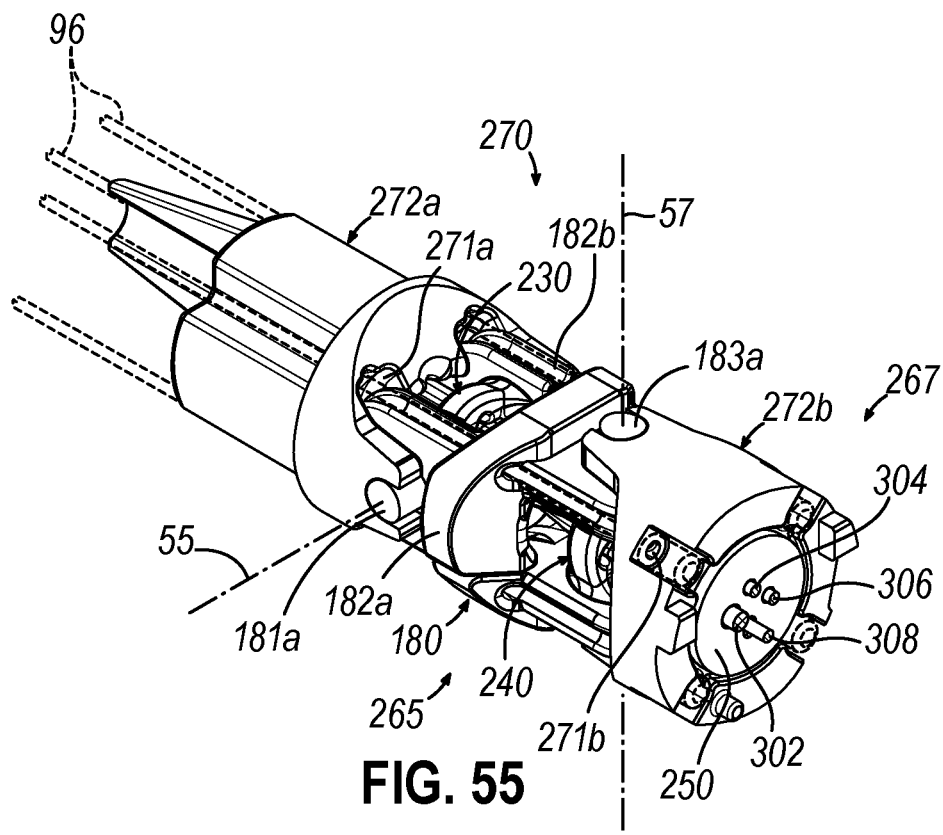
FIG. 55 depicts a perspective view of the articulation section of FIG. 54.

E. Alternative Exemplary Shaft Assembly Having an Articulation Section with a Third Exemplary Multi-Planar Articulation Joint FIG. 54 shows an alternative shaft assembly (214) for use with base assembly (12) (see FIG. 1) described above such that like numbers below indicate like features described above in greater detail. Shaft assembly (214) of the present example includes an alternative exemplary articulation section (270) having a third exemplary multi-planar articulation joint (265) configured to deflect end effector (116) through a plurality of planes. Referring to FIGS. 54-55, multi-planar articulation joint (265) includes a proximal articulation joint interface (272a) extending distally from proximal shaft portion (60), a distal articulation joint interface (272b) extending proximally from distal shaft portion (62), and articulation joint core (180) positioned between proximal and distal articulation joint interfaces (272a, 272b). As discussed above, articulation joint core (180) includes first articulation joint member (182a) assembled with second articulation joint member (182b) such that second articulation joint member (182b) is oriented about 90 degrees clockwise relative to first articulation joint member (182a) about longitudinal axis (61). Each of first and second articulation joint members (182a, 182b) are thereby assembled to form articulation joint core (180), which is pivotable relative to longitudinal axis (61) of proximal shaft portion (60) to position end effector (116) in various positions about longitudinal axis (61) similar to articulation joint core (80) described above.

In order to selectively drive multi-planar articulation joint (265), cables (96) extend from base assembly (12) (see FIG. 1) to multi-planar articulation joint (265). In the present example, proximal articulation joint interface (272a) is coupled with proximal shaft portion (60) and distal articulation joint interface (272b) is coupled with distal shaft portion (62). Four such cables (96) extend through openings (271a) of proximal articulation joint interface (272a), through corresponding channels (196a, 198a, 196b, 198b) (see FIGS. 47-48) and openings (197a, 197b) (see FIGS. 47-48) of articulation joint core (180), and through openings (271b) of distal articulation joint interface (272b). Cables (96) thereby connect to distal articulation joint interface (272b) such that pulling on cables (96) on one side of multi-planar articulation joint (265) will selectively articulate multi-planar articulation joint (265). It will be appreciated that such cables (96) may be pulled in various combinations to achieve any desired articulation. Still other suitable configurations for articulating multi-planar articulation joint (265) will be apparent to one with ordinary skill in the art in view of the teachings herein.

With respect to FIGS. 54-55, multi-planar articulation joint (265) further provides support and guidance for elongate members (302, 304, 306, 308) extending through articulation section (270) that may couple components of base assembly (12) (see FIG. 1) and/or shaft assembly (214) with end effector (116) for operation of end effector (116). For instance, one or more elongate members (302, 304) may include cables acting in tension such that elongate member (302) may be used for pivoting upper jaw (124) into the closed position and elongate member (304) may be used for pivoting upper jaw (124) into the open position. Additionally, elongate member (306) may be configured to provide RF energy to end effector (116) and elongate member (308) may be configured as a knife rod for cutting tissue grasped within end effector (116). Still other suitable configurations for elongate members (302, 304, 306, 308) will be apparent to one with ordinary skill in the art in view of the teachings herein.

Figure 56:
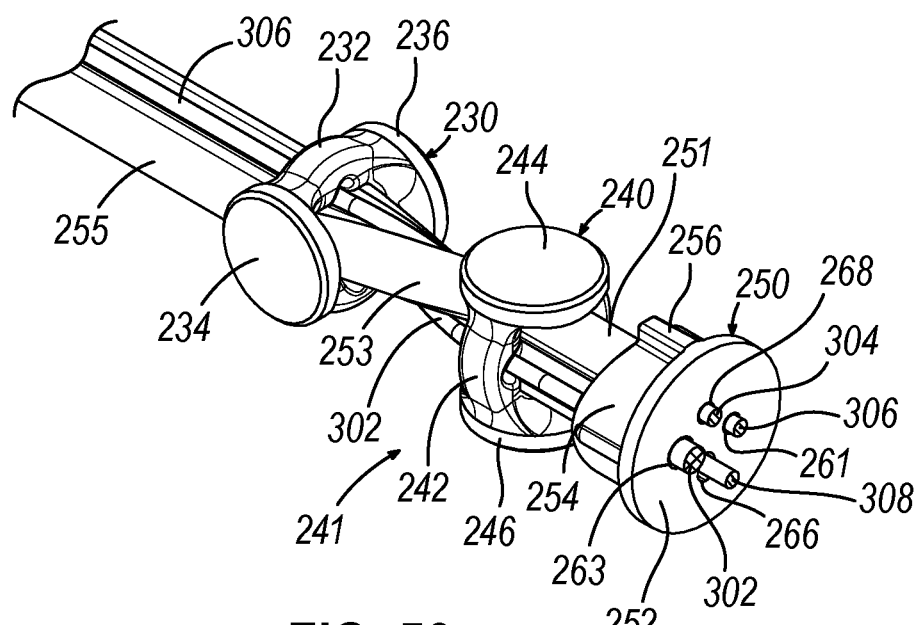
FIG. 56 depicts a perspective view of the articulation section of FIG. 54 with the articulation section having various components removed for greater clarity of an interior space of the articulation section.

As shown in FIGS. 55-56, multi-planar articulation joint (265) supports each of elongate members (302, 304, 306, 308) along a continuous path offset relative to longitudinal axis (61) (see FIG. 54) to provide smooth control of elongate members (302, 304, 306, 308) that inhibits catching, kinking, over-extension, and/or over-compression of such elongate members (302, 304, 306, 308) during articulation of articulation section (270), particularly when simultaneously deflecting end effector (116) (see FIG. 54) through multiple planes. In addition, this continuous path followed by elongate members (302, 304, 306, 308) is helical such that multi-planar articulation joint (265) of the present example supports a pair of elongate members (304, 308) to further inhibit over-extension and/or over-compression as will be discussed below in greater detail. Multi-planar articulation joint (265) may further help to inhibit wear of articulation section (270). To this end, multi-planar articulation joint (265) includes a proximal plate (230) positioned within a proximal portion of articulation joint core (180), a distal plate (240) positioned within a distal portion of articulation joint core (180), and a support sleeve (241) having multi-lumen assembly (258) and a cap (250) positioned within distal articulation joint interface (272b) for receiving and supporting elongate members (302, 304, 306, 308). In the illustrated embodiment, elongate members (302, 304, 306, 308) are supported by multi-lumen assembly (258) through plates (230, 240) such that plates (230, 240) and cap (250) support elongate members (302, 304, 306, 308) along a continuous path to maintain the spacing of elongate members (302, 304, 306, 308) relative to each other throughout multi-planar articulation joint (265). While four elongate members (302, 304, 306, 308) are shown in the present example, any other suitable number and/or configurations for elongate members (302, 304, 306, 308) may be used.

Figure 57:
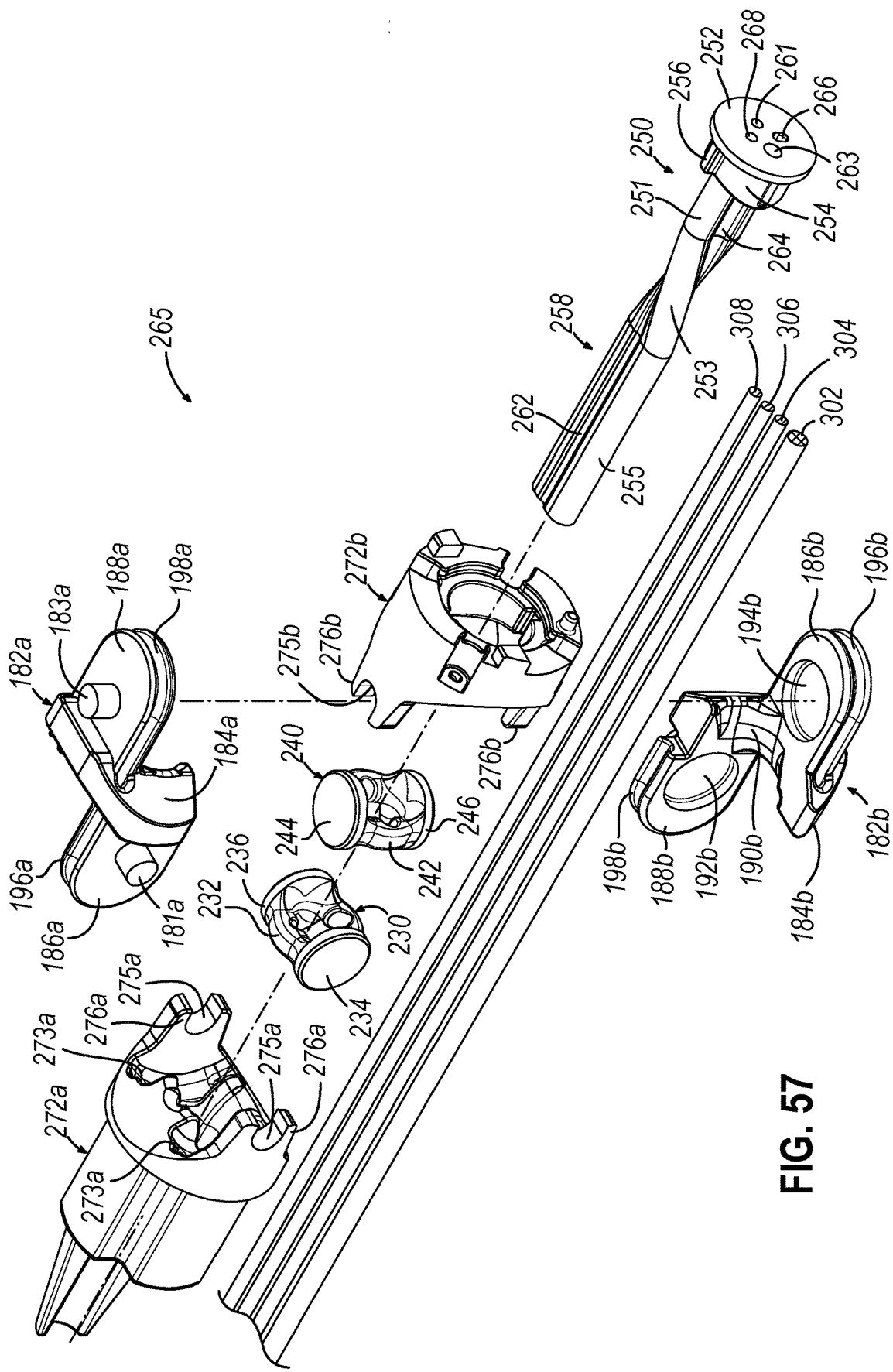
FIG. 57 depicts an exploded perspective view of the articulation section of FIG. 54.

FIG. 57 shows multi-planar articulation joint (265) in more detail. As shown in the present example, distal articulation joint interface (272b) is substantially similar to proximal articulation joint interface (272a), but is positioned in a reversed direction and orientated about 90 degrees clockwise relative to proximal articulation joint interface (272a). Second articulation joint member (182b) is also substantially similar to first articulation joint member (182a), but is positioned in a reversed direction and oriented about 90 degrees clockwise relative to first articulation joint member (182a). Accordingly, multi-planar articulation joint (265) is configured to support elongate members (302, 304, 306, 308) to maintain the spacing of elongate members (302, 304, 306, 308) relative to each other through multi-planar articulation joint (265).

Figure 58:
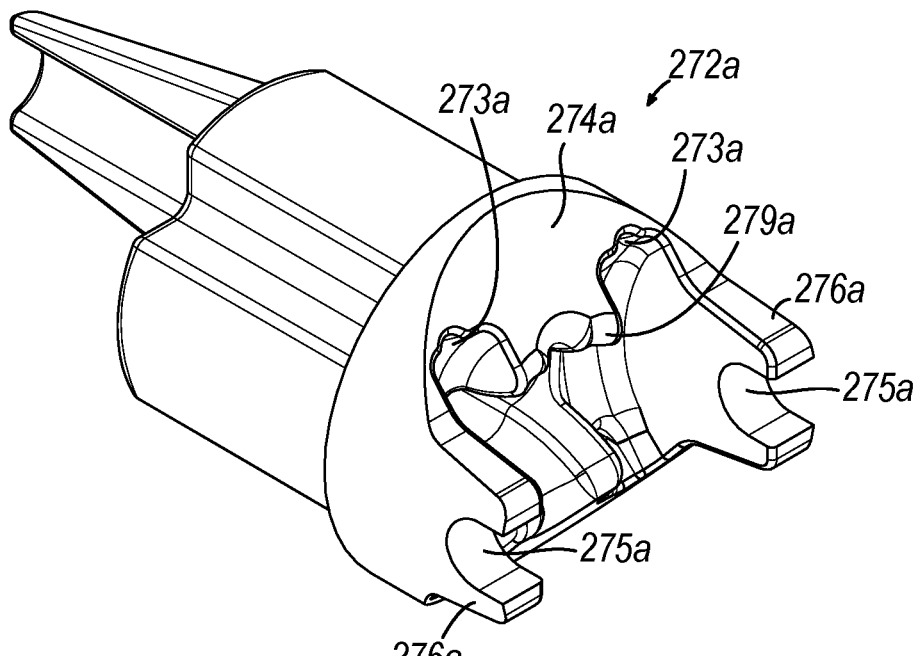
FIG. 58 depicts a perspective view of a proximal articulation joint interface of the multi-planar articulation joint of FIG. 54.
Figure 59:
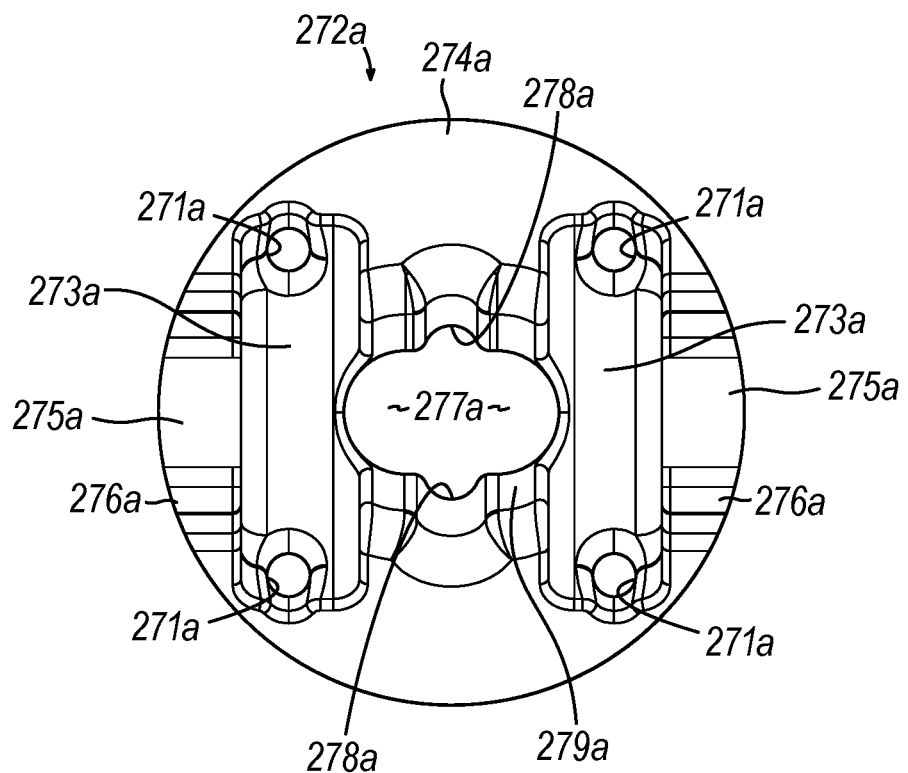
FIG. 59 depicts a side elevational view of the proximal articulation joint interface of FIG. 58.

FIGS. 58-59 show proximal articulation joint interface (272a) comprising a generally cylindrical body (274a) having a pair of arms (276a) extending outwardly from body (274a) on opposing sides of body (274a). Each arm (276a) includes an arcuate recess (275a) extending inwardly within arm (276a). Body (274a) further includes a pair of channels (273a) extending inwardly within body (274a) adjacent to each arm (276a) on opposing sides of body (274a). Each channel (273a) is curved and includes an opening (271a) extending through top and bottom portions of each channel (273a). A curved protrusion (279a) is then positioned between the opposing channels (273a) on body (274a) and defines a conduit (277a) centrally therethrough. A pair of recesses (278a) extend through a top and bottom portion of conduit (277a).

Figure 61:
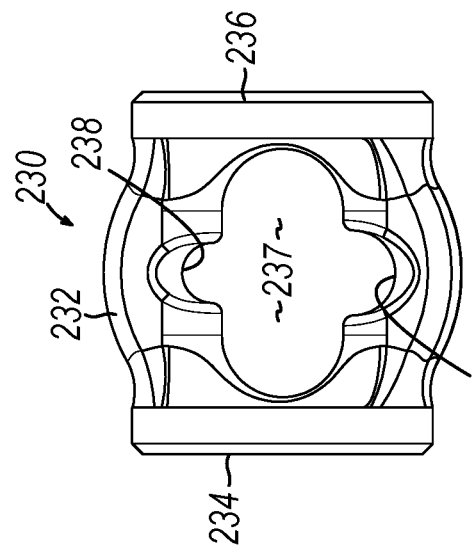
FIG. 61 depicts a side elevational view of the proximal plate of FIG. 60.
Figure 60:
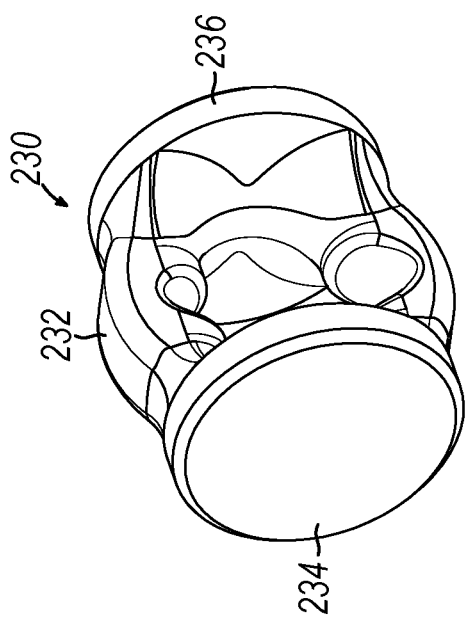
FIG. 60 depicts a perspective view of a proximal plate of the multi-planar articulation joint of FIG. 54.

FIGS. 60-61 show proximal plate (230) comprising a generally circular body (232) and a pair of generally circular end plates (234, 236) positioned on each side of body (232) transverse to body (232). Body (232) further defines a lumen (237) extending therethrough and having a pair of recesses (238) extending from a top and bottom portion of lumen (237). As best seen in FIG. 61, lumen (237) has a generally cross-shaped configuration.

Figure 63:
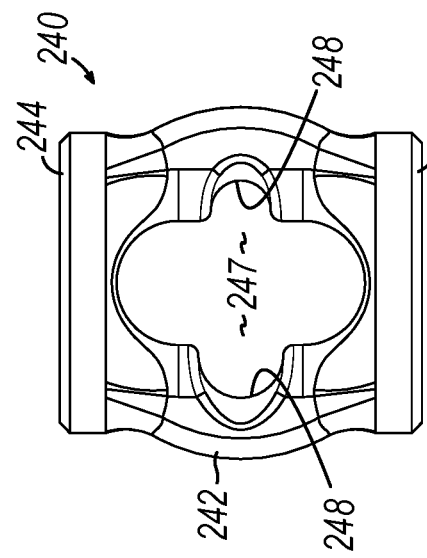
FIG. 63 depicts a side elevational view of the distal plate of FIG. 62.
Figure 62:
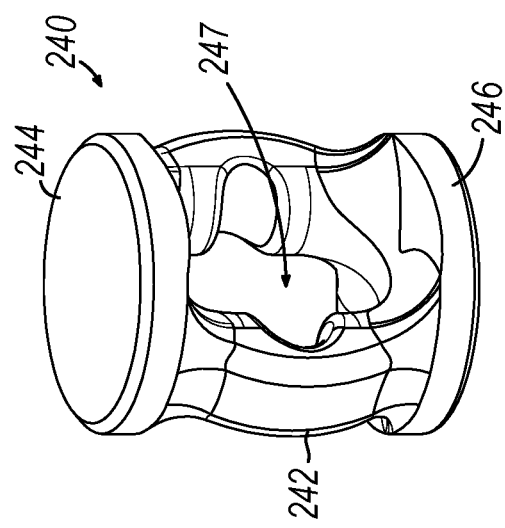
FIG. 62 depicts a perspective view of a distal plate of the multi-planar articulation joint of FIG. 54.
Figure 65:
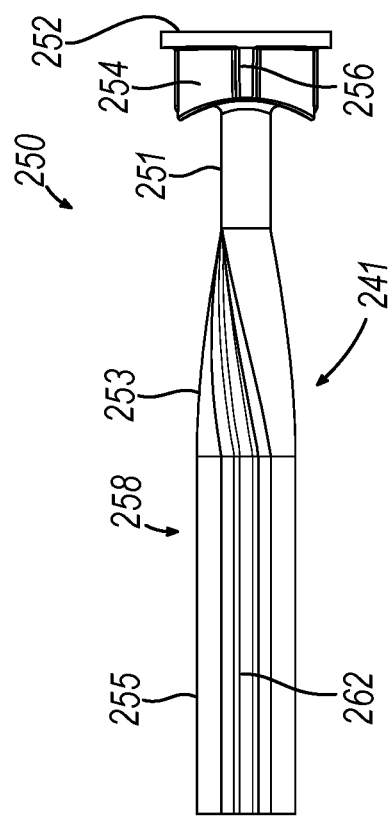
FIG. 65 depicts a top plan view of the support sleeve of FIG. 64.
Figure 67:
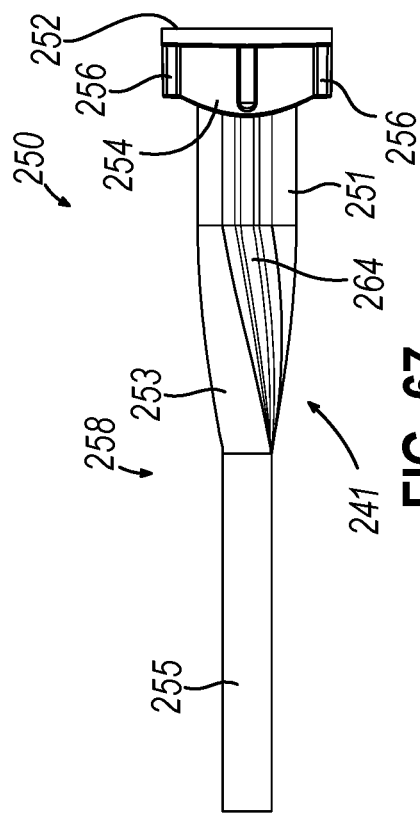
FIG. 67 depicts a front view of the support sleeve of FIG. 64.
Figure 64:
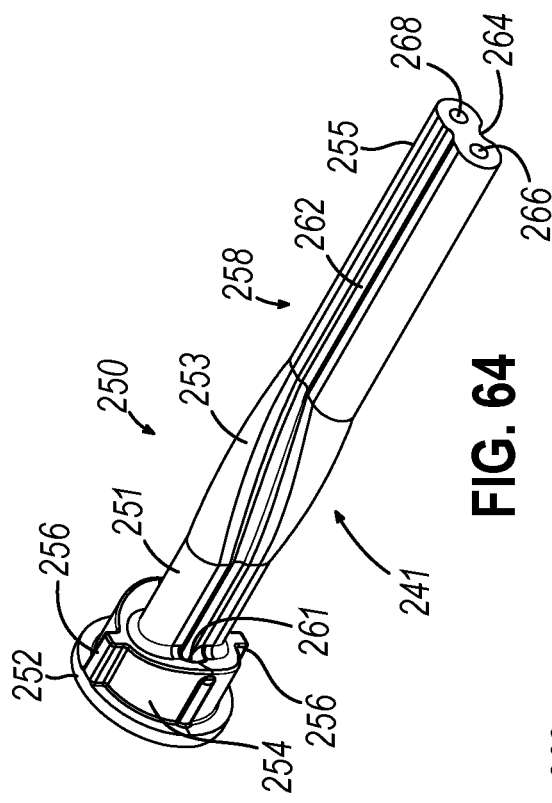
FIG. 64 depicts a top perspective view of a support sleeve of the multi-planar articulation joint of FIG. 54.
Figure 66:
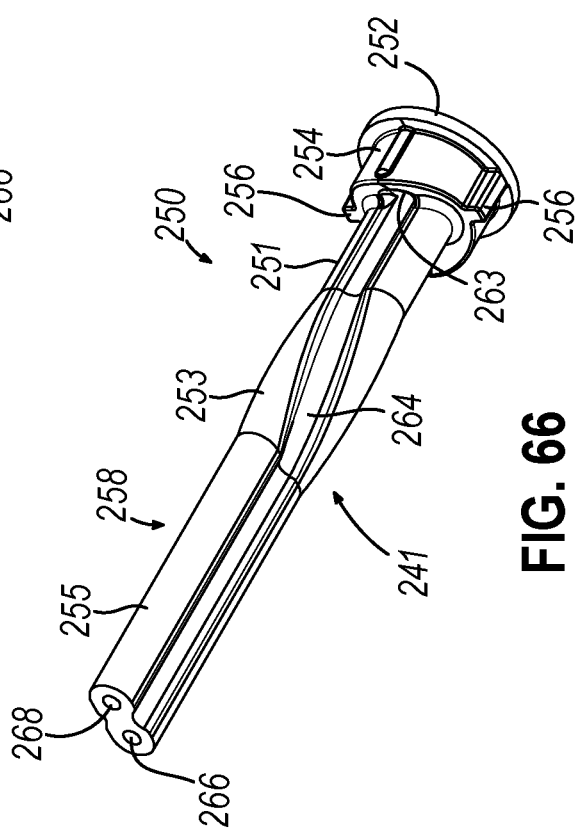
FIG. 66 depicts a bottom perspective view of the support sleeve of FIG. 64.

FIGS. 62-63 show distal plate (240) comprising a generally circular body (242) and a pair of generally circular end plates (244, 246) positioned on a top and bottom surface of body (242) transverse to body (242). Body (242) further defines a lumen (247) extending therethrough and having a pair of recesses (248) extending from each side portion of lumen (247). As best seen in FIG. 63, lumen (247) has a generally cross-shaped configuration.

FIGS. 64-67 show support sleeve (241) having a cap (250) comprising a generally circular body (252). Body (152) defines a plurality of lumens (261, 263, 266, 268) (see FIG. 57) extending therethrough. Cap (250) further comprises a generally cylindrical protrusion (254) extending proximally from body (252) that has a smaller outer diameter than body (252). A pair of flanges (256) then extend radially outward from opposing surfaces of protrusion (254) to the outer diameter of body (252). Support sleeve (241) further comprises multi-lumen assembly (258) extending proximally from protrusion (254). Two of lumens (266, 268) continuously extend from circular body (252) through multi-lumen assembly (258). Multi-lumen assembly (258) then defines a pair of recesses (262, 264) extending along an outer surface of multi-lumen assembly (258) such that each recess (262, 264) respectively aligns with the other two lumens (261, 263) of circular body (252). While multi-lumen assembly (258) has a single, unitary construction defining two lumens (266, 268) and two recesses (262, 264) as shown, any other suitable number of lumens (266, 268) and recesses (262, 264) or alternative, multi-component assemblies may be used. Multi-lumen assembly (258) includes a distal portion (251), an intermediate portion (253), and a proximal portion (255). Distal portion (251) is positioned to orient lumens (266, 268) generally horizontally relative to each other. Intermediate portion (253) then rotates lumens (266, 268) about 90 degrees such that proximal portion (255) is positioned to orient lumens (266, 268) generally vertically relative to each other. Accordingly, recesses (262, 264) are oriented generally vertically relative to each other at distal portion (255) and generally horizontally relative to each other at proximal portion (251).

Figure 68:
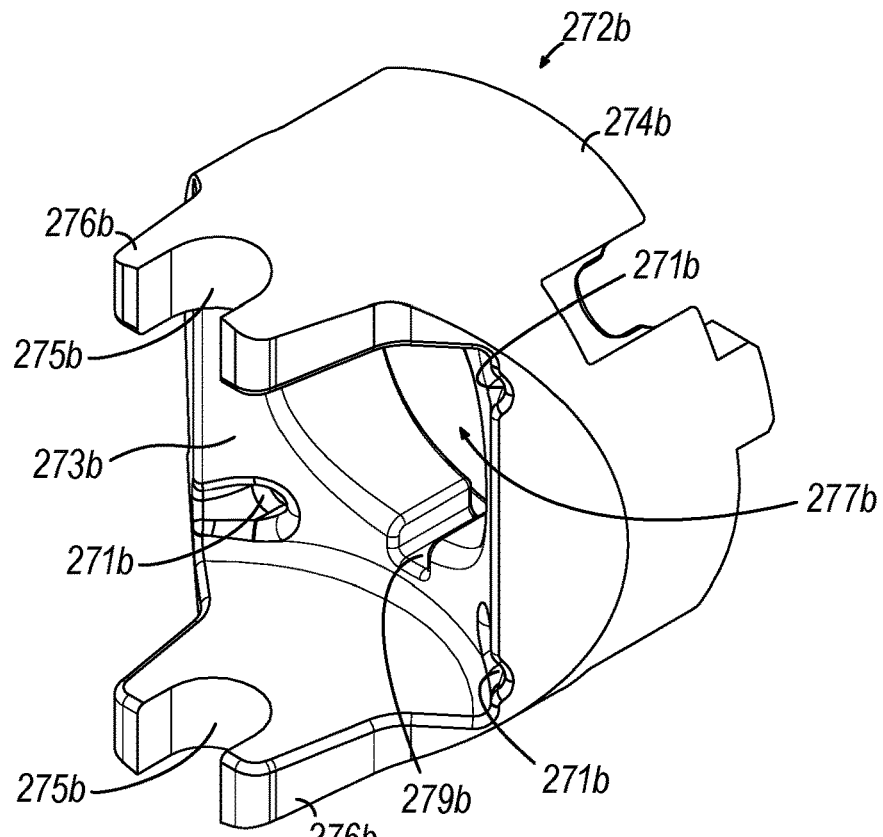
FIG. 68 depicts a perspective view of a distal articulation joint interface of the multi-planar articulation joint of FIG. 54.
Figure 69:
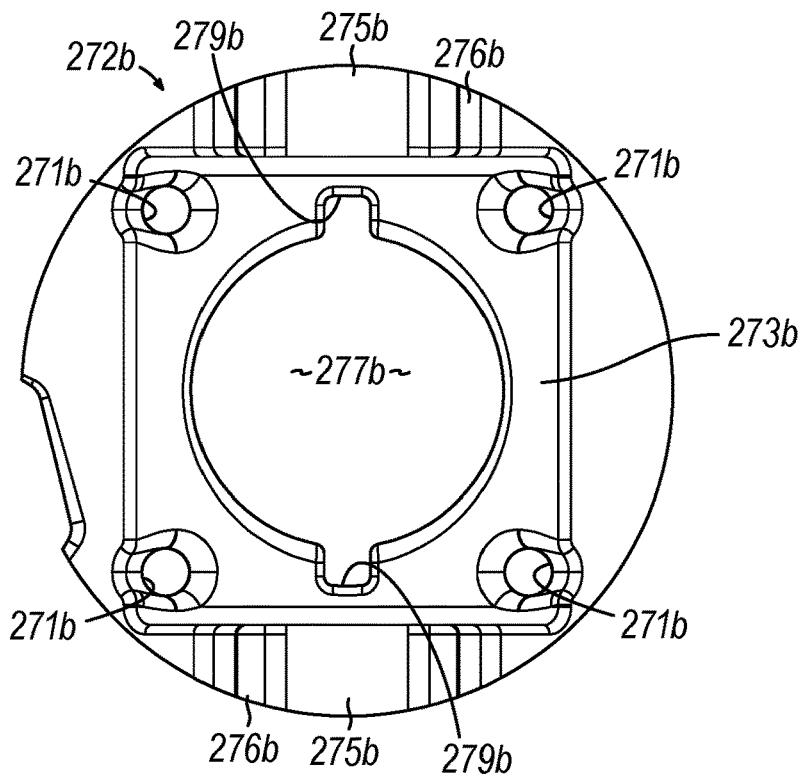
FIG. 69 depicts a side elevational view of the distal articulation joint interface of FIG. 68.
Figure 70:
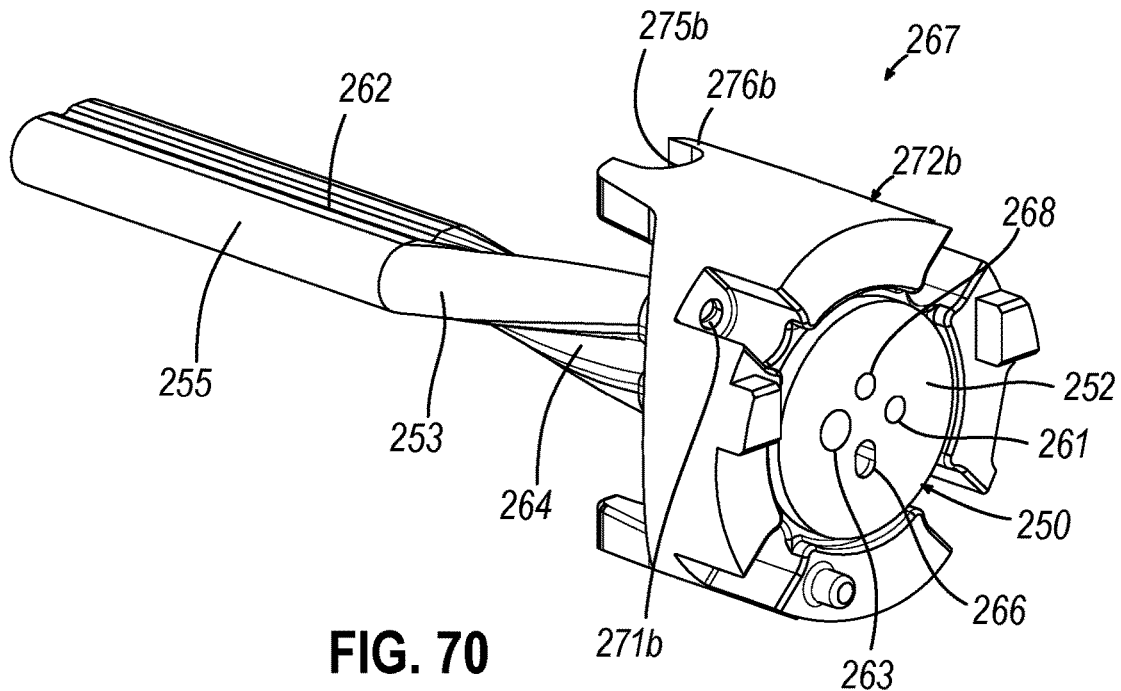
FIG. 70 depicts a right side perspective view of an articulation joint core of the multi-planar articulation joint of FIG. 54.
Figure 71:
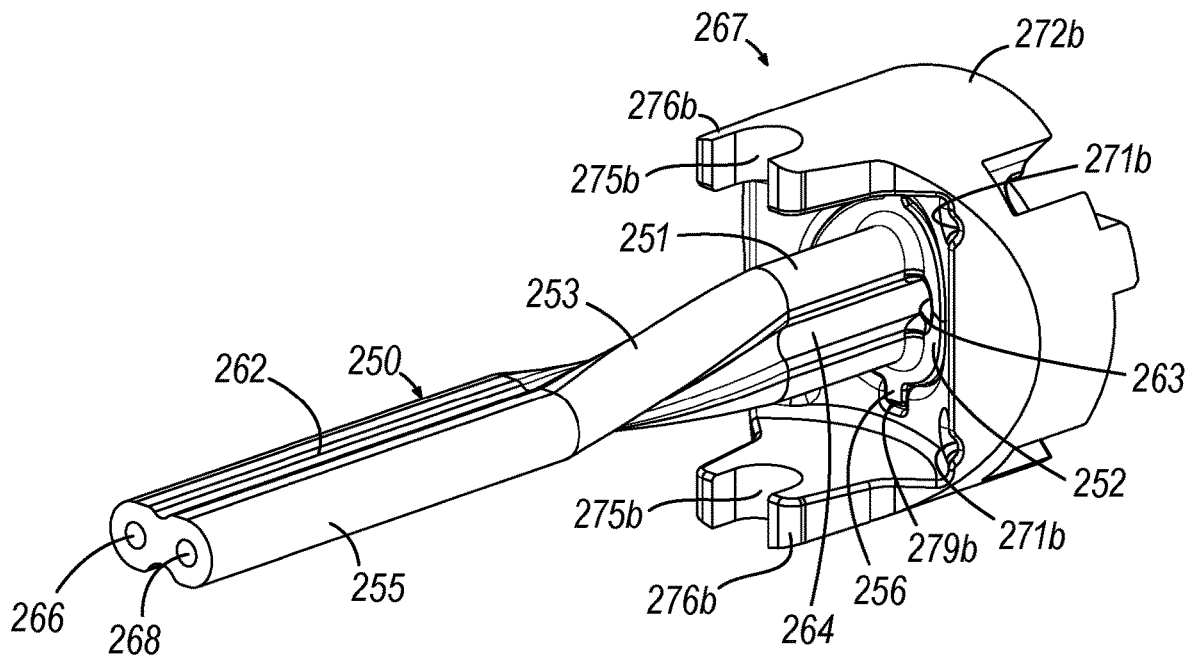
FIG. 71 depicts a left side perspective view of the articulation joint core of FIG. 70.

FIGS. 68-69 show distal articulation joint interface (272b) comprising a generally cylindrical body (274b) having a pair of arms (276b) extending outwardly from body (274b) on opposing sides of body (274b). Each arm (276b) includes an arcuate recess (275b) extending inwardly within arm (276b). Body (274b) further includes a channel (273b) extending inwardly within body (274b) between each arm (276b). Channel (273b) includes a plurality of openings (271b) extending through a top and bottom portion of each side portion of channel (273b). A conduit (277b) extends through a central portion of channel (273b), and a pair of cut-outs (279b) extend radially outward from conduit (277b) within channel (273b). FIGS. 70-71 show cap (250) inserted within conduit (277b) (see FIG. 69) of distal articulation joint interface (272b) to form distal articulation joint assembly (267). Cap (250) is positioned within conduit (277b) (see FIG. 69) such that each protrusion (256) of cap (250) is inserted within a cut-out (279b) of distal articulation joint interface (272b) to maintain the rotational position of cap (250) relative to distal articulation joint interface (272b).

Figure 72:
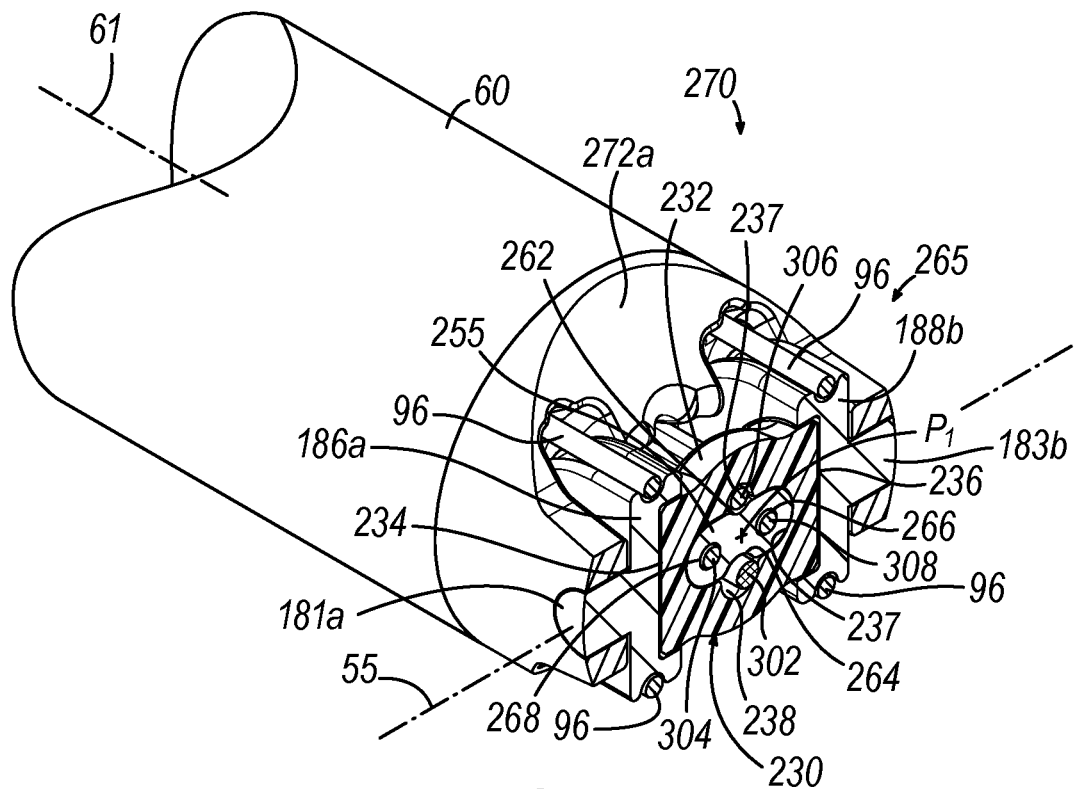
FIG. 72 depicts a cross-sectional side view of the articulation section of FIG. 54 taken along section line 72-72 of FIG. 54, showing the articulation joint defining a plurality of lumens radially offset from the longitudinal axis at the first articulation axis.
Figure 73:
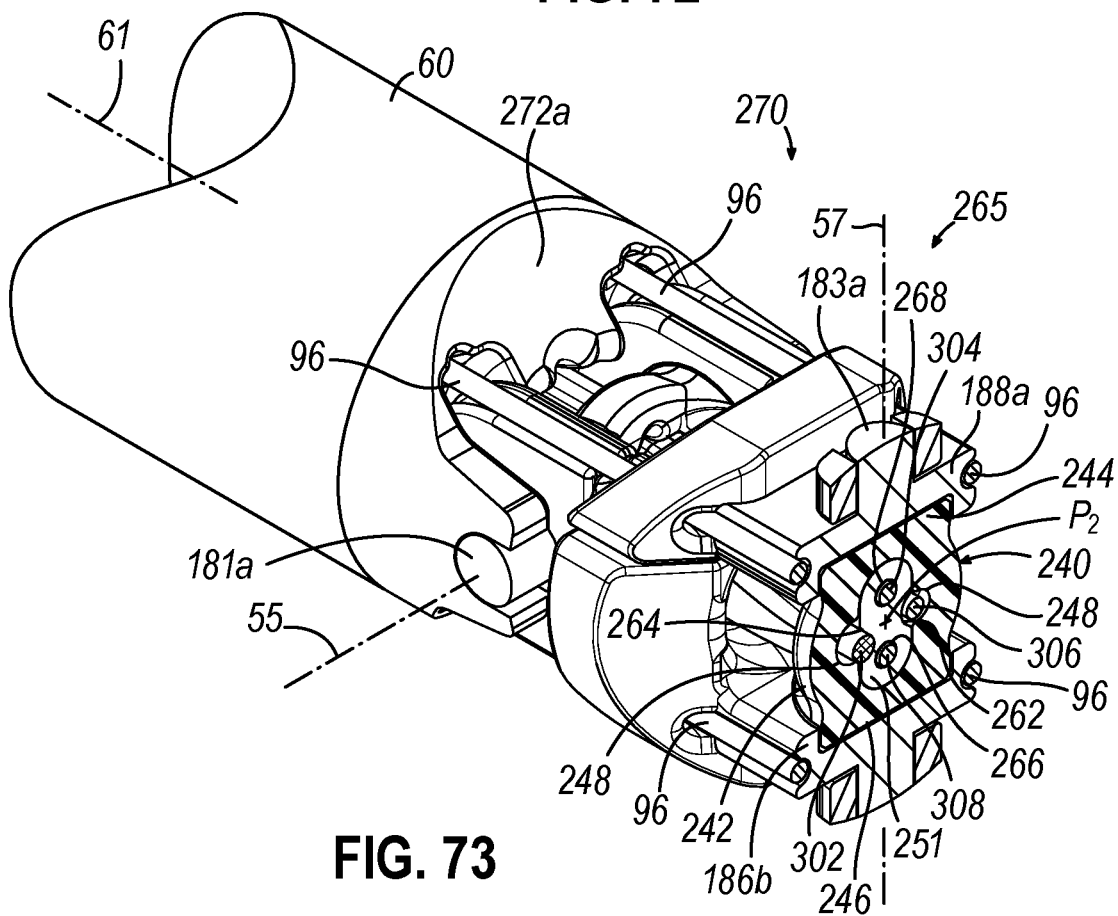
FIG. 73 depicts a cross-sectional side view of the articulation section of FIG. 54 taken along section line 73-73 of FIG. 54, showing the plurality of lumens of the articulation joint radially offset from the longitudinal axis at the second articulation axis.

As briefly above with respect to FIG. 55 with particular reference to FIGS. 72-73, multi-planar articulation joint (265) supports the pair of elongate members (304, 308) along a continuous helical path to provide smooth control of elongate members (304, 308) that inhibits catching, kinking, over-extension, and/or over-compression of such elongate members (304, 308) during articulation of articulation section (270), particularly when simultaneously deflecting end effector (116) (see FIG. 54) through multiple planes. Elongate members (304, 308) of the present example are thus positioned on each articulation axis (55, 57). In contrast, another pair of elongate member (302, 306) of the present example are neither positioned on articulation axis (55) nor on articulation axis (57). Still, both pairs of elongate members (302, 304, 306, 308) spiral thereabout within spiraling lumens (266, 268) and recesses (262, 264) as applicable. While two pairs of elongate members (302, 304, 306, 308) are shown in the present example, any other suitable number and/or configurations for elongate members (302, 304, 306, 308) may be used.

Referring to FIG. 72, a proximal portion of multi-planar articulation joint (65) is configured to laterally align lumens (266, 268) to be offset from each other along and intersect with first articulation axis (55). Accordingly, as multi-planar articulation joint (265) pivots about first articulation axis (55), elongate members (304, 308) are positioned along first articulation axis (55) such that elongate members (304, 308) may articulate about first articulation axis (55) with multi-planar articulation joint (265). As elongate members (304, 308) extend distally, lumens (266, 268) support elongate members (304, 308) within articulation section (270) to thereby laterally align elongate members (304, 308) obliquely between first articulation axis (55) and second articulation axis (57). As elongate members (304, 308) continue to extend distally, a distal portion of multi-planar articulation joint (265) is configured to laterally align lumens (266, 268) to be offset from each other along second articulation axis (57), as shown in FIG. 73. Thus, as multi-planar articulation joint (65) pivots about second articulation axis (57), elongate members (304, 308) are positioned along and intersect with second articulation axis (57) such that elongate members (304, 308) may articulate about second articulation axis (57). Multi-planar articulation joint (265) thereby supports elongate members (304, 308) in a collective helical configuration to align elongate members (304, 308) along the select articulation axis (55, 57) for supporting and guiding translation of elongate members (304, 308) during articulation while maintaining the spaced of each of elongate members (302, 304, 306, 308) as discussed below in greater detail.

In use, referring to FIGS. 55-57, articulation joint core (180) with proximal and distal plates (230, 240) is assembled with proximal joint interface (272a) and distal articulation joint assembly (267). Accordingly, proximal articulation joint interface (272a) is coupled proximally to articulation joint core (180) and distal articulation joint assembly (267) is coupled distally to distal articulation joint core (180). For instance, knob (181a) of first articulation joint member (182a) is inserted within recess (275a) of proximal articulation joint interface (272a) and knob (183b) (see FIG. 48) of second articulation joint member (182b) is inserted within the opposing recess (275a) of proximal articulation joint interface (272a). Knobs (181a, 183b) (see FIG. 48) are rotatable within respective recesses (275a) to thereby allow articulation joint core (180) to pivot relative to proximal articulation joint interface (272a) about first articulation axis (55). First plate (186a) of first articulation joint member (182a) is inserted within channel (273a) of proximal articulation joint interface (272a) and second plate (188b) of second articulation joint member (182b) within the opposing channel (273a) of proximal articulation joint interface (272a). Opening (277a) (see FIG. 59) of proximal articulation joint interface (272a) is thereby aligned with lumen (190) (see FIG. 48) of articulation joint core (180). The curved configurations of plates (186a, 188b) and respective channels (273a) allow plates (186a, 188b) of articulation joint core (180) to rotate smoothly within channels (273a) as articulation joint core (180) is pivoted about first articulation axis (55).

On the distal end portion of articulation joint core (180), knob (183a) of first articulation joint member (182a) is inserted within recess (275b) of distal articulation joint interface (272b) and knob (181b) (see FIG. 48) of second articulation joint member (182b) is inserted within the opposing recess (275b) of distal articulation joint interface (272b). Knobs (181b, 183a) are rotatable within respective recesses (275b) to thereby allow distal articulation joint interface (272b) to pivot relative to articulation joint core (180) about second articulation axis (57). Second plate (188a) of first articulation joint member (182a) and first plate (186b) of second articulation joint member (182b) are inserted within channel (273b) (see FIG. 68) of distal articulation joint interface (272b). Opening (277b) (see FIG. 69) of distal articulation joint interface (272b) is thereby aligned with lumen (190) (see FIG. 48) of articulation joint core (180). The curved configurations of plates (186b, 188a) and respective channel (273b) (see FIG. 68) allow plates (186b, 188a) of articulation joint core (180) to rotate smoothly within channels (273b) (see FIG. 68) as distal articulation joint interface (272b) is pivoted about second articulation axis (57).

With continued reference to FIGS. 54-57 as well as FIGS. 48, 59, 61, and 63-65, elongate members (302, 304, 306, 308) are respectively positioned through conduit (277a) of proximal articulation joint interface (272a), through lumen (237) of proximal plate (230), through lumen (190) of articulation joint core (180), through lumen (247) of distal plate (240), and through lumens (261, 263, 266, 268) of cap (250) within conduit (277b) of distal articulation joint interface (272b). Thereby, elongate members (302, 304, 306, 308) operatively extend from base assembly (12) (see FIG. 1) and connect with end effector (116) for operation of end effector (116). In the illustrated embodiment, elongate member (302) is configured to extend along recess (264) of multi-lumen assembly (258) through bottom recess (238) of proximal plate (230), recess (248) of distal plate (240), and lumen (263) of cap (250) such that elongate member (302) extends continuously through articulation joint core (180) along an axis that is substantially parallel with and offset from longitudinal axis (61) in the straight configuration. Elongate member (304) is configured to extend through lumen (268) of multi-lumen assembly (258), through lumen (237) of proximal plate (230), lumen (247) of distal plate (240), and lumen (268) of cap (250) such that elongate member (304) extends continuously through articulation joint core (180) along an axis that is substantially parallel with and offset from longitudinal axis (61) and elongate member (302) in the straight configuration. Elongate member (306) is configured to extend along recess (262) of multi-lumen assembly (258) through top recess (238) of proximal plate (230), recess (248) of distal plate (240), and lumen (261) of cap (250) such that elongate member (306) extends continuously through articulation joint core (180) along an axis that is substantially parallel with and offset from longitudinal axis (61) and elongate members (302, 304) in the straight configuration. Elongate member (308) is configured to extend through lumen (266) of multi-lumen assembly (258), through lumen (237) of proximal plate (230), lumen (247) of distal plate (240), and lumen (266) of cap (250) such that elongate member (308) extends continuously through articulation joint core (180) along an axis that is substantially parallel with and offset from longitudinal axis (61) and elongate members (302, 304, 306) in the straight configuration.

In some versions, multi-planar articulation joint (265) is configured to inhibit one or more elongate members (302, 304, 306, 308) from translating within multi-planar articulation joint (265). Referring to FIGS. 72-73, multi-planar articulation joint (265) is configured to maintain the spaced relationship between elongate members (302, 304, 306, 308) (see FIG. 55) at each articulation axis (55, 57) during articulation of articulation section (270). As shown in FIG. 72, proximal plate (230) is positioned along first articulation axis (55) such that first articulation axis (55) intersects longitudinal axis (61) at first point ($P_1$) at a central portion of proximal plate (230). Recesses (262, 264) and lumens (266, 268) of multi-lumen assembly (258) (see FIG. 64) that support elongate members (302, 304, 306, 308) are each radially offset from first point ($P_1$) at a predetermined distance. Accordingly, proximal plate (230) and multi-lumen assembly (258) (see FIG. 64) maintain this radial space at first point ($P_1$) at the predetermined distance as articulation section (270) is deflected from a straight configuration with articulation section (270) aligned along longitudinal axis (61) to a deflected configuration with articulation section (270) pivoted about first articulation axis (55) to deflect end effector (116) (see FIG. 54) upwardly and/or downwardly along the first plane relative to longitudinal axis (61). As shown in FIG. 73, distal plate (240) is positioned along second articulation axis (57) such that second articulation axis (57) intersects longitudinal axis (61) at second point ($P_2$) at a central portion of distal plate (240). Recesses (262, 264) and lumens (266, 268) of multi-lumen assembly (258) that support elongate members (302, 304, 306, 308) are each radially offset from second point ($P_2$) at a predetermined distance. Accordingly, distal plate (240) and multi-lumen assembly (258) (see FIG. 64) maintain this radial space at second point ($P_2$) at the predetermined distance as articulation section (270) is deflected from a straight configuration with articulation section (270) aligned along longitudinal axis (61) to a deflected configuration with articulation section (270) pivoted about second articulation axis (57) to deflect end effector (116) (see FIG. 54) outwardly and/or inwardly along the second plane relative to longitudinal axis (61). With elongate members (302, 304, 306, 308) positioned through recesses (262, 264) and lumens (266, 268), multi-planar articulation joint (265) is thereby configured to maintain the radially spaced relationship between elongate members (302, 304, 306, 308) at each articulation axis (55, 57) during articulation of articulation section (270). Still other suitable configurations for multi-planar articulation joint (265) will be apparent to one with ordinary skill in the art in view of the teachings herein.

II. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) an end effector; and (b) a shaft assembly, including: (i) a proximal shaft portion longitudinally extending along a proximal axis, (ii) a distal shaft portion longitudinally extending along a distal axis, wherein the end effector distally extends from the distal shaft portion, (iii) a first elongate member extending from the proximal shaft portion and toward the end effector, wherein the first elongate member is operatively connected to at least one of the distal shaft portion or the end effector and configured to be selectively moved, and (iv) an articulation section extending between the proximal and distal shaft portions and configured to articulate about a first articulation axis and about a second articulation axis distal of the first articulation axis to thereby respectively deflect the end effector along a first plane and a second plane; wherein the first articulation axis intersects the proximal axis at a first intersection point, wherein the second articulation axis intersects the distal axis at a second intersection point, and wherein the articulation section includes a first lumen radially offset at a predetermined distance from each of the proximal and distal axes at each of the first and second intersection points when the end effector is in a straight configuration with the distal axis longitudinally aligned with the proximal axis; wherein the first lumen movably supports the first elongate member therethrough such that the radial spacing of the first elongate member is maintained at the predetermined distance at each of the first and second intersection points when the end effector is deflected to a deflected configuration along at least one of the first and second planes.

Example 2

The surgical instrument of Example 1, wherein the first elongate member intersects each of the first and second articulation axes for deflection of the end effector.

Example 3

The surgical instrument of any one or more of Examples 1 through 2, wherein the first lumen spirals from the first articulation axis to the second articulation axis to define a helical lumen.

Example 4

The surgical instrument of any one or more of Examples 1 through 3, wherein the shaft assembly further includes a second elongate member extending from the proximal shaft portion and toward the end effector, wherein the second elongate member is operatively connected to at least one of the distal shaft portion or the end effector and configured to be selectively moved, wherein the articulation section further includes a second lumen radially offset at a predetermined distance from each of the proximal and distal axes at each of the first and second intersection points when the end effector is in the straight configuration, wherein the second lumen movably supports the second elongate member therethrough such that the radial spacing of the second elongate member is maintained at the predetermined distance at each of the first and second intersection points when the end effector is deflected to the deflected configuration.

Example 5

The surgical instrument of Example 4, wherein the second elongate member intersects each of the first and second articulation axes for deflection of the end effector.

Example 6

The surgical instrument of any or more of Examples 4 through 5, wherein the first and second lumens are radially offset from each other.

Example 7

The surgical instrument of any one or more of Examples 4 through 6, wherein the shaft assembly further includes a central elongate member extending from the proximal shaft portion and toward the end effector, wherein the central elongate member is operatively connected to at least one of the distal shaft portion or the end effector and configured to be selectively moved, wherein the articulation section further includes a central lumen aligned with each of the proximal and distal axes that longitudinally intersects each of the proximal and distal articulation axes, wherein the central lumen movably supports the central elongate member therethrough such that the central elongate member intersects each of the first and second articulation axes for deflection of the end effector.

Example 8

The surgical instrument of Example 7, wherein each of the first and second lumens spirals around the central lumen from the first articulation axis to the second articulation axis to define a collective helical configuration.

Example 9

The surgical instrument of Example 1, wherein the shaft assembly further includes a central elongate member extending from the proximal shaft portion and toward the end effector, wherein the central elongate member is operatively connected to at least one of the distal shaft portion or the end effector and configured to be selectively moved, wherein the articulation section further includes a central lumen aligned with each of the proximal and distal axes that longitudinally intersects each of the first and second articulation axes, wherein the central lumen movably supports the central elongate member therethrough such that the central elongate member intersects each of the distal and proximal articulation axes for deflection of the end effector, wherein the first lumen spirals around the central lumen from the proximal articulation axis to the distal articulation axis to define a collective helical configuration.

Example 10

The surgical instrument of any one or more of Examples 1 through 9, wherein the articulation section includes multi-planar articulation joint including a proximal articulation joint interface coupled with the proximal shaft portion, a distal articulation joint interface coupled with the distal shaft portion, and an articulation joint core pivotally coupled between each of the proximal and distal joint interfaces respectively at the proximal articulation axis and the distal articulation axis.

Example 11

The surgical instrument of Example 10, wherein the articulation joint core has a first articulation joint member and a second articulation joint member, and wherein the first and second articulation joint members collectively define the first lumen therebetween.

Example 12

The surgical instrument of any one or more of Examples 10 through 11, wherein each of the proximal and distal articulation joint interfaces includes a body having a protrusion extending outwardly from the body, wherein the articulation joint core has a wedge portion, and wherein the protrusion aligns with the wedge portion to support the first elongate member in a wedge style configuration.

Example 13

The surgical instrument of any one or more of Examples 10 through 11, wherein each of the proximal and distal articulation joint interfaces includes a body having an indentation extending inwardly within the body, wherein the articulation joint core has a protrusion, and wherein the indentation aligns with the protrusion to support the first elongate member in a lobe style configuration.

Example 14

The surgical instrument of Example 1, wherein the articulation section includes a proximal plate defining the first lumen, wherein the proximal plate intersects the first articulation axis, wherein the articulation section further includes a distal plate defining a second lumen longitudinally aligned with the first lumen for movably supporting the first elongate member therethrough, wherein the distal plate intersects the second articulation axis.

Example 15

The surgical instrument of Example 14, wherein the shaft assembly further includes a second elongate member extending from the proximal shaft portion and toward the end effector, wherein the second elongate member is operatively connected to at least one of the distal shaft portion or the end effector and configured to be selectively moved, wherein the proximal plate further includes a third lumen radially offset at a predetermined distance from each of the proximal and distal axes at each of the first and second intersection points when the end effector is in the straight configuration, wherein the third lumen movably supports the second elongate member therethrough such that the radial spacing of the second elongate member is maintained at the predetermined distance at each of the first and second intersection points when the end effector is in the deflected position, wherein the distal plate further includes a fourth lumen longitudinally aligned with the third lumen, wherein the fourth lumen movably supports the second elongate member therethrough such that the radial spacing of the second elongate member is maintained at the predetermined distance at each of the first and second intersection points when the end effector is in the deflected position.

Example 16

The surgical instrument of Example 14, wherein the shaft assembly further includes a second elongate member extending from the proximal shaft portion and toward the end effector, wherein the second elongate member is operatively connected to at least one of the distal shaft portion or the end effector and configured to be selectively moved, wherein the articulation section further includes a multi-lumen assembly extending through the first lumen of the proximal plate and the second lumen of the distal plate, wherein the multi-lumen assembly defines a third lumen radially offset at a predetermined distance from each of the proximal and distal axes at each of the first and second intersection points when the end effector is in the straight configuration, wherein the third lumen movably supports the first elongate member therethrough such that the radial spacing of the first elongate member is maintained at the predetermined distance at each of the first and second intersection points when the end effector is in the deflected position, wherein the multi-lumen assembly defines a fourth lumen radially offset at a predetermined distance from each of the proximal and distal axes at each of the first and second intersection points when the end effector is in the straight configuration, wherein the fourth lumen movably supports the second elongate member therethrough such that the radial spacing of the second elongate member is maintained at the predetermined distance at each of the first and second intersection points when the end effector is in the deflected position.

Example 17

A surgical instrument, comprising: (a) an end effector; and (b) a shaft assembly, including: (i) a proximal shaft portion longitudinally extending along a proximal axis, (ii) a distal shaft portion longitudinally extending along a distal axis, wherein the end effector distally extends from the distal shaft portion, (iii) a first elongate member extending from the proximal shaft portion and toward the end effector, wherein the first elongate member is operatively connected to at least one of the distal shaft portion or the end effector and configured to be selectively moved, and (iv) an articulation section extending between the proximal and distal shaft portions and configured to articulate about a first articulation axis and about a second articulation axis distal of the first articulation axis to thereby respectively deflect the end effector along a first plane and a second plane, and wherein the articulation section includes a first lumen radially offset from each of the proximal and distal axes that longitudinally intersects each of the first and second articulation axes, wherein the first lumen movably supports the first elongate member therethrough such that the first elongate member intersects each of the first and second articulation axes for deflection of the end effector.

Example 18

The surgical instrument of Example 17, wherein the first lumen spirals from the first articulation axis to the second articulation axis to define a helical lumen.

Example 19

The surgical instrument of any one or more of Examples 17 through 18, wherein the first articulation axis is longitudinally offset from the second articulation axis and perpendicular to the second articulation axis.

Example 20

A method of operating a surgical instrument, the surgical instrument having (a) an end effector and (b) a shaft assembly, including (i) a proximal shaft portion longitudinally extending along a proximal axis, (ii) a distal shaft portion longitudinally extending along a distal axis, wherein the end effector distally extends from the distal shaft portion, (iii) a first elongate member extending from the proximal shaft portion and toward the end effector, wherein the first elongate member is operatively connected to at least one of the distal shaft portion or the end effector and configured to be selectively moved, and (iv) an articulation section extending between the proximal and distal shaft portions and configured to articulate about a first articulation axis and about a second articulation axis distal of the first articulation axis to thereby respectively deflect the end effector along a first plane and a second plane, wherein the first articulation axis intersects the proximal axis at a first intersection point, wherein the second articulation axis intersects the distal axis at a second intersection point, and wherein the articulation section includes a first lumen radially offset at a predetermined distance from each of the proximal and distal axes at each of the first and second intersection points when the end effector is in a straight configuration with the distal axis longitudinally aligned with the proximal axis, wherein the first lumen movably supports the first elongate member therethrough such that the radial spacing of the first elongate member is maintained at the predetermined distance at each of the first and second intersection points when the end effector is deflected to a deflected configuration along at least one of the first and second planes, the method comprising: (a) actuating the first elongate member through each of the first articulation axis and the second articulation axis thereby operating the surgical instrument.

III. Miscellaneous

Any one or more of the teaching, expressions, embodiments, examples, etc. described herein may be combined with any one or more of the teachings, expressions, embodiments, examples, etc. described in U.S. patent application Ser. No. 16/556,661, entitled "Ultrasonic Surgical Instrument with a Multi-Planar Articulating Shaft Assembly," filed on Aug. 30, 2019, published as U.S. Pat. Pub. No. 2021/0059709 on Mar. 4, 2021, issued as U.S. Pat. No. 11,690,642 on Jul. 4, 2023; U.S. patent application Ser. No. 16/556,667, entitled "Ultrasonic Transducer Alignment of an Articulating Ultrasonic Surgical Instrument," filed on Aug. 30, 2019, published as U.S. Pat. Pub. No. 2021/0059710 on Mar. 4, 2021, issued as U.S. Pat. No. 11,612,409; U.S. patent application Ser. No. 16/556,625, entitled "Ultrasonic Surgical Instrument with Axisymmetric Clamping," filed on Aug. 30, 2019, published as U.S. Pat. Pub. No. 2021/0059707 on Mar. 4, 2021, issued as U.S. Pat. No. 11,471,181 on Oct. 18, 2022; U.S. patent application Ser. No. 16/556,635, entitled "Ultrasonic Blade and Clamp Arm Alignment Features," filed on Aug. 30, 2019, U.S. Pat. Pub. No. 2021/0059708 on Mar. 4, 2021, issued as U.S. Pat. No. 11,457,945 on Oct. 4, 2022; and/or U.S. patent application Ser. No. 16/556,727, entitled "Rotatable Linear Actuation Mechanism," filed on Aug. 30, 2019, published as U.S. Pat. Pub. No. 2021/

0059711 on Mar. 4, 2021, issued as U.S. Pat. No. 11,712,261 on Aug. 1, 2023. The disclosure of each of these applications is incorporated by reference herein.

It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. Nos. 5,322,055; 5,873,873; 5,980,510; 6,325,811; 6,773,444; 6,783,524; 9,095,367; U.S. Pub. No. 2006/0079874, now abandoned; U.S. Pub. No. 2007/0191713, now abandoned; U.S. Pub. No. 2007/0282333, now abandoned; U.S. Pub. No. 2008/0200940, now abandoned; U.S. Pat. No. 8,623,027, issued Jan. 7, 2014; U.S. Pat. No. 9,023,071, issued May 5, 2015; U.S. Pat. No. 8,461,744, issued Jun. 11, 2013; U.S. Pat. No. 9,381,058, issued Jul. 5, 2016; U.S. Pub. No. 2012/0116265, now abandoned; U.S. Pat. No. 9,393,037, issued Jul. 19, 2016; U.S. Pat. No. 10,172,636, issued Jan. 8, 2019; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into another example of a robotic surgical system, and those of ordinary skill in the art will recognize that various teachings herein may be readily combined with various teachings of any of the following: U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument, comprising:
    (a) an end effector; and
    (b) a shaft assembly, including:
        (i) a proximal shaft portion longitudinally extending along a proximal axis,
        (ii) a distal shaft portion longitudinally extending along a distal axis, wherein the end effector distally extends from the distal shaft portion,
        (iii) a first elongate member extending from the proximal shaft portion and toward the end effector, wherein the first elongate member is operatively connected to at least one of the distal shaft portion or the end effector and configured to be selectively moved, and
        (iv) an articulation section extending between the proximal and distal shaft portions and configured to articulate about a first articulation axis and about a second articulation axis distal of the first articulation axis to thereby respectively deflect the end effector along a first plane and a second plane;
    wherein the first articulation axis intersects the proximal axis at a first intersection point, wherein the second articulation axis intersects the distal axis at a second intersection point, and wherein the articulation section includes a first lumen radially offset at a predetermined distance from each of the proximal and distal axes at each of the first and second intersection points when the end effector is in a straight configuration with the distal axis longitudinally aligned with the proximal axis;
    wherein the first lumen movably supports the first elongate member therethrough such that the radial spacing of the first elongate member is maintained at the predetermined distance at each of the first and second intersection points when the end effector is deflected to a deflected configuration along at least one of the first and second planes,
    wherein the first elongate member intersects each of the first and second articulation axes for deflection of the end effector.

2. The surgical instrument of claim 1, wherein the first lumen spirals from the first articulation axis to the second articulation axis to define a helical lumen.

3. The surgical instrument of claim 1, wherein the shaft assembly further includes a second elongate member extending from the proximal shaft portion and toward the end effector, wherein the second elongate member is operatively connected to at least one of the distal shaft portion or the end effector and configured to be selectively moved, wherein the articulation section further includes a second lumen radially offset at a predetermined distance from each of the proximal and distal axes at each of the first and second intersection points when the end effector is in the straight configuration, wherein the second lumen movably supports the second elongate member therethrough such that the radial spacing of the second elongate member is maintained at the predetermined distance at each of the first and second intersection points when the end effector is deflected to the deflected configuration.

4. The surgical instrument of claim 3, wherein the second elongate member intersects each of the first and second articulation axes for deflection of the end effector.

5. The surgical instrument of claim 3, wherein the first and second lumens are radially offset from each other.

6. The surgical instrument of claim 3, wherein the shaft assembly further includes a central elongate member extending from the proximal shaft portion and toward the end effector, wherein the central elongate member is operatively connected to at least one of the distal shaft portion or the end effector and configured to be selectively moved, wherein the articulation section further includes a central lumen aligned with each of the proximal and distal axes that longitudinally intersects each of the proximal and distal articulation axes, wherein the central lumen movably supports the central elongate member therethrough such that the central elongate member intersects each of the first and second articulation axes for deflection of the end effector.

7. The surgical instrument of claim 6, wherein each of the first and second lumens spirals around the central lumen from the first articulation axis to the second articulation axis to define a collective helical configuration.

8. The surgical instrument of claim 1, wherein the shaft assembly further includes a central elongate member extending from the proximal shaft portion and toward the end effector, wherein the central elongate member is operatively connected to at least one of the distal shaft portion or the end effector and configured to be selectively moved, wherein the articulation section further includes a central lumen aligned with each of the proximal and distal axes that longitudinally intersects each of the first and second articulation axes, wherein the central lumen movably supports the central elongate member therethrough such that the central elongate member intersects each of the distal and proximal articulation axes for deflection of the end effector, wherein the first lumen spirals around the central lumen from the proximal articulation axis to the distal articulation axis to define a collective helical configuration.

9. The surgical instrument of claim 1, wherein the articulation section includes multi-planar articulation joint including a proximal articulation joint interface coupled with the proximal shaft portion, a distal articulation joint interface coupled with the distal shaft portion, and an articulation joint core pivotally coupled between each of the proximal and distal joint interfaces respectively at the proximal articulation axis and the distal articulation axis.

10. The surgical instrument of claim 9, wherein the articulation joint core has a first articulation joint member and a second articulation joint member, and wherein the first and second articulation joint members collectively define the first lumen therebetween.

11. The surgical instrument of claim 9, wherein each of the proximal and distal articulation joint interfaces includes a body having a protrusion extending outwardly from the body, wherein the articulation joint core has a wedge portion, and wherein the protrusion aligns with the wedge portion to support the first elongate member in a wedge style configuration.

12. The surgical instrument of claim 9, wherein each of the proximal and distal articulation joint interfaces includes a body having an indentation extending inwardly within the body, wherein the articulation joint core has a protrusion, and wherein the indentation aligns with the protrusion to support the first elongate member in a lobe style configuration.

13. The surgical instrument of claim 1, wherein the articulation section includes a proximal plate defining the first lumen, wherein the proximal plate intersects the first articulation axis, wherein the articulation section further includes a distal plate defining a second lumen longitudinally aligned with the first lumen for movably supporting the first elongate member therethrough, wherein the distal plate intersects the second articulation axis.

14. The surgical instrument of claim 13, wherein the shaft assembly further includes a second elongate member extending from the proximal shaft portion and toward the end effector, wherein the second elongate member is operatively connected to at least one of the distal shaft portion or the end effector and configured to be selectively moved, wherein the proximal plate further includes a third lumen radially offset at a predetermined distance from each of the proximal and distal axes at each of the first and second intersection points when the end effector is in the straight configuration, wherein the third lumen movably supports the second elongate member therethrough such that the radial spacing of the second elongate member is maintained at the predetermined distance at each of the first and second intersection points when the end effector is in the deflected position, wherein the distal plate further includes a fourth lumen longitudinally aligned with the third lumen, wherein the fourth lumen movably supports the second elongate member therethrough such that the radial spacing of the second elongate member is maintained at the predetermined distance at each of the first and second intersection points when the end effector is in the deflected position.

15. The surgical instrument of claim 13, wherein the shaft assembly further includes a second elongate member extending from the proximal shaft portion and toward the end effector, wherein the second elongate member is operatively connected to at least one of the distal shaft portion or the end effector and configured to be selectively moved, wherein the articulation section further includes a multi-lumen assembly extending through the first lumen of the proximal plate and the second lumen of the distal plate, wherein the multi-lumen assembly defines a third lumen radially offset at a predetermined distance from each of the proximal and distal axes at each of the first and second intersection points when the end effector is in the straight configuration, wherein the third lumen movably supports the first elongate member therethrough such that the radial spacing of the first elongate member is maintained at the predetermined distance at each of the first and second intersection points when the end effector is in the deflected position, wherein the multi-lumen assembly defines a fourth lumen radially offset at a predetermined distance from each of the proximal and distal axes at each of the first and second intersection points when the end effector is in the straight configuration, wherein the fourth lumen movably supports the second elongate member therethrough such that the radial spacing of the second elongate member is maintained at the predetermined distance at each of the first and second intersection points when the end effector is in the deflected position.

16. A surgical instrument, comprising:
(a) an end effector; and
(b) a shaft assembly, including:
(i) a proximal shaft portion longitudinally extending along a proximal axis,
(ii) a distal shaft portion longitudinally extending along a distal axis, wherein the end effector distally extends from the distal shaft portion,
(iii) a first elongate member extending from the proximal shaft portion and toward the end effector, wherein the first elongate member is operatively connected to at least one of the distal shaft portion or the end effector and configured to be selectively moved, and
(iv) an articulation section extending between the proximal and distal shaft portions and configured to articulate about a first articulation axis and about a second articulation axis distal of the first articulation axis to thereby respectively deflect the end effector along a first plane and a second plane, and wherein the articulation section includes a first lumen radially offset from each of the proximal and distal axes that longitudinally intersects each of the first and second articulation axes,
wherein the first lumen movably supports the first elongate member therethrough such that the first elongate member intersects each of the first and second articulation axes for deflection of the end effector.

17. The surgical instrument of claim 16, wherein the first lumen spirals from the first articulation axis to the second articulation axis to define a helical lumen.

18. The surgical instrument of claim 16, wherein the first articulation axis is longitudinally offset from the second articulation axis and perpendicular to the second articulation axis.

19. A method of operating a surgical instrument, the surgical instrument having (a) an end effector and (b) a shaft assembly, including (i) a proximal shaft portion longitudinally extending along a proximal axis, (ii) a distal shaft portion longitudinally extending along a distal axis, wherein the end effector distally extends from the distal shaft portion, (iii) a first elongate member extending from the proximal shaft portion and toward the end effector, wherein the first elongate member is operatively connected to at least one of the distal shaft portion or the end effector and configured to be selectively moved, and (iv) an articulation section extending between the proximal and distal shaft portions and configured to articulate about a first articulation axis and about a second articulation axis distal of the first articulation axis to thereby respectively deflect the end effector along a first plane and a second plane, wherein the first articulation axis intersects the proximal axis at a first intersection point, wherein the second articulation axis intersects the distal axis at a second intersection point, and wherein the articulation section includes a first lumen radially offset at a predetermined distance from each of the proximal and distal axes at each of the first and second intersection points when the end effector is in a straight configuration with the distal axis longitudinally aligned with the proximal axis, wherein the first lumen movably supports the first elongate member therethrough such that the radial spacing of the first elongate member is maintained at the predetermined distance at each of the first and second intersection points when the end effector is deflected to a deflected configuration along at least one of the first and second planes, the method comprising:
(a) actuating the first elongate member through each of the first articulation axis and the second articulation axis thereby operating the surgical instrument.

20. The method of claim 19, wherein the first elongate member intersects each of the first and second articulation axes for deflection of the end effector.

* * * * *